(12) United States Patent
Nelson et al.

(10) Patent No.: US 10,350,100 B2
(45) Date of Patent: Jul. 16, 2019

(54) SYSTEM FOR DETECTING AN INTRAGASTRIC BALLOON

(71) Applicant: Obalon Therapeutics, Inc., Carlsbad, CA (US)

(72) Inventors: Sheldon Nelson, Vista, CA (US); Neil R. Drake, San Diego, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 301 days.

(21) Appl. No.: 15/461,293

(22) Filed: Mar. 16, 2017

(65) Prior Publication Data

US 2017/0290693 A1 Oct. 12, 2017

Related U.S. Application Data

(60) Provisional application No. 62/321,563, filed on Apr. 12, 2016.

(51) Int. Cl.
*A61B 5/00* (2006.01)
*A61B 5/06* (2006.01)
(Continued)

(52) U.S. Cl.
CPC .......... *A61F 5/0036* (2013.01); *A61B 5/4887* (2013.01); *A61B 34/20* (2016.02);
(Continued)

(58) Field of Classification Search
CPC ................. A61B 5/4887; A61B 5/065; A61B 2034/2055; A61B 34/20; A61B 90/39;
(Continued)

(56) References Cited

U.S. PATENT DOCUMENTS 2,183,900 A 12/1939 Voit et al.
3,788,322 A 1/1974 Michaels
(Continued)

FOREIGN PATENT DOCUMENTS

DE 3540936 10/1986
EP 0 103 481 3/1984
(Continued)

OTHER PUBLICATIONS

Al Kahtani et al., Aug. 28, 2008, Bio-Enteric Intragastric Balloon in Obese Patients: A Retrospective Analysis of King Faisal Specialist Hospital Experience; Obesity Surgery, 8 pp.
(Continued)

*Primary Examiner* — Katrina M Stransky
(74) *Attorney, Agent, or Firm* — Knobbe Martens Olson & Bear, LLP

(57) ABSTRACT

Devices and methods for treating obesity are provided, including intragastric devices and methods of fabricating, deploying, inflating, locating, tracking, monitoring, deflating, and retrieving the same. In one embodiment, a device includes a balloon capsule having a distal end, a catheter having a proximal end and a distal end, a connector, a light sensor, and a balloon valve. At least one optical fiber extends along the length of the interior of the catheter and through the valve such that a distal end of the optical fiber is positioned at a distal end of the balloon capsule when the catheter is placed within the balloon capsule, and such that a proximal end of the optical fiber can be received by the light sensor.

20 Claims, 3 Drawing Sheets

(51) Int. Cl.
*A61F 5/00* (2006.01)
*A61B 34/20* (2016.01)
*A61B 90/00* (2016.01)

(52) U.S. Cl.
CPC .............. *A61B 90/39* (2016.02); *A61F 5/003* (2013.01); *A61B 5/065* (2013.01); *A61B 2034/2055* (2016.02); *A61B 2090/3945* (2016.02)

(58) Field of Classification Search
CPC .............. A61B 2090/3945; A61F 5/003; A61F 5/0036; A61F 5/004; A61F 5/0043; A61F 5/0046; A61F 5/0003; A61F 5/0013; A61F 2005/0016; A61F 2005/002; A61F 2005/0023
See application file for complete search history.

(56) References Cited

U.S. PATENT DOCUMENTS

| | | |
|---|---|---|
| 3,797,492 A | 3/1974 | Place |
| 4,133,315 A | 1/1979 | Berman et al. |
| 4,234,454 A | 11/1980 | Strope |
| 4,236,521 A | 12/1980 | Lauterjung |
| 4,246,893 A | 1/1981 | Berson |
| 4,340,626 A | 7/1982 | Rudy |
| 4,485,805 A | 12/1984 | Foster, Jr. |
| 4,489,440 A | 12/1984 | Chaoui |
| 4,517,979 A | 5/1985 | Pecenka |
| 4,545,367 A | 10/1985 | Tucci |
| 4,560,392 A | 12/1985 | Basevi |
| 4,607,618 A | 8/1986 | Angelchik |
| 4,694,827 A | 9/1987 | Weiner et al. |
| 4,718,639 A | 1/1988 | Sherwood et al. |
| 4,723,547 A | 2/1988 | Kullas et al. |
| 4,739,758 A | 4/1988 | Lai et al. |
| 4,748,562 A | 5/1988 | Miller et al. |
| 4,812,315 A | 3/1989 | Tarabishi |
| 4,813,934 A | 3/1989 | Engelson et al. |
| 4,857,029 A | 8/1989 | Dierick et al. |
| 4,899,747 A | 2/1990 | Garren et al. |
| 4,917,885 A | 4/1990 | Chiba et al. |
| 4,925,446 A | 5/1990 | Garay et al. |
| 4,929,214 A | 5/1990 | Liebermann |
| 5,049,106 A | 9/1991 | Kim et al. |
| 5,084,061 A | 1/1992 | Gau et al. |
| 5,129,915 A | 7/1992 | Cantenys et al. |
| 5,234,454 A | 8/1993 | Bangs |
| 5,259,399 A | 11/1993 | Brown |
| 5,308,326 A | 5/1994 | Zimmon |
| 5,425,382 A | 6/1995 | Golden et al. |
| 5,431,917 A | 7/1995 | Yamamoto et al. |
| 5,622,169 A | 4/1997 | Golden et al. |
| 5,713,141 A | 2/1998 | Mitchell et al. |
| 5,728,119 A | 3/1998 | Smith et al. |
| 5,852,889 A | 12/1998 | Rinaldi |
| 5,868,141 A | 2/1999 | Ellias |
| 5,879,297 A | 3/1999 | Haynor et al. |
| 5,897,205 A | 4/1999 | Sinsteden |
| 5,910,128 A | 6/1999 | Quinn |
| 5,948,227 A | 9/1999 | Dubrow |
| 6,042,710 A | 3/2000 | Dubrow |
| 6,129,668 A | 10/2000 | Haynor et al. |
| 6,216,028 B1 | 4/2001 | Haynor et al. |
| 6,263,230 B1 | 7/2001 | Haynor et al. |
| 6,427,089 B1 | 7/2002 | Knowlton |
| 6,454,785 B2 | 9/2002 | De Hoyos Garza |
| 6,579,301 B1 | 6/2003 | Bales et al. |
| 6,682,473 B1 | 1/2004 | Matsuura et al. |
| 6,733,512 B2 | 5/2004 | McGhan et al. |
| 6,981,980 B2 | 1/2006 | Sampson et al. |
| 6,988,983 B2 | 1/2006 | Connors et al. |
| 7,031,946 B1 | 4/2006 | Tamai et al. |
| 7,032,822 B2 | 4/2006 | Waters |
| 7,035,818 B1 | 4/2006 | Bandy et al. |
| 7,035,877 B2 | 4/2006 | Markham et al. |
| 7,192,397 B2 | 3/2007 | Lewkowicz et al. |
| 7,682,306 B2 | 3/2010 | Shah |
| 7,699,863 B2 | 4/2010 | Marco et al. |
| 7,854,745 B2 | 12/2010 | Brister et al. |
| 8,105,247 B2 | 1/2012 | Buchwald |
| 8,162,969 B2 | 4/2012 | Brister et al. |
| 8,202,291 B1 | 6/2012 | Brister et al. |
| 8,282,666 B2 | 10/2012 | Birk |
| 8,292,911 B2 | 10/2012 | Brister et al. |
| 8,428,691 B2 | 4/2013 | Byrd et al. |
| 8,491,464 B2 | 7/2013 | Yokoi et al. |
| 8,535,230 B2 | 9/2013 | Maschke |
| 8,562,589 B2 | 10/2013 | Imran |
| 8,721,620 B2 | 5/2014 | Imran |
| 8,734,429 B2 | 5/2014 | Imran et al. |
| 8,764,733 B2 | 7/2014 | Imran |
| 8,809,269 B2 | 8/2014 | Imran |
| 8,809,271 B2 | 8/2014 | Imran |
| 8,836,513 B2 | 9/2014 | Hafezi et al. |
| 8,847,766 B2 | 9/2014 | Zdeblick et al. |
| 8,858,432 B2 | 10/2014 | Robertson et al. |
| 8,870,966 B2 | 10/2014 | Schwab et al. |
| 2003/0021822 A1 | 1/2003 | Lloyd |
| 2003/0171768 A1 | 9/2003 | McGhan |
| 2004/0044351 A1 | 3/2004 | Searle |
| 2004/0102677 A1 | 5/2004 | Frering |
| 2004/0186502 A1 | 9/2004 | Sampson |
| 2005/0124875 A1* | 6/2005 | Kawano ............. A61B 1/00048 600/407 |
| 2005/0131281 A1 | 6/2005 | Ayer et al. |
| 2005/0192614 A1 | 9/2005 | Binmoeller |
| 2005/0222329 A1 | 10/2005 | Shah et al. |
| 2005/0266109 A1 | 12/2005 | Chin et al. |
| 2005/0267405 A1 | 12/2005 | Shah |
| 2005/0267595 A1 | 12/2005 | Chen et al. |
| 2006/0058829 A1 | 3/2006 | Sampson et al. |
| 2006/0178691 A1 | 8/2006 | Binmoeller |
| 2006/0224145 A1 | 10/2006 | Gillis et al. |
| 2007/0078476 A1 | 4/2007 | Hull et al. |
| 2007/0100208 A1 | 5/2007 | Lewkowicz et al. |
| 2007/0100369 A1 | 5/2007 | Cragg et al. |
| 2007/0104754 A1 | 5/2007 | Sterling et al. |
| 2007/0104755 A1 | 5/2007 | Sterling et al. |
| 2007/0110934 A1 | 5/2007 | Goldman |
| 2007/0129735 A1 | 6/2007 | Filipi et al. |
| 2007/0149994 A1 | 6/2007 | Sosnowski et al. |
| 2007/0156248 A1 | 7/2007 | Marco et al. |
| 2007/0173881 A1 | 7/2007 | Birk et al. |
| 2007/0207199 A1 | 9/2007 | Sogin et al. |
| 2007/0212559 A1 | 9/2007 | Shah |
| 2007/0250101 A1 | 10/2007 | Horn et al. |
| 2007/0288033 A1 | 12/2007 | Murature et al. |
| 2007/0293885 A1 | 12/2007 | Binmoeller |
| 2008/0051866 A1 | 2/2008 | Chen et al. |
| 2008/0172079 A1 | 7/2008 | Birk |
| 2008/0255601 A1 | 10/2008 | Birk |
| 2008/0306506 A1 | 12/2008 | Leatherman et al. |
| 2009/0012372 A1* | 1/2009 | Burnett ................. A61B 5/076 600/300 |
| 2009/0082644 A1 | 3/2009 | Li |
| 2009/0118756 A1 | 5/2009 | Valencon et al. |
| 2009/0182368 A1 | 7/2009 | Lunsford et al. |
| 2009/0182424 A1 | 7/2009 | Marco et al. |
| 2009/0187206 A1 | 7/2009 | Binmoeller et al. |
| 2009/0192535 A1 | 7/2009 | Kasic, II et al. |
| 2009/0222065 A1 | 9/2009 | Dlugos et al. |
| 2009/0259246 A1 | 10/2009 | Eskaros et al. |
| 2010/0063530 A1 | 3/2010 | Valencon |
| 2010/0100115 A1 | 4/2010 | Soetermans et al. |
| 2010/0100116 A1 | 4/2010 | Brister et al. |
| 2010/0100117 A1 | 4/2010 | Brister et al. |
| 2010/0137897 A1 | 6/2010 | Brister et al. |
| 2010/0168782 A1 | 7/2010 | Hancock |
| 2010/0198249 A1 | 8/2010 | Sabliere |
| 2010/0222802 A1 | 9/2010 | Gillespie et al. |
| 2011/0021881 A1 | 1/2011 | Wenchell et al. |

(56) References Cited

U.S. PATENT DOCUMENTS

| | | | |
|---|---|---|---|
| 2011/0196411 A1* | 8/2011 | Forsell | A61B 17/0469 606/191 |
| 2011/0202127 A1 | 8/2011 | Mauch et al. | |
| 2011/0295300 A1 | 12/2011 | Verd et al. | |
| 2012/0010590 A1 | 1/2012 | Imran | |
| 2012/0071710 A1* | 3/2012 | Gazdzinski | A61B 1/00016 600/101 |
| 2012/0191123 A1 | 7/2012 | Brister et al. | |
| 2012/0191124 A1 | 7/2012 | Brister et al. | |
| 2012/0232576 A1 | 9/2012 | Brister et al. | |
| 2012/0296365 A1 | 11/2012 | Nguyen | |
| 2013/0012980 A1 | 1/2013 | Brister et al. | |
| 2013/0165859 A1 | 6/2013 | Imran | |
| 2013/0211261 A1* | 8/2013 | Wang | A61B 5/055 600/476 |
| 2013/0218190 A1* | 8/2013 | Gaur | A61F 5/003 606/192 |
| 2013/0226219 A1 | 8/2013 | Brister et al. | |
| 2013/0267983 A1 | 10/2013 | Pavlovic et al. | |
| 2013/0289604 A1 | 10/2013 | Brister et al. | |
| 2014/0066968 A1 | 3/2014 | Pavlovic et al. | |
| 2014/0188151 A1* | 7/2014 | Gaur | A61F 5/003 606/192 |
| 2014/0221912 A1 | 8/2014 | Imran | |
| 2014/0221927 A1 | 8/2014 | Imran et al. | |
| 2015/0196408 A1* | 7/2015 | Moss | A61F 5/003 606/192 |

FOREIGN PATENT DOCUMENTS

| | | |
|---|---|---|
| EP | 0 246 999 | 11/1987 |
| JP | 62-286470 | 12/1987 |
| WO | WO 87/00034 | 1/1987 |
| WO | WO 99/25418 | 5/1999 |
| WO | WO 01/068007 | 9/2001 |
| WO | WO 02/016001 | 2/2002 |
| WO | WO 02/040081 | 5/2002 |
| WO | WO 02/091961 | 11/2002 |
| WO | WO 03/055420 | 7/2003 |
| WO | WO 04/084763 | 10/2004 |
| WO | WO 06/020929 | 2/2006 |
| WO | WO 06/116718 | 11/2006 |
| WO | WO 07/053556 | 5/2007 |
| WO | WO 07/074445 | 7/2007 |
| WO | WO 07/136735 | 11/2007 |
| WO | WO 08/052136 | 5/2008 |
| WO | WO 09/055386 | 4/2009 |
| WO | WO 09/059803 | 5/2009 |
| WO | WO 09/086119 | 7/2009 |
| WO | WO 10/045477 | 4/2010 |
| WO | WO 10/045482 | 4/2010 |
| WO | WO 10/097774 | 8/2010 |
| WO | WO 11/136745 | 11/2011 |
| WO | WO 12/099610 | 7/2012 |

OTHER PUBLICATIONS

Almeida et al., 2008, Capsule endoscopy assisted by traditional upper endoscopy Revista Española De Enfermedades Digestives, 100(12):758-763.

Al-Momen et al., 2005, Intragastric Balloon for Obesity: A Retrospective Evaluation of Tolerance and Efficacy, Obesity Surgery, 15(1):101-105.

Ambe et al., 2012, Swallowed Foreign Bodies in Adults Dtsch Arztebl Int, 109(50):869-875.

Bar-Shalom et al., 1988, Tracking and Data Association, Academic Press, Inc., Boston.

Benjamin et al., Sep. 1988, Double-Blind Controlled Trial of the Garren-Edwards Gastric Bubble: An Adjunctive Treatment for Exogenous Obesity, Gastroenterology, 95(3):581-588.

Carvalho et al., 2008, An Improved Intragastric Balloon Procedure Using a New Balloon: Preliminary Analysis of Safety and Efficacy, Obesity Surgery, 6 pp.

Coskun et al., Sep. 2008, Bioenterics Intragastric Balloon: Clinical Outcomes of the First 100 Patients—A Turkish Experience, Obesity Surgery, 18(9):1154-1156.

Dastis et al., Jul. 2008, Intragastric Balloon for Weight Loss: Results in 100 Individuals Followed for at Least 2.5 Years; Endoscopy, 41(7):575-580.

De Waele et al., Apr. 2001, Endoscopic Volume Adjustment of Intragastric Balloons for Intolerance, Obesity Surgery, 11(2):223-224.

Doldi et al., 2002, Treatment of Morbid Obesity With Intragastric Balloon in Association With Diet; Obesity Surgery, 12(4):583-587.

Dumonceau, Dec. 2008, Evidence-Based Review of the Bioenterics Intragastric Balloon for Weight Loss, Obesity Surgery, 18(12):1611-1617.

Durrans et al., 1989, Comparison of Weight Loss With Short Term Dietary and Intragastric Balloon Treatment; Gut, 30:565-568.

Eckhauser et al., 1984, Hydrostatic Balloon Dilation for Stomal Stenosis after Gastric Partitioning, Surgical Gastroenterology, 3(1):43-50.

Evans et al., 2001, Intragastric Balloon in the Treatment of Patients With Morbid Obesity, British Journal of Surgery, 88:1245-1248.

Fernandes et al., Jan. 24, 2007, Intragastric Balloon for Obesity (Review), The Cochrane Collaboration, John Wiley & Sons, Ltd., Issue 1, 57 pp.

Forestieri et al., May 2006, Heliosphere Bag in the Treatment of Severe Obesity: Preliminary Experience, Obesity Surgery, 16(5):635-637.

Gaggiotti et al., 2007, Adjustable Totally Implanted Intragastric Prosthesis (ATIIP). Endogast for Treatment of Morbid Obesity: One Year Follow-Up of a Multicenter Prospective Clinical Survey; Obesity Surgery, 17:949-956.

Geliebter et al., 1990, Gastric balloon to treat obesity: a double-blind study in nondieting subjects, The American Journal of Clinical Nutrition, 51:584-588.

Genco et al., Jan. 2006, Bioenterics Intragastric Balloon (BIB): A Short-Term, Double-Blind, Randomized, Controlled, Crossover Study on Weight Reduction in Morbidly Obese Patients, International Journal of Obesity, 30(1):129-133.

Genco et al., 2005, Bioenterics Intragastric Balloon: The Italian Experience With 2,515 Patients; Obesity Surgery, 15(8):1161-1164.

Genco et al., 2008, Intragastric Balloon or Diet Alone? A Retrospective Evaluation, Obesity Surgery, 18(8):989-992.

Genco et al., 2009, Laparoscopic Sleeve Gastrectomy Versus Intragastric Balloon: A Case-Control Study, Surg Endosc. Springer Science & Business Media, 4 pp.

Gottig et al., Jun. 2009, Analysis of Safety and Efficacy of Intragastric Balloon in Extremely Obese Patients, Obesity Surgery, 19(6):677-683.

Imaz et al., Jul. 2008, Safety and Effectiveness of the Intragastric Balloon for Obesity. A Meta-Analysis; Obesity Surgery, 18(7):841-846.

Langer, Apr. 30, 1998, Drug delivery and targeting, Nature, 392 Supp(6679):5-10.

Mackay, 2.9. Power Sources, in Bio-Medical Telemetry: Sensing and Transmitting Biological Information from Animals and Man, 2d ed., IEEE Press, New York, 1993, pp. 62-70.

Malik, 2006, Endoluminal and Transluminal Surgery: Current Status and Future Possibilities; Surgical Endoscopy, 20(8):1179-1192.

Martin et al., Jul. 2007, Safety of the Ullorex Oral Intragastric Balloon for the Treatment of Obesity, Journal of Diabetic Science and Technology, 1(4):574-581.

Mathus-Vliegen et al., Aug. 1990, Intragastric Ballon in the Treatment of Super-morbid Obesity—Double-Blind, Sham-Controlled, Crossover Evaluation of 500-Milliliter Balloon, Gastroenterology, 99(2):362-369.

Melissas et al., 2006, The Intragastric Balloon—Smoothing The Path to Bariatric Surgery, Obesity Surgery, 16:897-902.

Mion et al., Jul. 2007, Tolerance and Efficacy of an Air-Filled Balloon in Non-Morbidly Obese Patients: Results of a Prospective Multicenter Study; Obesity Surgery, 17(7):764-769.

Nieben et al., Jan. 1982, Ingtragastric Balloon as an Artificial Bezoar for Treatment of Obesity, The Lancet, 1(8265):198-199.

(56) References Cited

OTHER PUBLICATIONS

Ramhamadany et al, 1989, Effect of the Gastric Balloon Versus Sham Procedure on Weight Loss in Obese Subjects; Gut, 30:1054-1057.
Remington's Pharmaceutical Sciences, Mace Publishing Company, Philadelphia, Pa., 17th ed. (1985).
Rodriguez-Hermosa et al., 2009, Gastric Necrosis: A Possible Complication of The Use of The Intragastric Balloon in a Patient Previously Submitted to Nissen Fundoplication; Obesity Surgery, 19:1456-1459.
Roman et al., Apr. 2004, Intragastric Balloon for "Non-Morbid" Obesity: A Retrospective Evaluation of Tolerance and Efficacy; Obesity Surgery, 14(4):539-544.
Sallet et al., Aug. 2004, Brazilian Multicenter Study of the Intragastric Balloon, Obesity Surgery, 14(7):991-998.
Sherlock II Tip Location System, Bard Access Systems, Imaging Technologies http://www.bardaccess.com/loc-sherlock.php, 1 p.
Torres et al., 2009, Management of contact dermatitis due to nickel allergy: an update, Clinical, Cosmetic and Investigational Dermatology, 2:39-48.
Totte et al., Aug. 2001, Weight Reduction by Means of Intragastric Device: Experience With the Bioenterics Intragastric Balloon, Obesity Surgery, 11(4):519-523.
Trande et al., Dec. 2008, Efficacy, Tolerance and Safety of New Intragastric Air-Filled Balloon (Heliosphere BAG) for Obesity: The Experience of 17 Cases; Obesity Surgery, 4 pp.
U.S. Food and Drug Administration. Jul. 29, 2009. 510(k) substantial equivalence clearance, Given PillCam Platform with PillCam SB Capsules with PillCam SensorBelt http://www.accessdata.fda.gov/scripts/cdrh/cfdocs/cfpmn/pmn.cfm?id=k091405, 2 pp.
U.S. Food and Drug Administration. Jun. 2, 2006. 510(k) substantial equivalence clearance, Sherlock tip location system (TLS) detector and accessories. http://www.accessdata.fda.gov/scripts/cdrh/cfdocs/cfpmn/pmn.cfm?id=k061240, 2 pp.
U.S. Food and Drug Administration. Sep. 7, 2000. 510(k) substantial equivalence clearance, Zotran Detector. http://www.accessdata.fda.gov/scripts/cdrh/cfdocs/cfpmn/pmn.cfm?id=k000997, 2 pp.
Vălean et al., Jun. 2005, Pill Esophagitis: Two Cases Reports Romanian Journal of Gastroenterology, 14(2):159-163.
vanSonnenberg et al., Aug. 1984, Percutaneous Gastrostomy: Use of Intragastric Ballon Support, Radiology, 152(2):531-532.
Vijaysadan et al., Sep.-Oct. 2006, Revisiting Swallowed Troubles: Intestinal Complications Caused by Two Magnets—A Case Report, Review and Proposed Revision to the Algorithm for the Management of Foreign Body Ingestion, JABFM, 19(5):511-516.
Wahlen et al., 2001, The Bioenterics Intragastric Balloon (BIB): How to Use It; Obesity Surgery, 11(4):524-527.
Yoshihisa et al., 2012, Metal Allergy and Systemic Contact Dermatitis: An Overview Dermatology Research and Practice, 2012:1-5, Article ID 749561.
U.S. Appl. No. 60/807,060, filed Jul. 11, 2006, titled: Acoustic Pharma-Informatic System.
U.S. Appl. No. 60/866,581, filed Nov. 20, 2006, titled: "In-Vivo Transmission Decoder".
U.S. Appl. No. 60/889,868, filed Feb. 14, 2007, titled: "Pharma Informatics System Power Source".
U.S. Appl. No. 60/889,871, filed Feb. 14, 2007, titled: "Pharma Informatics System Having Short Resistant Series Battery".

\* cited by examiner

SYSTEM FOR DETECTING AN INTRAGASTRIC BALLOON

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/321,563, filed on Apr. 12, 2016. The aforementioned application is incorporated by reference herein in its entirety, and is hereby expressly made a part of this specification.

FIELD

Devices and methods for treating obesity are provided. More particularly, intragastric devices and methods of fabricating, deploying, inflating, locating, tracking, monitoring, deflating, and retrieving the same are provided.

BACKGROUND

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Patent No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267, 4,485,805, 4,694,827, 4,739,758, and 4,899,747 and European Patent No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

After swallowing, food and oral medicaments typically reach a patient's stomach in under a minute. Food is retained in the stomach on average from one to three hours. However, the residence time is highly variable and dependent upon such factors as the fasting or fed state of the patient. Accordingly, proper timing of inflation of an intragastric balloon is a factor in successful deployment of the intragastric devices of various embodiments. Timing is selected to avoid premature inflation in the esophagus that could lead to an esophageal obstruction or belated inflation that could lead to intestinal obstruction.

Methods for verifying that the intragastric device is in the stomach are useful in that they do not rely on mere timing after administration of the intragastric device. Verification of location can be done with radiography. After a patient swallows an encapsulated balloon, radiography can be done to ensure the balloon is in the stomach after swallowing, with the encapsulated balloon visualized by a radio-opaque marker. Radiographic techniques include x-ray or fluoroscopy techniques that provide real-time images of the balloon using radiation. However, radiation may be harmful to the body if prolonged or administered in high doses. While fluoroscopy typically uses low doses of radiation, repeated use may create a risk of harm to a patient. Further, there is the risk of accidental administration of too high of a dose to a patient.

Electromagnetic-based systems and methods provide advantages over, e.g., radiography. Electromagnetism refers generally to the magnetic fields corresponding to electric currents. A current may be induced in a conducting material by the presence of a magnetic field. A magnetic field may also be induced by the presence of a current running through a conductive material. Electromagnetic radiation, energy propagated as electromagnetic waves, can include radio waves, microwaves, visible light, gamma rays, infrared radiation, ultraviolet radiation, an x-rays. Electromagnetism has been used in many different contexts, and it presents advantages when used in the intragastric device locating and characterizing context.

Voltage-based systems and methods also provide advantages over e.g., radiography. Voltages are created when the electric potential of one point is different from that of another point. Voltage has been used in many different contexts, and it presents advantages when used in the intragastric device locating and characterizing context.

U.S. Pat. No. 8,858,432, the contents of which are incorporated herein by reference in their entirety, discloses ingestible markers incorporating a signal generating circuit. The ingestible event marker systems include an ingestible event marker (IEM) and a personal signal receiver. The IEM includes an identifier, such as a physiologically acceptable carrier, that is activated upon contact with a target internal physiological site of a body, such as digestive tract internal target site. The personal signal receiver is configured to be associated with a physiological location, e.g., inside of or on the body, and to receive a signal the IEM. During use, the IEM broadcasts a signal which is received by the personal signal receiver.

U.S. Pat. No. 8,836,513, the contents of which are incorporated herein by reference in their entirety, describes a system having an ingestible product indicating that it has been consumed. The system includes a conductive element, an electronic component, and a partial power source in the form of dissimilar materials. Upon contact with a conducting fluid, a voltage potential is created and the power source is completed, which activates the system. The electronic component controls the conductance between the dissimilar materials to produce a unique current signature. The system can be associated with food and communicate data about ingestion of food material to a receiver.

U.S. Pat. No. 8,847,766, the contents of which are incorporated herein by reference in their entirety, describes a system for physical delivery of a pharmaceutical agent. The system includes an identifier that transmits a conductive signal and consumable electrodes formed of dissimilar materials. The electrodes are configured to both generate a voltage to energize the identifier and transmit the conductive signal to the body when the first and second electrodes contact the bodily fluid.

Ultrasound-based systems and methods also provide advantages over, e.g., radiography. Ultrasound is an oscillating sound pressure wave with a frequency greater than the upper limit of the human hearing range. Ultrasound is thus not separated from 'normal' (audible) sound based on differences in physical properties, only the fact that humans cannot hear it. Although this limit varies from person to person, it is approximately 20 kilohertz (20,000 hertz) in healthy, young adults. Ultrasound devices operate with frequencies from 20 kHz up to several gigahertz.

Ultrasonic devices may be used to detect objects and measure distances. Ultrasonic imaging (sonography) is used in both veterinary medicine and human medicine. In the nondestructive testing of products and structures, ultrasound is used to detect invisible flaws. Industrially, ultrasound is used for cleaning and for mixing, and to accelerate chemical processes. Animals such as bats and porpoises use ultrasound for locating prey and obstacles.

Ultrasonics is the application of ultrasound. Ultrasound can be used for medical imaging, detection, measurement and cleaning. At higher power levels, ultrasonics is useful for changing the chemical properties of substances.

Medical sonography (ultrasonography) is an ultrasound-based diagnostic medical imaging technique used to visualize muscles, tendons, and many internal organs, to capture their size, structure and any pathological lesions with real time tomographic images. Ultrasound has been used by radiologists and sonographers to image the human body for at least 50 years and has become a widely used diagnostic tool. The technology is relatively inexpensive and portable, especially when compared with other techniques, such as magnetic resonance imaging (MM) and computed tomography (CT). Ultrasound is also used to visualize fetuses during routine and emergency prenatal care. Such diagnostic applications used during pregnancy are referred to as obstetric sonography. As currently applied in the medical field, properly performed ultrasound poses no known risks to the patient. Sonography does not use ionizing radiation, and the power levels used for imaging are too low to cause adverse heating or pressure effects in tissue.

Ultrasound is also increasingly being used in trauma and first aid cases, with emergency ultrasound becoming a staple of most EMT response teams. Furthermore, ultrasound is used in remote diagnosis cases where teleconsultation is required, such as scientific experiments in space or mobile sports team diagnosis. Ultrasounds are also useful in the detection of pelvic abnormalities and can involve techniques known as abdominal (transabdominal) ultrasound, vaginal (transvaginal or endovaginal) ultrasound in women, and also rectal (transrectal) ultrasound in men.

Ultrasound has been used in many different contexts, and it presents advantages when used in the intragastric device locating and characterizing context.

Medical imaging is employed to diagnose a large number of diseases. The oldest method, dye X-ray technology, delivers high-resolution images within a short examination time; however, it has the disadvantage of exposing the patient to X-rays. Ultrasound imaging is a method of image acquisition that works without using radiation. With said ultrasound imaging, ultrasound signals are sent via an ultrasound transducer into the object to be examined and a corresponding control device receives the reflected ultrasound signals and processes the receive signals for imaging purposes.

U.S. Pat. No. 8,535,230, the contents of which are incorporated herein by reference in their entirety, describes an ultrasound device including an ultrasound transducer on a robotic arm to track an object as it moves. However, such a system is incompatible with tracking a device inside the body.

U.S. Pat. No. 8,105,247, the contents of which are incorporated herein by reference in their entirety, describes use of ultrasonic transceivers to measure the size of a gastric banding device. However, that system is intended for a stationary gastric banding device and is not directly applicable to locating and characterizing a translating, rotating and transforming intragastric device.

SUMMARY

There remains a need for a device and method of locating and characterizing in vivo an intragastric balloon device that is simple, cost effective, and/or avoids exposure to harmful radiation A free-floating or tethered intragastric volume-occupying device or devices that maintain volume and/or internal pressure within a predetermined range over time, or which undergoes a predetermined adjustment in volume and/or internal pressure over time, is disclosed. By maintaining a predetermined volume and/or internal pressure, stresses on the device leading to a breach in structural integrity can be minimized, which prevents premature and/or uncontrolled deflation or other device failure. By undergoing a predetermined adjustment in volume and/or internal pressure over time, a preselected volume profile can be obtained to accommodate changes in stomach size over the course of treatment with the device. The devices can be self-inflating (also referred to as automatic inflating) or inflatable (also referred to as manually inflating via a tether).

Volume-occupying devices and methods for manufacturing, deploying, inflating, tracking, locating, deflating and retrieving of such devices are provided. The devices and methods of the preferred embodiments may be employed for treating over weight and obese individuals. Methods employing the device of the preferred embodiments need not utilize invasive procedures, but rather the device may simply be swallowed by a patient, with or without a catheter attached. Once in the stomach of the patient, the device is inflated with a preselected fluid, e.g., a gas, liquid, vapor or mixtures thereof, to a preselected volume. Therefore, the use of one fluid, such as a "gas", e.g., an initial fill gas, to describe the various embodiments herein, does not preclude the use of other fluids as well. Further, a "fluid," such as an initial fill fluid, also includes a material or materials in the solid, liquid, vapor, or gas phase that are incorporated within, mixed within, carried within or otherwise entrained in a fluid such as a gas or liquid. A fluid can comprise one substance, or mixtures of different substances, and may be or include saline, physiologically acceptable fluids or substances, etc. as further described herein. The wall of the device is preselected for its particular fluid, e.g. gas, diffusion properties. Once in the in vivo environment, the gas(es) within the device diffuse out through the wall of the device, and gases diffuse into the device from the in vivo environment. By preselecting the device wall and gas(es) initially employed to inflate the device, taking into account diffusion properties of gases into the device from the in vivo environment, the volume and/or internal pressure of the device can be maintained within a preselected range, or can follow a preselected profile of volume and/or pressure changes. After a predetermined time period, the device can be removed using endoscopic tools or will decrease in volume or deflate so as to pass through the remainder of the patient's digestive tract.

Inflation may be achieved by use of a removable catheter that initially remains in fluid contact with the device after it has been swallowed by the patient. Alternatively, inflation may be achieved by a self-inflation process, e.g., generation of gas in the device once it reaches the stomach by reaction of gas-generating components contained within the device upon swallowing, or by introduction of one or more components in the gas generating process into the device by use of a removable catheter.

The volume-occupying subcomponent of devices may be formed by injection, blow or rotational molding of a flexible, gas-impermeable, biocompatible material, such as, for example, polyurethane, nylon or polyethylene terephthalate. Materials that may be used to control the gas permeability/impermeability of the volume-occupying subcomponent include, but are not limited to, silicon oxide (SiOx), gold or any noble metal, saran, conformal coatings and the like, when it is desired to reduce permeability. To enhance gas-impermeable characteristics of the wall of the device, if desirable, the volume-occupying subcomponent may be further coated with one or more gas-barrier compounds, or be formed of a Mylar polyester film coating or kelvalite, silver or aluminum as a metalized surface to provide a gas impermeable barrier.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

The devices incorporate a tracking or visualization component or components that enable physicians to determine the location and/or orientation and/or state of the device within the patient's body using electromagnetic, magnetic, voltaic, pH, optical, and/or acoustic (e.g., ultrasonic) methods. The tracking or visualization component can be the balloon or a component thereof or therein, or an additional component added to or affixed to the balloon or a component thereof or therein, or an additional component having a property indicative of placement of the balloon.

In some embodiments, tracking subcomponents may incorporate materials that emit electromagnetic energy. The device may be tracked and located using a complementary electromagnetic energy sensor that is responsive to the electromagnetic properties of the device. Such techniques may also be used to obtain certain device specific information and specifications while the device remains inside the patient's body, including but not limited to device location, orientation, size or state as it travels inside the body. The electromagnetic-responsive sensor outside the body can detect and process information related to the electromagnetic energy relayed by the internal device, which energy may be reflected off, created by, or otherwise propagated from the intragastric device or materials or objects in or on the intragastric device. This information can then be interpreted to identify the device's location, orientation, size and other attributes while still inside the body. An electromagnetic system provides a simple, non-invasive and less harmful method of tracking, locating and characterizing intragastric devices.

In some embodiments, tracking subcomponents may incorporate materials that emit visible light. The device may be tracked and located using a complementary optical sensor that is responsive to the radiation properties of the tracking subcomponents. Such techniques may also be used to obtain certain device specific information and specifications while the device remains inside the patient's body, including but not limited to device location, orientation, size or state as it travels inside the body. The optical sensor can detect and process information related to the light relayed by the intragastric device or materials or objects in or on the intragastric device, or materials associated with the intragastric device. This information can then be interpreted to identify the device's location, orientation, size and other attributes while still inside the body. An optical system for detecting visible light, provides a simple, non-invasive and less harmful method of tracking, locating, and characterizing intragastric devices. An optical system for detecting visible light can allow for tracking, locating, and characterizing intragastric devices without the need for medical imaging equipment, which can expensive, can require the use of trained technicians, and may not be readily available in all clinical settings.

In some embodiments, tracking subcomponents may incorporate materials that sense visible light from a light source that may be separate and apart from the intragastric device. The complementary light source may be present in, delivered to, or administered to, a known or determinable location in the body. The device may be tracked and located using an optical sensor in, on, or otherwise associated with the intragastric device that is responsive to the radiation properties of the complementary light source. Such techniques may also be used to obtain certain device specific information and specifications while the device remains inside the patient's body, including but not limited to device location, orientation, size or state as it travels inside the body. The optical sensor can detect and process information related to the light emitted from the complimentary light source. This information can then be interpreted to identify the location of the optical sensor with reference to the light source, and further to identify the location of the device's location based on the relative location of the optical sensor.

In some embodiments, an optical system or portions thereof may be combined with additional tracking subcomponents, such as an electromagnetic system, magnetic system, acoustic system, voltaic system, pH system or portions thereof. The combination of the systems or portions thereof may be implemented for further enhancing the locating and/or characterizing of the intragastric device in vivo.

Such techniques may also be used to obtain certain device specific information and specifications while the device remains inside the patient's body, including but not limited to device location, orientation, size or state as it travels inside the body. The magnetically-responsive sensor, e.g., a sensor outside of the body, can detect and relay information related to the magnetic field of the internal device. This information can then be interpreted to identify the device's location, orientation, size and other attributes while still inside the body. A light detecting system provides a simple, non-invasive and less harmful method of tracking, locating and characterizing intragastric devices.

In a first aspect, an optical system is provided for locating an intragastric device inside the body, the system comprising: an optical sensor configured to sense electromagnetic radiation, such as visible light; a swallowable light-emitting marker configured to produce electromagnetic radiation, such as visible light, in an in vivo gastric environment; and a valve system configured for introducing an initial fill fluid into a volume-occupying intragastric device when the intragastric device is in the in vivo gastric environment, the valve system comprising a swallowable catheter configured to releasably couple with the intragastric device.

In an embodiment of the first aspect, the system further includes a swallowable capsule.

In an embodiment of the first aspect, the light-emitting marker is configured to couple with the swallowable catheter.

In an embodiment of the first aspect, the light-emitting marker is configured to couple with a distal end of the swallowable catheter.

In an embodiment of the first aspect, the light-emitting marker is configured to couple with a swallowable capsule.

In an embodiment of the first aspect, the light-emitting marker is configured to couple with the intragastric device.

In an embodiment of the first aspect, the system further comprises a sensor interface unit configured to electrically communicate with the optical sensor.

In an embodiment of the first aspect, the system further comprises a system control unit configured to electrically communicate with the sensor interface unit and with the optical sensor.

In an embodiment of the first aspect, the system further comprises a computer configured to electrically communicate with the system control unit and to display an identifier indicating the location of the light-emitting marker inside the body.

In an embodiment of the first aspect, the system further comprises the intragastric device, wherein the intragastric device is a balloon.

In an embodiment of the first aspect, the system further comprises the initial fill fluid, wherein the intragastric device comprises a polymeric wall configured to have, under conditions of the in vivo gastric environment, a permeability to $CO_2$ of more than 10 cc/m$^2$/day, such that a rate and an amount of diffusion of $CO_2$ from the in vivo gastric environment into a lumen of the intragastric device through the polymeric wall is controlled, at least in part, by a concentration of an inert gas in the initial fill fluid.

In an embodiment of the first aspect, the polymeric wall comprises a $CO_2$ barrier material comprising an ethylene vinyl alcohol layer.

In an embodiment of the first aspect, the polymeric wall comprises a two layer $CO_2$ barrier material comprising a nylon layer and a polyethylene layer.

In an embodiment of the first aspect, the polymeric wall comprises a three layer $CO_2$ barrier material comprising a nylon layer, a polyvinylidene chloride layer, and a polyethylene layer.

In an embodiment of the first aspect, the polymeric wall comprises a three layer $CO_2$ barrier material comprising a nylon layer, an ethylene vinyl alcohol layer, and a polyethylene layer In an embodiment of the first aspect, the initial fill fluid consists essentially of gaseous $N_2$.

In an embodiment of the first aspect, the initial fill fluid consists essentially of gaseous $N_2$ and gaseous $CO_2$.

In an embodiment of the first aspect, the initial fill fluid consists essentially of gaseous $N_2$ and gaseous $CO_2$, and wherein the gaseous $N_2$ is excess in concentration to the gaseous $CO_2$ in the initial fill fluid.

In an embodiment of the first aspect, the initial fill fluid comprises $SF_6$ in one or more of liquid form, vapor form, or gaseous form.

In an embodiment of the first aspect, the initial fill fluid comprises gaseous $N_2$ and gaseous $SF_6$.

In an embodiment of the first aspect, the polymeric wall is configured to have, under conditions of an in vivo gastric environment, a permeability to $CO_2$ of more than 50 cc/m$^2$/day.

In a second aspect, a method is provided for locating an intragastric device inside the body of a patient, the method comprising: introducing into the body of the patient, via swallowing, the intragastric device comprising an uninflated gastric balloon, the intragastric device releasably coupled with a catheter; introducing into the body of the patient, via swallowing, a light-emitting marker configured to be sensed by an optical sensor; sensing the light emitted by the light-emitting marker with the optical sensor; and confirming a location of the uninflated gastric balloon inside the patient based on sensing the light emitted by the light-emitting marker.

In an embodiment of the second aspect, the location of the uninflated gastric balloon inside the patient is the patient's stomach.

In an embodiment of the second aspect, the method further comprises: introducing an initial fill fluid into a lumen of the uninflated gastric balloon through the catheter, the intragastric balloon comprising a polymeric wall configured to have, under conditions of an in vivo gastric environment, a permeability to $CO_2$ of more than 10 cc/m$^2$/day; and exposing the inflated intragastric balloon to the in vivo intragastric environment for a useful life of at least 30 days, wherein a rate and an amount of diffusion of $CO_2$ from the in vivo gastric environment into the lumen of the balloon through the polymeric wall is controlled, at least in part, by a concentration of an inert gas in an initial fill fluid.

In an embodiment of the second aspect, the polymeric wall comprises a three layer $CO_2$ barrier material comprising a nylon layer, a polyvinylidene chloride layer, and a polyethylene layer.

In an embodiment of the second aspect, the polymeric wall comprises a three layer $CO_2$ barrier material comprising a nylon layer, an ethylene vinyl alcohol layer, and a polyethylene layer.

In an embodiment of the second aspect, the polymeric wall comprises a two layer $CO_2$ barrier material comprising a nylon layer and a polyethylene layer.

In an embodiment of the second aspect, the polymeric wall comprises a $CO_2$ barrier material comprising an ethylene vinyl alcohol layer.

In an embodiment of the second aspect, the initial fill fluid consists essentially of gaseous $N_2$.

In an embodiment of the second aspect, the first gas consists essentially of gaseous $N_2$ and gaseous $CO_2$.

In an embodiment of the second aspect, the initial fill fluid consists essentially of gaseous $N_2$ and gaseous $CO_2$, and wherein the gaseous $N_2$ is excess in concentration to the gaseous $CO_2$ in the first gas.

In an embodiment of the second aspect, the initial fill fluid comprises $SF_6$ in one or more of liquid form, vapor form, or gaseous form.

In an embodiment of the second aspect, the initial fill fluid comprises gaseous $N_2$ and gaseous $SF_6$.

In an embodiment of the second aspect, the polymeric wall is configured to have, under conditions of an in vivo gastric environment, a permeability to $CO_2$ of more than 50 cc/m$^2$/day.

In an embodiment of the second aspect, confirming a location of the uninflated gastric balloon inside the patient based on sensing the light emitted by the light-emitting marker comprises displaying on a computer an identifier indicating the location of the light-emitting marker.

In an embodiment of the second aspect, the light-emitting marker is coupled with a swallowable capsule.

In an embodiment of the second aspect, the optical sensor is coupled with the intragastric device.

In a third aspect, an optical system for locating a volume-occupying intragastric device inside the body is provided, the system comprising: an optical sensor configured to sense electromagnetic radiation; a volume-occupying intragastric device, the volume-occupying intragastric device comprising an intragastric balloon having a polymeric wall, a lumen, and a valve system configured for introducing an initial fill fluid into the lumen of the intragastric balloon when the intragastric balloon is in an in vivo gastric environment, the valve system comprising a swallowable catheter configured to releasably couple with the volume-occupying intragastric device; and a swallowable light-emitting marker configured to produce electromagnetic radiation, in an in vivo gastric environment, indicative of a location of the volume-occupying intragastric device or a component associated therewith.

In an embodiment of the third aspect, the light-emitting marker is configured to couple with the swallowable catheter.

In an embodiment of the third aspect, the system further comprises a swallowable capsule configured to contain the intragastric balloon in an uninflated and compacted state, wherein the light-emitting marker is configured to couple with the volume-occupying intragastric device.

In an embodiment of the third aspect, the light-emitting marker is configured to couple with the volume-occupying intragastric device.

In an embodiment of the third aspect, the system further comprises a sensor interface unit configured to electrically communicate with the optical sensor.

In an embodiment of the third aspect, the system further comprises a system control unit configured to electrically communicate with the sensor interface unit and with the optical sensor.

In an embodiment of the third aspect, the system further comprises a computer configured to electrically communicate with the system control unit and to display an identifier indicating the location of the light-emitting marker inside the body.

In an embodiment of the third aspect, the system further comprises an initial fill fluid, wherein the polymeric wall is configured to have, under conditions of the in vivo gastric environment, a permeability to $CO_2$ of more than 10 $cc/m^2/$day, such that a rate and an amount of diffusion of $CO_2$ from the in vivo gastric environment into the lumen of the intragastric balloon through the polymeric wall is controlled, at least in part, by a concentration of an inert gas in the initial fill fluid.

In an embodiment of the third aspect, the polymeric wall comprises a layer selected from the group consisting of: a $CO_2$ barrier material comprising an ethylene vinyl alcohol layer, a two layer $CO_2$ barrier material comprising a nylon layer and a polyethylene layer, a three layer $CO_2$ barrier material comprising a nylon layer, a polyvinylidene chloride layer, and a polyethylene layer, and a three layer $CO_2$ barrier material comprising a nylon layer, an ethylene vinyl alcohol layer, and a polyethylene layer.

In an embodiment of the third aspect, the initial fill fluid comprises $SF_6$ in one or more of liquid form, vapor form, or gaseous form.

In an embodiment of the third aspect, the initial fill fluid comprises gaseous $N_2$ and gaseous $SF_6$.

In a fourth aspect, a method for optically locating a volume-occupying intragastric device inside a body of a patient is provided, the method comprising: introducing into the body of the patient, via swallowing, a volume-occupying intragastric device, the volume-occupying intragastric device releasably coupled with a catheter; introducing into the body of the patient, via swallowing, a light-emitting marker configured to be sensed by an optical sensor; sensing the light emitted by the light-emitting marker with the optical sensor; and confirming a location of the volume-occupying intragastric device inside the patient based on sensing the light emitted by the light-emitting marker.

In an embodiment of the fourth aspect, the volume-occupying intragastric device comprises an intragastric balloon in an uninflated state, and wherein the location of the intragastric balloon is inside the patient's stomach.

In an embodiment of the fourth aspect, wherein the volume-occupying intragastric device comprises an intragastric balloon having a polymeric wall and lumen, the method further comprises: introducing an initial fill fluid into the lumen of the intragastric balloon through the catheter so as to inflate the intragastric balloon, wherein the polymeric wall is configured to have, under conditions of an in vivo gastric environment, a permeability to $CO_2$ of more than 10 $cc/m^2/day$; and exposing the inflated intragastric balloon to the in vivo intragastric environment for a useful life of at least 30 days, wherein a rate and an amount of diffusion of $CO_2$ from the in vivo gastric environment into the lumen of the intragastric balloon through the polymeric wall is controlled, at least in part, by a concentration of an inert gas in an initial fill fluid.

In an embodiment of the fourth aspect, wherein the polymeric wall comprises a layer selected from the group consisting of: a $CO_2$ barrier material comprising an ethylene vinyl alcohol layer, a two layer $CO_2$ barrier material comprising a nylon layer and a polyethylene layer, a three layer $CO_2$ barrier material comprising a nylon layer, a polyvinylidene chloride layer, and a polyethylene layer, and a three layer $CO_2$ barrier material comprising a nylon layer, an ethylene vinyl alcohol layer, and a polyethylene layer.

In an embodiment of the fourth aspect, the initial fill fluid comprises $SF_6$ in one or more of liquid form, vapor form, or gaseous form.

In an embodiment of the fourth aspect, the initial fill fluid comprises gaseous $N_2$ and gaseous $SF_6$.

In an embodiment of the fourth aspect, the method further comprises displaying on a computer an identifier indicating the location of the light-emitting marker.

In an embodiment of the fourth aspect, the intragastric balloon is in an uninflated and compacted state inside a swallowable capsule, wherein the light-emitting marker is coupled with the capsule.

In an embodiment of the fourth aspect, the optical sensor is coupled with volume-occupying intragastric device.

Any of the aforementioned embodiments can be combined with other embodiments or with other aspects and associated embodiments. Similarly, any embodiment of any of the aspects can be employed in combination with one or more other embodiments of any of the aspects. Further, any or all of the embodiments may use a gas or liquid phase material as the "fluid." Thus, recitation of "gas" in any embodiment is not meant to limit it to just a gaseous material, but may also include liquid phase materials as well, as is described in further detail herein.

DETAILED DESCRIPTION OF THE PREFERRED EMBODIMENT

Figure 1:
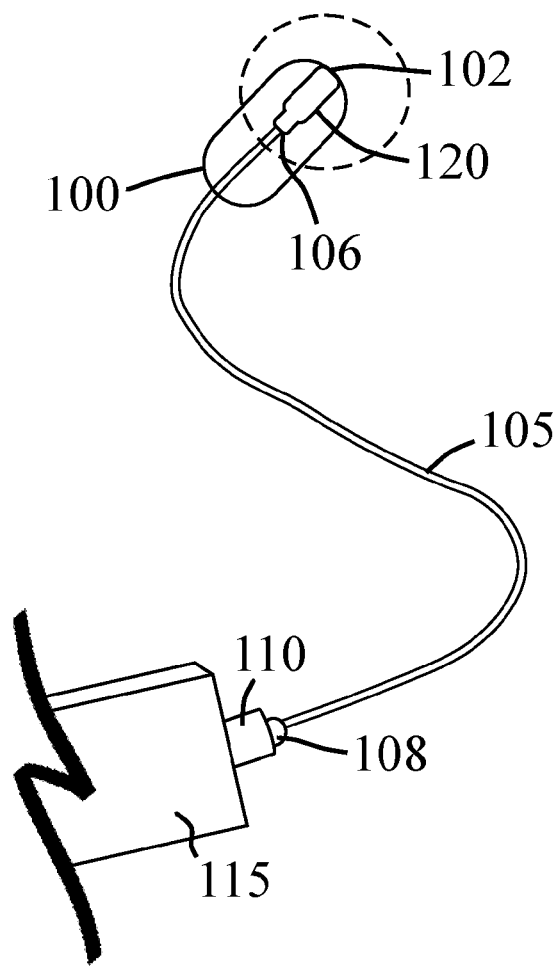
FIG. 1 illustrates an embodiment of a part of an optical location system for locating a light-emitting capsule.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes. Degradation after a predetermined time, or within a predetermined window of time, after ingestion is particularly preferred.

The term "$CO_2$ barrier material" as used herein is a broad term, and is to be given its ordinary and customary meaning to a person of ordinary skill in the art (and is not to be limited to a special or customized meaning), and refers without limitation to a material having a permeability to $CO_2$ of 10 cc/m$^2$/day or less under simulated in vivo conditions (100% humidity and body temperature of 37° C.). As used herein, the term "in vivo conditions" as used herein refers to both actual in vivo conditions, such as in vivo intragastric conditions, and simulated in vivo conditions. The permeability of a material to $CO_2$ may vary depending upon the conditions under which it is measured.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size, and the balloon material thickness. The system is preferably of a size less than the average normal esophagus diameter.

Described herein is a system for an orally ingestible device with magnetic, electromagnetic, optical and/or ultrasonic locating, tracking, and/or otherwise sensing of the device or state of the device. In preferred embodiments, the device is able to traverse the alimentary canal. The device may be useful, for example, as an intragastric volume-occupying device. In some embodiments, the device may be useful as a separate device for locating or tracking an intragastric volume-occupying device. The device overcomes one or more of the above-described problems and shortcomings found in current intragastric volume-occupying devices and intragastric volume-occupying device systems. While in certain embodiments specific devices are described, it is understood that the materials and methods can also be applied to other devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention. The various subcomponents for use in the presently disclosed magnetic, electromagnetic, optical, and ultrasonic systems may be discussed under their respective subheaded sections or in any other section, including any section or sections discussing various tracking and visualization subcomponents.

A swallowable, self-inflating or inflatable intragastric balloon system according to selected preferred embodiments includes the following components: self-sealing valve system for addition of fluid to the lumen of the balloon or to the inner container ("valve system"), a balloon in a deflated and compacted state ("balloon") and an outer capsule, container, or coating ("outer container") that contains the balloon. For self-inflating balloons, an inner capsule or other container ("inner container") that contains one or more $CO_2$ generating components is present inside the lumen of the balloon. The system may also include various components for facilitating delivery ("delivery components") of the balloon to the mouth and/or through the esophagus.

For inflatable balloons, an inflation fluid source, a catheter, and tubing ("inflation assembly") are provided for inflating the balloon after ingestion or placement in the stomach. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting a liquid activation agent into the lumen of the balloon via the self-sealing valve. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter or a physician-assisted catheter. The valve system serves to allow for balloon inflation using a miniature catheter that includes a needle assembly and also provides a mechanism for detachment of the catheter after inflation has been completed.

The outer container preferably incorporates the balloon in a compacted state (e.g., folded and rolled), preferably with sufficient space to allow for activation liquid to be injected into the balloon in the self-inflating balloon configuration, wherein the liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure. In the inflatable balloon configuration, the outer container need only incorporate the balloon in a compacted state.

Selected components of a swallowable intragastric balloon system of a preferred embodiment can include a silicone head with radioopacity ring, trimmed 30 D silicone septum, Nylon 6 inoculation spacer, compacted balloon, inner container (if self-inflating), and outer container as constituents of the system in unassembled form. A fully assembled outer container can include a vent hole aligned with a septum for puncture to inject liquid activation agent (if self-inflating) or a port for connection of tubing (if inflatable). As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to inflation.

Inner Container

In order to initiate inflation in the self-inflating configuration, the inflation subcomponent may require outside inputs such as an activation agent. The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

In one embodiment, prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is are creased similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed inside the outer container.

In a self-inflating configuration, the balloon is folded so as to form a pocket around the inner capsule, to insure that the liquid injected through the self-sealing valve system is contained in an area less than 10% of the entire balloon surface area. It is not necessary to provide a pocket in the inflatable configuration, as no inner capsule is provided. The balloon is folded such that the number of total folds is minimized so as to minimize possible damage to the outer material or compromise of barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

In the self-inflating configuration, the material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

In a self-inflating configuration, an inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard push-fit gelatin capsule but a gelatin tape may be used in lieu of a push-fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that can block the esophageal passageway or prematurely pass through the pyloric sphincter. Timing is also controlled by compacting the balloon such that the activation agent is substantially localized in the balloon next to the inner capsule, creating an efficient $CO_2$ self-inflation method. Balloon inflation is initiated by the liquid activation agent causing degradation of the inner container, such that the inflation agent in the inner container contacts the liquid activation agent, thereby initiating the gas generation reaction.

The inner container for the self-inflating balloon is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 cm$^3$ of $CO_2$ at nominal pressure.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container is preferably from about 1.2 ml to about 8.25 ml. In the self-inflating configuration, the outer container is preferably configured with one or more holes, slits, passageways or other egresses, preferably on each end, which act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. Such egresses can also expedite dissolution of the outer container to prepare the balloon for inflation in the inflatable configuration. The process of the outer capsule degrading (e.g., separates, dissolves, or otherwise opens) is expedited by pressure build up caused by inflation (self-inflation or inflation via catheter) of the balloon. The outer capsule can be dipped in water for a brief time to soften the materials but not release the balloon prior to swallowing to minimize the time lapse between swallowing and balloon inflation. In the inflatable configuration, the outer container is provided with a hole to house the inflation tube needle assembly, wherein the diameter of the catheter needle housing is mechanically compatible with the diameter of the outer container hole such that the needle can be inserted into the self-sealing valve while maintaining therein the housed balloon to facilitate pushing or swallowing of the balloon assembly. In a preferred embodiment, the outer container is a capsule. The distal half of the capsule may be flared to prevent abrasion of the balloon materials by the leading edge of the capsule as the compacted balloon is inserted into the capsule. The capsule can also comprise two parts held together with a gel band and encompassing the folded balloon that allows for quicker separation of the capsule so that inflation can take place more expeditiously. The outer capsule degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device is fitted into a standard sized gelatin capsule. The capsule may be formed of a material that has a known rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon cannot be easy, as objects more than 7 mm in diameter do not readily pass.

Delivery Components

It certain embodiments, it may advantageous for an administrator of the device to use a delivery tool for delivering the device to the mouth or facilitating its passage through the esophagus in the optimal orientation. A delivery tool may enable the device administrator to inject the device with one or more inflation agents or inflation gases as part of administering the device to the patient. In a preferred embodiment, such injection may be accomplished in the same mechanical action(s) of the administrator that are employed to release the device from the delivery tool into the mouth or esophagus. For example, the delivery tool may include a plunger, a reservoir containing a fluid, and an injection needle. The administrator pushes the plunger which, either in sequence or approximately simultaneously, forces the injection needle into the device and thereby injects the liquid contained in reservoir into the device. Subsequent application of force to the plunger pushes the device out of the delivery tool and into the desired location within the patient. Furthermore, the delivery tool may also include a subcomponent that administers an anesthetic or lubricant into the patient's mouth or esophagus to ease the swallowability of the device.

Balloon

The volume-occupying subcomponent ("balloon") of the preferred embodiments is generally formed of a flexible material forming a wall which defines an exterior surface and an interior cavity. Various of the above-described subcomponents may be either incorporated into the wall or interior cavity of the volume-occupying subcomponent. The volume-occupying subcomponent can vary in size and shape according to the patient's internal dimensions and the desired outcome. The volume-occupying subcomponent may be engineered to be semi-compliant, allowing the volume-occupying subcomponent to stretch or expand with increases in pressure and/or temperature. Alternatively, in some embodiments, a compliant wall offering little resistance to increases in volume may be desirable.

Spherical volume-occupying subcomponents are preferred in certain embodiments. Alternatively, the volume-occupying subcomponent may be constructed to be donut-shaped, with a hole in the middle of it, and may be weighted and shaped in such a way that it orients in the stomach to cover all or part of the pyloric sphincter, similar to a check valve. The hole in the middle of the volume-occupying subcomponent can then serve as the primary passage for the contents of the stomach to enter the small intestine, limiting the passage of food out of the stomach and inducing satiety by reducing gastric emptying. Volume-occupying subcomponents may be manufactured with different-sized donut-holes according to the degree that gastric emptying is desired to be reduced. Delivery, inflation and deflation of the volume-occupying subcomponent may be accomplished by any of the methods described above.

It is advantageous for the volume-occupying subcomponent wall to be both high in strength and thin, so as to minimize the compacted volume of the device as it travels the esophagus of the patient. In certain embodiments, the volume-occupying subcomponent wall materials are manufactured with a biaxial orientation that imparts a high modulus value to the volume-occupying subcomponent.

In one embodiment, the volume-occupying subcomponent is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Tables 1a-b.

In certain preferred embodiments, the volume-occupying subcomponent is injection, blow or rotational molded. Either immediately following such molding, or after a period of curing, the gas-barrier coating may be applied if not already applied within the composite wall.

In another embodiment, the intragastric volume-occupying subcomponent is formed using a Mylar polyester film coating silver, aluminum or kelvalite as a metalized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying sub component.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

Deflation and/or inflation of the volume-occupying subcomponent may be achieved through one or more injection sites within the wall of the volume-occupying subcomponent. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S. Patent Publication No. 2010-0100116-A1, the contents of which is hereby incorporated by reference in its entirety. The materials are able to contain a fluid, preferably in compressed or non-compressed gas form, such as, e.g., $N_2$, Ar, $O_2$, $CO_2$, or mixture(s) thereof, or atmospheric air (composed of a mixture of $N_2$, $O_2$, Ar, $CO_2$, Ne, $CH_4$, He, Kr, $H_2$, and Xe) that simulate gastric space concentrations. In certain embodiments, the balloon is able to hold the fluid (gas) and maintain an acceptable volume for up to 6 months, preferably for at least 1 to 3 months after inflation. Particularly preferred fill gases include non-polar, large molecule gases that can be compressed for delivery.

Prior to placement in the outer container, the balloon is deflated and folded. In the inverted configuration in a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it is placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

In a preferred embodiment, a self-inflating balloon is fully sealed 360 degrees around. In the self-inflating configuration, with injection of an inflation agent by needle syringe, there are preferably no external openings or orifices to the central lumen. In the inflatable configuration, a valve structure (either protruding, recessed, or flush with the surface of the balloon) is provided for providing an inflation fluid to the central lumen. The balloon can have a "noninverted," "inverted," or "overlapped" configuration. In a "noninverted" configuration, the seams or welds and seam allowance, if any, are on the outside of the inflated balloon. In an "overlapped" configuration, layers are overlapped, optionally with one or more folds, and secured to each other via welds, a seam, adhesive, or the like, resulting in a smooth external surface. In an "inverted" configuration, the balloon has a smooth external surface with seams, welds, adhesive bead, or the like inside the inflated balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain fluid in the balloon.

The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 $cm^3$ to 350 $cm^3$ (at 37° C. and at internal nominal pressure and/or full inflation), an internal nominal pressure (at 37° C.) of 0 psi (0 Pa) to 15 psi (103421 Pa), and a weight of less than 15 g. The self-inflating balloon is configured for self-inflation with $CO_2$ and is configured to retain more than 75% of the original nominal volume for at least 25 days, preferably for at least 90 days when residing in the stomach. The inflatable balloon is configured for inflation with an appropriate mixture of gases so as to deliver a preselected volume profile over a preselected time period (including one or more of volume increase periods, volume decrease periods, or steady state volume periods).

In certain embodiments wherein a stable volume over the useful life of the device is preferred, the balloon is configured to maintain a volume of at least 90% to 110% of its original nominal volume. In other embodiments, it can be desirable for the balloon to increase and/or decrease in volume over its useful life (e.g., in a linear fashion, in a stepwise fashion, or in another non-linear fashion). In other embodiments, the balloon maintains a volume of 75% to 125% of its original nominal volume, or 75% to 150%

The intragastric device can be a single free-floating or tethered device. In some embodiments, it can be desirable to provide multiple devices (2, 3, 4, 5, 6, or more), either free-floating or tethered to each other, e.g., in a similar configuration to a cluster of grapes. The individual devices can be simultaneously inflated with one inflation system connected to all of the devices, or each device can be provided with a separate inflation system.

Valve System

In preferred embodiments, a self-sealing valve system which contains a self-sealing septum housed within a metallic concentric cylinder is provided. In the inflatable configuration, the self-sealing valve system is preferably adhered to the underside of the balloon material such that only a portion of the valve protrudes slightly outside of the balloon surface to ensure a smooth surface. The valve system for the inflatable configuration can utilize the same self-sealing septum designed for the self-inflating configuration. The septum preferably consists of a material possessing a durometer of 20 Shore A to 60 Shore D. The septum is inserted or otherwise fabricated into the smaller cylinder of the concentric metallic retaining structure that is preferably cylindrical in shape. The smaller cylinder within the larger cylinder controls alignment of the catheter needle sleeve/needle assembly with the septum, provides a hard barrier so that the catheter needle does not pierce the balloon material (needle stop mechanism), and provides compression such that the valve/septum re-seals after inflation and subsequent needle withdrawal.

The concentric valve system can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

The septum is preferably cone shaped, so that the compressive forces are maximized for self-sealing after inflation. The self-sealing septum allows air to be evacuated from the balloon for processing/compacting and insertion into the outer container, and allows for piercing by an inflation agent syringe needle (self-inflating configuration) or inflation catheter needle (inflatable configuration), and then subsequent withdrawal of the inflation agent syringe needle or detachment of the inflation catheter and withdrawal of the catheter needle significantly limiting gas leakage outside of the balloon during the inflation process and needle withdrawal/catheter detachment. The septum is inserted into the valve using a mechanical fit mechanism to provide compression. An additional ring can be placed at the distal end of the inner cylinder to provide additional compression to ensure the septum material is dense enough to re-seal itself. The ring is preferably metallic in nature, but can also be a non-metallic polymeric material such as an acrylic, epoxy, or thermoplastic elastomer or thermoplastic polyurethane. The ring material is preferably the same material as the cylinder, titanium, but can also be gold, stainless steel, MP35N or the like.

In the inflatable configuration, a larger, outer cylinder of the concentric valve housing contains a slightly harder durometer material than the inner cylinder (50 Shore A or greater), but is also preferably silicone. The purpose of using a harder durometer material is to ensure sealing when connected to the needle sleeve for inflation. The silicone located in the outer ring of the concentric valve is adhered to the balloon from the inside surface. The entire outer cylinder is filled and a small circular lip of this same material is provided that is slightly larger than the diameter of the inner cylinder and extends to the outside surface of the balloon. The lip is compatible with the bell shaped needle sleeve and provides sealing to enhance connection of the valve to the catheter to withstand the inflation pressures applied and also increases the tensile force of the catheter. This silicone lip preferably does not protrude past the balloon surface more than 2 mm to ensure that the balloon surface remains relatively smooth and does not cause abrasion or ulcerations of the mucosa. It is designed to provide compressive forces against the needle sleeve of the catheter for inflation and detachment whereby when connected to the needle sleeve of the inflation catheters, the connection force during the inflation process can withstand up to 35 PSI. The seal is then broken during detachment using hydrostatic pressure that is more than 40 PSI less than 200 PSI to break the connection force. Two additional retaining rings, preferably made of the same material as concentric valve, are included in the valve system to further enhance the seal between the metal and the valve silicone and provide additional mechanical support to ensure proper mechanical fit and are intended to disrupt slippage of the silicone material from the hard (metallic) valve system (causing an increase in tensile force).

The valve structure for the inflatable configuration uses a mechanical fit mechanism to provide the functions of the self-sealable valve for inflation by the catheter and subsequent catheter detachment; however, primer and/or adhesive may be used to provide additional support in maintaining the assembly. The configuration can be modified by modifying the surfaces of the metal components, making them more sticky or slippery to provide the desired mechanical/interference fit. The interference fit between the valve and the catheter can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

The total valve diameter in the inflatable configuration is designed to fit a miniature catheter system that does not exceed 8 French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve so as to maintain the volume of the deflated/folded balloon (and thus the outer container dimensions) as small as possible. The valve system is preferably attached to the inner surface of the balloon such that a shear force greater than 9 lbs (40 N) is required to dislodge the valve system.

In a self-inflating configuration, the valve system can be attached to the balloon (e.g., on its inside surface) without the use of an opening, orifice, or other conduit in the wall of the balloon. The valve system can utilize a septum with a durometer of 20 Shore A to 60 Shore D. The valve can be inserted or otherwise fabricated into a retaining structure that has a higher durometer, e.g., 40 Shore D to 70 Shore D or more. The retaining structure can be fabricated from a silicone, rubber, soft plastic or any suitable non-metallic polymeric material such as an acrylic, an epoxy, a thermoplastic elastomer, or thermoplastic polyurethane. Preferably, a structure, such as a ring, that can be metallic or non-metallic but radioopaque (e.g., barium) and visible under X-ray, or magnetic or magnetizable and detectable by sensing of a magnetic field, can be embedded in the retaining structure. Using a mechanical fit mechanism of two structures of different durometers, one softer (septum) with a large diameter, can be inserted into a snug, more rigid durometer structure creates compressive forces in the once open orifice to enable $CO_2$ retention and reduce susceptibility for $CO_2$ gas leaks. The metallic ring for radio-opacity also helps to create compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to maintain the volume of the deflated/folded balloon (and thus the outer capsule) as small as possible. The valve system is preferably attached to the inner surface of the balloon such that a shear force greater than 9 lbs (40 N) is required to dislodge the valve system. A silicone head and opacity ring of a self-sealing valve system can be employed, as can a wedge-shaped septum.

In the self-inflating configuration, an inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can be employed in preferred embodiments.

Inflation Assembly

In certain preferred embodiments, the volume-occupying subcomponent is filled with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, nitrogen, $SF_6$, other gas(es), vapors, saline solution, pure water, a liquid or vapor under external ambient conditions (e.g., room temperature) that forms a vapor or gas, respectively, at in vivo temperatures (e.g., $SF_6$), or the like, into the volume-occupying subcomponent and thereby inflate it. The fluid may be or include a variety of other fluid or non-fluid materials as well, including physiologically acceptable fluids, such as aqueous fluids, e.g., water, water with one or more additives (e.g., electrolytes, nutrients, flavorants, colorants, sodium chloride, glucose, etc.), saline solution, or the like. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled. Current technology allows for a self-inflating intragastric volume-occupying subcomponent which generally begins to inflate in a four minute timeframe after injection with an activation agent such as citric acid. In this approach, the volume-occupying subcomponent may, in some instances, begin to inflate prior to residing within the stomach (e.g., in the esophagus), or, in patients with gastric dumping syndrome or rapid gastric emptying, the volume-occupying subcomponent may end up in the small intestine prior to the time that inflation occurs. Accordingly, in certain embodiments it can be desirable to inflate the volume-occupying subcomponent on command, once it is ascertained that the volume-occupying subcomponent is residing in the correct location.

In certain embodiments, it may also be advantageous for the volume-occupying subcomponent to inflate gradually or in several steps over time, or for the volume-occupying subcomponent to maintain a volume and/or internal pressure within a preselected range. For example, if gas escapes the volume-occupying subcomponent prior to the desired deflation time, it can be beneficial for the device to re-inflate in order to preserve it in its expanded state.

An intragastric balloon system that is manually inflated by a miniature catheter can be employed in certain embodiments. The system preferably remains "swallowable." The balloon for delivery is in a compacted state and is attached to a flexible, miniature catheter, preferably no larger than 4 French (1.35 mm) in diameter. The catheter is designed such that a portion of the catheter can be bundled or wrapped upon itself for delivery with the encapsulated balloon, allowing the patient to swallow both catheter and balloon for delivery to the stomach. The balloon can contain a self-sealable valve system for attachment of the catheter and inflation of the balloon once it reaches the stomach cavity. The proximal end of the catheter can be left just outside of the patient's mouth, permitting connection to an inflation fluid container that can house the preferred inflation fluid (gas or liquid). After inflation the catheter can be detached from the balloon valve and pulled back through the mouth. This method allows for the intragastric balloon to maintain its swallowability but allow for inflation by a fluid source or a mixture of fluid sources via the catheter. Alternatively, a more rigid, pushable system can be employed wherein the balloon valve is compatible with either the swallowable, flexible catheter or the pushable, rigid catheter assembly.

The inflation catheters (swallowable or administrator-assisted pushable) described herein are configured to deliver the balloon device orally and without any additional tools. The administration procedure does not require conscious sedation or other similar sedation procedures or require endoscopy tools for delivery. However, other versions of the device can be used in conjunction with endoscopy tools for visualization or can be adapted such that the balloon device can be delivered nasogastrically as well.

In operation, the proximal end of the inflation catheter is connected to a valve or connector that allows for connection to the inflation source or the disconnect source, this is preferably a Y-arm connector or inflation valve. The connector materials may consist of polycarbonate or the like and can connect to a single or multi-lumen catheter tube. The distal end of the inflation catheter is connected to the universal balloon valve of the balloon that has been compacted and housed within a gelatin capsule or compacted using gelatin bands. The catheter tube is preferably from 1 French (0.33 mm) to 6 French (2 mm) in diameter. The catheter is preferably long enough to extend out past the mouth (connected to the inflation connector or valve) and transverse the esophagus down to at least the middle of the stomach—approximately 50-60 cm. Measurement ticks can be added to the tubing or catheter to aid in identifying where the end of the tube is located. Timing for inflation can be initiated by having the tube contain a pH sensor that determines a location difference between the esophagus (pH 5-7) and the stomach (pH 1-4) based on the different pH between the two anatomical sources, or can be derived or verified from the expected pressure in a contained (i.e., esophagus) versus a less-constrained space (i.e., stomach). The tube can also contain nitinol that has a tunable transmission to the body temperature, taking into account the timing for swallowing. The tube can also be connected to a series of encapsulated or compacted balloons on a single catheter. Each can be inflated and released separately. The number of balloons released can be tune-able to the patient's needs and desired weight loss. In certain embodiments, the intragastric balloon or catheter is located or tracked in the body by sensing a magnetic field of a magnetizable component of both or either devices, as discussed in detail below.

In certain embodiments, a catheter with the balloon at the distal end (inflated with air) is employed to temporarily and firmly hold the balloon in place. A small deflated balloon catheter can be positioned through the head of the gastric balloon (e.g., a "balloon within the balloon"), and then inflated with air during delivery to firmly hold the capsule and balloon in place and prevent spontaneous detachment of balloon from the catheter. This balloon catheter can incorporate a dual channel that can also allow the bigger gastric balloon to be inflated (by gas or liquid). Once the gastric balloon has been satisfactorily inflated, the small air balloon catheter can be deflated and pulled out of the valve (allowing the valve to self seal), and out of the body, leaving the inflated gastric balloon in the stomach.

In other embodiments, the catheter may be coated to enhance swallowability or is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Dual Lumen Catheter

In a preferred embodiment, a swallowable dual lumen catheter is provided. The dual lumen catheter has two lumens with a diameter of the complete assembly no larger than 5 French (1.67 mm), preferably no larger than 4 French (1.35 mm). The inner lumen preferably does not exceed 3 French (1 mm) and functions as the inflation tube, and the outer lumen preferably does not exceed 5 French (1.67 mm) and functions as the disconnection tube; the inner and outer lumen do not exceed 2 French (0.66 mm) and 4 French (1.35 mm), in diameter, respectively. The catheter assembly is connected to a needle assembly, described in more detail below, at the distal end and to a dual port inflation connector at the proximal end. The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and have moderate tensile strength and a significant amount of hoop strength to handle applied pressures. The lumens are preferably round and co-axial and free-floating so as to provide flexibility. The dual lumen assembly also preferably requires no adhesive or glue. Alternative lumen configurations can include two D-lumens or a combination of a D-lumen and round lumen, and can be used in stiffer configurations of the final catheter assembly. Preferred materials for the tubing include a thermo-resistant polyethylene tubing such as PEBAX® or a thermo-resistant polyurethane tubing such as PELLETHANE™, PEEK or Nylon. The tubing can also be manufactured out of bioresorbable materials such as polylactic acid (PLA), poly-L-aspartic acid (PLAA), polylactic/glycolic acid (PLG), poly-caprolactone (PCL), DL-lactide-co-ε-caprolactone (DL-PLCL) or the like, wherein the tube can be released after inflation and detachment and swallowed as normal.

At the distal end of the catheter assembly, the inner lumen or inflation tube is attached to the needle assembly that is used to puncture the balloon's self-sealing valve, preferably located at one of the apexes of the balloon housed inside of a gelatin capsule as outer container. The outer lumen is connected to the needle sleeve and provides connection force between the catheter assembly and balloon providing the tensile strength to withstand balloon inflation pressures, e.g., pressures of up to 10 psi or higher, while maintaining the assembly together. The needle sleeve is configured to mechanically couple with the balloon valve assembly. The needle is preferably made of metal, preferably stainless steel or the like, with a maximum size of 25 gauge (0.455 mm), preferably no smaller than 30 gauge (0.255 mm) for inflation timing purposes. The needle sleeve is preferably a soft material such as nylon or the like, or can also be polycarbonate, polyethylene, PEEK, ABS or PVC. The needle sleeve covers the length of the needle in its entirety, such that the body is protected from the needle and the needle can only pierce the balloon septum. Preferably the needle sleeve is flush or extends out slightly more than the needle length. The needle is inserted into the balloon septum prior to swallowing and maintains a retention force of approximately 0.33 lb (0.15 kg) when coupled to the silicone area of the balloon valve. The needle sleeve is preferably slightly bell shaped or contains a circular relief or lip so that when inserted into the silicone area of the valve a lock and key mechanism is created to increase the tensile strength of the assembly and enhance the sealing for inflation.

At the proximal end, the catheter assembly is connected to a Y-adapter assembly preferably made of polycarbonate. The y-adapter is "keyed" so that the inflation gas and connection fluid are connected to the catheter assembly appropriately and travel down the correct lumen.

Prior to inflation, priming of the disconnection lumen may be employed using a liquid. For example, the outer lumen is first flushed with 2 cc of water, saline, DI water or the like prior to balloon inflation. Thereafter, the inflation source container is attached to the connector leading to the inner lumen. The inflation source container works on the premise of the ideal gas law and a pressure decay model. For a given compressed gas formulation, the device is designed to equalize such that a higher starting pressure is used to inflate the balloon than is the resulting end pressure of the balloon. The starting pressure and volume are dependent upon the gas formulation selected, as well as the length of the catheter and the starting temperature (typically ambient temperature) and ending temperature (typically body temperature).

After inflation, the balloon is detached from the catheter assembly using hydraulic pressure. A syringe filled with water, DI water, or preferably saline is attached to the female end of the Y-assembly. The syringe contains 2 cc of liquid and when the syringe plunger is pushed in, enough hydraulic pressure is exerted such that the needle is ejected from the balloon valve.

Single Lumen Catheter

To further reduce the diameter of the inflation catheter, thereby increasing swallowability comfort, a single lumen catheter can be employed that does not exceed 2 French (0.66 mm) in diameter.

The needle/needle sleeve assembly is similar in design to that of the dual lumen catheter described herein. However, with the single lumen system, the distal end of the catheter lumen connects to the needle sleeve only and there is no second catheter inside. Instead, a single thread attached to a needle hub runs co-axially the length of the catheter to aid in tensile strength for detachment and overall flexibility.

The needle sleeve is slightly bell shaped or contains a circular relief or lip so that when inserted into the silicone area of the valve a lock and key mechanism is created to increase the tensile strength of the assembly, enhance the sealing for inflation, and since this is a single lumen assembly, the lip increases the force required to remove the needle from the valve so this does not occur haphazardly during the inflation process.

The proximal end of the catheter is connected to a 3-way valve and uses a method of exclusion for inflation and detachment of the balloon. The distal end of the catheter contains the needle sleeve, which is made of nylon or other similar source. The needle is metallic and preferably stainless steel.

The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible, preferably co-axial, and resistant to necking or buckling or kinking. For a single lumen system, the catheter tubing is preferably made of PEBAX®, but can also comprise bioresorbable materials such as PLA, PLAA, PLG, PCL, DL-PLCL or the like, wherein the tube can be released after inflation and detachment and swallowed as normal. The wire inside the catheter tubing attached to the needle is preferably a nylon monofilament, but Kevlar or nitinol wire or other suitable materials can also be used.

To inflate the balloon, the distal end of the catheter is attached to the balloon capsule where the needle protrudes through the self-sealable valve. The container is swallowed and a portion of the inflation catheter remains outside of the mouth. The inflation source container is connected to the proximal 3-way valve, where the port for inflation gas is chosen by excluding the other ports. The inflation fluid (preferably compressed nitrogen gas or a mixture of gases) travels down the single catheter lumen, whereby the inflation gas selects the path of least resistance, or more specifically through the needle cavity and into the balloon. The balloon is preferably inflated in less than 3 minutes.

To detach and withdraw the needle from the balloon valve, 2 cc or other suitable volume of water or other liquid is injected into the catheter at a high pressure. Since water has a high surface tension and viscosity, it occludes the needle pathway and the pressure is transferred to the outside needle sleeve, thereby breaking the fit between the needle sleeve and the balloon valve.

If it is desired to place a substance inside the balloon, such as water or acid or any alternative liquid, it can be done by using a lower pressure to inject the liquid.

Miniature Stiff-Bodied Inflation Catheter

In certain embodiments, a stiff-bodied inflation catheter can be employed, which can be placed orally or transnasally. This system can be from 1 French (0.33 mm) to 10 French (3.3 mm), preferably 8 French (2.7 mm) in diameter. A larger diameter is typically preferred to enhance pushability, with wall thickness also contributing to pushability and kink resistance. The length of the tube can be approximately 50-60 cm. As discussed above, measurement ticks can be added to the tubing to identify where the end of the tube is located, or a pH or pressure sensor on the catheter can be employed to detect location of the balloon.

This system for inflation/detachment is similar to the dual lumen system described above, but with a larger needle sleeve to accommodate the larger diameter tube. Materials that can be used in the lumen include, e.g., expanded polytetrafluoroethylene (EPTFE) for the outer lumen and polyetheretherketone (PEEK) for the inner lumen. To also enhance pushability, a strain relief device can be added to the distal and proximal ends. It is particularly preferred to have strain relief at the distal end, e.g., 1 to 8 inches, preferably 6 inches, to ensure the catheter bypasses the larynx and follows into the esophagus. The proximal end can have strain relief as well, e.g., to ensure fit of the Y-arm. The preferred material for the strain relief is a polyolefin. The method for inflation/detachment is the same method as for the dual lumen configuration where the outer lumen connects to the needle sleeve and the inner lumen connects to the needle. As part of the procedure, the patient can swallow water or other suitable liquid so as to distend esophageal tissue for smooth passage down of the device. Patients can also be administered an anesthetic at the back of the throat to numb the area and lessen the gag reflex.

The tube can also be connected to a series of encapsulated or compacted balloons on a single catheter such that a total volume of up to 1000 cc or more can be administered, as necessary. Each can be inflated and released separately. The number of balloons released can be tunable to the patient's needs and desired weight loss.

In addition, a catheter can be used for administering a gastric balloon that is similar to balloon catheters used in angioplasty termed "over-the-wire" or rapid exchange catheters. In this case where the patients attempts to swallow the catheter but fails so the stiff catheter—or physician assisted catheter can slide over the flexible catheter and the balloon can be pushed down in the same manner as the physician-assisted catheter. Different materials can be used to provide the varying degrees of flexibility or one material that is fabricated with different diameters across the length to vary the degree of stiffness can be used.

The swallowable self-inflating balloon construction method and the swallowable inflation tube construction method both remove the requirement for endoscopy to place the balloon and make the balloon administration process less invasive. This also allows for the total volume to be placed in a patient to be "titratable," or adjustable. When a balloon is placed for 30 days, a patient may report that over time they lose their feeling of fullness without eating. To compensate, another balloon can be placed easily without sedation and endoscopy. When a non-deflatable balloon is to be removed endoscopically, it is desirable to color-code the balloon composite walls with different colors so that the physician has a visual marker for removing the balloon at the end of its useful life while keeping the balloon that has remaining useful life in the patient's stomach.

In addition, the balloon wall can be marked approximately 180° from the self-sealing valve such that when the balloon is punctured endoscopically it folds more efficiently on itself so as to facilitate removal of the thin-walled structure without causing esophageal perforations and/or other damage by the balloon due to its shape, stiffness, and/or thickness of the wall material.

Inflation Fluid Container

The inflation fluid container is employed to control the amount or volume of fluid placed inside of the balloon. This can be in the form of a canister of, e.g., PVC, stainless steel, or other suitable material. The container can also be in syringe form. The materials employed are able contain a fluid, preferably in gas form, e.g., compressed or non-compressed $N_2$, Ar, $O_2$, $CO_2$, or mixture(s) thereof, or compressed or non-compressed atmospheric air (a mixture of $N_2$, $O_2$, Ar, $CO_2$, Ne, $CH_4$, He, Kr, $H_2$, and Xe). The balloon composite wall materials and respective diffusion gradients and gas permeability characteristics are used to select a fluid for inflation of the intragastric balloon, so as to provide a desired volume profile over time for the inflated balloon. The inflation fluid container materials are selected to ensure no or minimal diffusion or leakage of the fluid before it is connected to the y-arm connector or valve of the inflation catheter. The inflation fluid container preferably incorporates a pressure gauge and a connector. It can also contain a smart chip that notifies the healthcare professional of whether inflation is successful or if the balloon should be detached due to an error in the system.

To maintain "swallowability" of the balloon and to ensure comfort of the patient during the procedure, it is preferred to minimize the amount of time the catheter is placed in the mouth/esophagus. Timing of inflation is can be selected so as to minimize time in place. The outer container-catheter assembly, once swallowed, takes approximately 4-8 seconds to reach the stomach. Once in the stomach, the Inflation source container can be attached to the valve or port of catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where temperature is controlled inside the inflation source container to match that of the body. It is desired to have an inflation time after swallow of less than 5 minutes, and preferably 2-3 minutes, before balloon detachment and catheter withdrawal. The inputs use to derive inflation of the balloon (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a 2 French catheter system requires a higher starting pressure to achieve the same target balloon volume and pressure in the same time frame, assuming use of the same compressed gas formulation. In general, it is understood that starting with a higher pressure with the same flow rate/volume can decrease the inflation time.

The inflation source container provides feedback to the end user based on a pressure decay system. Where there is an expected starting pressure and expected ending pressure to indicate whether the balloon is inflated properly, there is no need for endoscopic visualization. Each scenario of expected pressure outputs can have its own tolerances around it to reduce possibilities of false positives, and the inflation fluid container can provide feedback based on these tolerances as to the status of balloon inflation and detachment. This is derived based on the Ideal Gas Law, where there is an expected end pressure based on the fixed volume of the balloon. If the pressure remains high and doesn't decay as expected, this can indicate a failure in the system (e.g., the balloon container did not dissolve, the balloon is expanding in the esophagus because there is, e.g., a kink in the tube or other failure in the catheter system). For example, for a successful decay using nitrogen only as the inflation fluid, the starting pressure is 22 PSI to inflate a balloon to 250 cc and 1.7 psi (0.120 kg/cm$^2$) for a nylon-based material. To indicate successful balloon inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Another method for detection of any degree of constraint that the balloon may be experiencing (e.g., capsule dissolved but balloon is in the esophagus or duodenum, or balloon is in the stomach and the capsule has not dissolved by reading the gauge output is to employ an inflation canister that has at least two reservoirs (one large and one small) and at least two gauges, with one or more valves that allow for selection of gas release into the second reservoir or into the balloon itself. With two reservoirs, the larger reservoir can contain the total amount of fluid required to fill the balloon. A small amount of fluid can be released from the larger reservoir into the smaller reservoir first to determine the location of the balloon and its readiness for full inflation. If the small amount of fluid in the smaller reservoir is released into the balloon catheter and the feedback on the gauge of the smaller reservoir indicates that the pressure is high, this indicates that the balloon is still contained in the capsule and it is not ready to be inflated. When the gauge reads back a medium pressure level (e.g., 1-4 psi), this indicates that the balloon is in a constrained space, such as the esophagus or duodenum, and should not be inflated. When the balloon catheter's feedback as read on the gauge is approximately 1 psi, this indicates that the balloon is in the stomach and ready to be inflated. If the feedback is at 0 psi, this indicates is a leak in the balloon valve catheter system and that the device should be retrieved. Once the balloon is detected in the stomach space, then the larger reservoir is opened and the balloon is inflated to its desired pressure.

Alternatively, the balloon can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user.

Composite Wall

The materials selected for the composite wall of the balloon may be optimized to maintain the original inflation gas without significant diffusion, or may also allow for diffusion of the gases located in the gastric environment, e.g., $CO_2$, $O_2$, argon, or $N_2$ to diffuse through the wall of the balloon to inflate, partially or wholly, once the balloon is placed in the stomach. A fluid (a liquid or gas) can also be added inside of the balloon using the inflation catheter(s) described herein to change diffusion direction of the balloon composite wall and when it reaches stasis based on the internal and external environment.

A gastric balloon inflated by nitrogen, $CO_2$ gas, a single fluid (gas) or a mixture of gasses employs a composite wall that provides barrier properties (fluid retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon. The inside of the balloon lumen may contain moisture from a solution injected in the balloon for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without significant damage or lodging. The outer container is small enough to transcend the esophagus (which has a diameter of approximately 2.5 cm). The wall or barrier material is also heat formable and sealable for balloon construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon (e.g., $CO_2$ retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or other structural layer.

TABLE 1a

Film Resins

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM RESINS | | | |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM COATINGS | | | |
| Silicon Dioxide ($SiO_2$) | | X | |
| Aluminum Oxide ($Al_2O_3$) | | X | |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metalized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon. Other layers may in addition or alternatively be included, including but not limited to those described in the following "Layer Chemistry" subsections.

Layer Chemistry

Polyethylene Terephthalate (PET)

Polyethylene terephthalate is a thermoplastic polymer resin of the polyester family. Polyethylene terephthalate may exist as an amorphous (transparent) or as a semi-crystalline material. The semi-crystalline material can appear transparent (spherulites <500 nm) or opaque and white (spherulites up to a size of some μm) depending on its crystal structure and spherulite size. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with ethylene glycol as the byproduct (the ethylene glycol is directly recycled in production). Some of the trade names of PET products are Dacron, Diolen, Tergal, Terylene, and Trevira fibers, Cleartuf, Eastman PET and Polyclear bottle resins, Hostaphan, Melinex, and Mylar films, and Arnite, Ertalyte, Impet, Rynite and Valox injection molding resins.

PET consists of polymerized units of the monomer ethylene terephthalate, with repeating C10H8O4 units. PET can be semi-rigid to rigid, depending on its thickness, and is very lightweight. It makes a good gas and fair moisture barrier, as well as a good barrier to alcohol and solvents. It is strong and impact-resistant. It is naturally colorless with high transparency.

When produced as a thin film (biaxially oriented PET film, often known by one of its trade names, "Mylar"), PET can be aluminized by evaporating a thin film of metal onto it to reduce its permeability, and to make it reflective and opaque (MPET). These properties are useful in many applications, including flexible food packaging. When filled with glass particles or fibers, it becomes significantly stiffer and more durable. This glass-filled plastic, in a semi-crystalline formulation, is sold under the trade names Rynite, Arnite, Hostadur, and Crastin.

One of the most important characteristics of PET is intrinsic viscosity. The intrinsic viscosity of the material, measured in deciliters per gram (dl/g) is dependent upon the length of its polymer chains. The longer the chains, the stiffer the material, and therefore the higher the intrinsic viscosity. The average chain length of a particular batch of resin can be controlled during polymerization. An intrinsic viscosity of about: 0.65 dl/g-0.84 dl/g is preferred for use in a composite wall.

In addition to pure (homopolymer) PET, PET modified by copolymerization is also available. In some cases, the modified properties of copolymer are more desirable for a particular application. For example, cyclohexane dimethanol (CHDM) can be added to the polymer backbone in place of ethylene glycol. Since this building block is much larger (6 additional carbon atoms) than the ethylene glycol unit it replaces, it does not fit in with the neighboring chains the way an ethylene glycol unit can. This interferes with crystallization and lowers the polymer's melting temperature. Such PET is generally known as PETG (Eastman Chemical and SK Chemicals are the only two manufacturers). PETG is a clear amorphous thermoplastic that can be injection molded or sheet extruded. It can be colored during processing. Another common modifier is isophthalic acid, replacing some of the 1,4-(para-) linked terephthalate units. The 1,2-(ortho-) or 1,3-(meta-) linkage produces an angle in the chain, which also disturbs crystallinity. Such copolymers are advantageous for certain molding applications, such as thermoforming. On the other hand, crystallization is important in other applications where mechanical and dimensional stability are important. For PET bottles, the use of small amounts of CHDM or other comonomers can be useful: if only small amounts of comonomers are used, crystallization is slowed but not prevented entirely. As a result, bottles are obtainable via stretch blow molding ("SBM"), which are both clear and crystalline enough to be an adequate barrier to aromas and gases such as carbon dioxide in carbonated beverages.

Crystallization occurs when polymer chains fold up on themselves in a repeating, symmetrical pattern. Long polymer chains tend to become entangled on themselves, which prevents full crystallization in all but the most carefully controlled circumstances. 60% crystallization is the upper limit for commercial products, with the exception of polyester fibers.

PET in its natural state is a crystalline resin. Clear products can be produced by rapidly cooling molten polymer to form an amorphous solid. Like glass, amorphous PET forms when its molecules are not given enough time to arrange themselves in an orderly fashion as the melt is cooled. At room temperature the molecules are frozen in place, but if enough heat energy is put back into them, they begin to move again, allowing crystals to nucleate and grow. This procedure is known as solid-state crystallization.

Like most materials, PET tends to produce many small crystallites when crystallized from an amorphous solid, rather than forming one large single crystal. Light tends to scatter as it crosses the boundaries between crystallites and the amorphous regions between them. This scattering means that crystalline PET is opaque and white in most cases. Fiber drawing is among the few industrial processes that produces a nearly single-crystal product.

Comonomers such as CHDM or isophthalic acid lower the melting temperature and reduces the degree of crystallinity of PET (especially important when the material is used for bottle manufacturing). Thus the resin can be plastically formed at lower temperatures and/or with lower force. This helps to prevent degradation, reducing the acetaldehyde content of the finished product to an acceptable (that is, unnoticeable) level. Other ways to improve the stability of the polymer is by using stabilizers, mainly antioxidants such as phosphites. Recently, molecular level stabilization of the material using nanostructured chemicals has also been considered.

Unreinforced PET has the following properties: Bulk Density 0.800-0.931 g/cc; Density 1.10-1.20 g/cc @Temperature 285-285° C.; 1.25-1.91 g/cc; Apparent Bulk Density 0.000850 g/cc; Water Absorption 0.0500-0.800%; Moisture Absorption at Equilibrium 0.200-0.300%; Water Absorption at Saturation 0.400-0.500%; Particle Size 2500 μm; Water Vapor Transmission 0.490-6.00 g/m$^2$/day; Oxygen Transmission 5.10-23.0 cc-mm/m$^2$-24 hr-atm; Viscosity Measurement 0.550-0.980; Viscosity Test 74.0-86.0 cm$^3$/g; Thickness 250-254 microns; Linear Mold Shrinkage 0.00100-0.0200 cm/cm; Linear Mold Shrinkage, Transverse 0.00200-0.0110 cm/cm; Hardness, Rockwell M 80.0-95.0; Hardness, Rockwell R 105-120 105-120; Ball Indentation Hardness 160-170 MPa; Tensile Strength, Ultimate 22.0-207 MPa; Film Tensile Strength at Yield, MD 55.0-59.0 MPa; Film Tensile Strength at Yield, TD 53.0-57.0 MPa; Film Elongation at Break, MD 40.0-600%; Film Elongation at Break, TD 200-600%; Film Elongation at Yield, MD 4.00-6.00%; Film Elongation at Yield, TD 4.00-6.00%; Tensile Strength, Yield 47.0-90.0 MPa; Elongation at Break 1.50-600%; Elongation at Yield 3.50-30.0%; Modulus of Elasticity 1.83-14.0 GPa; Flexural Modulus 1.90-15.2 GPa; Flexural Yield Strength 55.0-240 MPa; Compressive Yield Strength 20.0-123 MPa; Izod Impact, Unnotched 2.67 J/cm-NB; Izod Impact, Unnotched Low Temp (ISO) 160-181 kJ/m$^2$; Izod Impact, Notched, Low Temp (ISO) 3.10-4.20 kJ/m$^2$; Charpy Impact Unnotched 3.00 J/cm$^2$-NB; Charpy Impact, Notched, Low Temp 0.270-0.500 J/cm$^2$; Charpy Impact, Notched 0.200-1.40 J/cm$^2$; Impact Test 0.800-8.20 J @Temperature −40.0° C.; Coefficient of Friction 0.190-0.250; Tear Strength, Total 15.0-120 N; Elmendorf Tear Strength, MD 3.14-4.00 g/micron; Elmendorf Tear Strength, TD 3.24-5.20 g/micron; Dart Drop 1.08-2.00 g/micron; Taber Abrasion, mg/1000 Cycles; Film Tensile Strength at Break, MD 13.8-60.0 MPa; Film Tensile Strength at Break, TD 39.0-48.0 MPa; Izod Impact, Notched @-40° C. 0.270-0.630 J/cm; Izod Impact, Notched 0.139-100 J/cm; Izod Impact, Notched (ISO) 2.00-10.0 kJ/m$^2$; Electrical Resistivity 5.00e+6-1.00e+16 ohm-cm; Surface Resistance 1.00e+14-1.00e+16 ohm; Dielectric Constant 2.40-3.90; Dielectric Strength 15.7-60.0 kV/mm; Dissipation Factor 0.00100-0.0250; Arc Resistance 80.0-181 sec; Comparative Tracking Index 175-600 V; Heat of Fusion 56.0-65.0 J/g; CTE, linear 25.0-92.0 μm/m-° C.; CTE, linear, Transverse to Flow 48.0-80.0 μm/m-° C.; Specific Heat Capacity 1.10-1.20 J/g-° C.; 1.30-2.30 J/g-° C. @Temperature 60.0-280° C.; Thermal Conductivity 0.190-0.290 W/m-K; Melting Point 200-255° C.; Maximum Service Temperature, Air 100-225° C.; Deflection Temperature at 0.46 MPa (66 psi) 66.0-245° C.; Deflection Temperature at 1.8 MPa (264 psi) 60.0-240° C.; Vicat Softening Point 74.0-85.0° C.; Minimum Service Temperature, Air −20.0° C.; Glass Temperature 70.0-78.0° C.; UL RTI, Electrical 75.0-175° C.; Haze 0.300-10.0%; Gloss 108-166%; Transmission, Visible 67.0-99.0%; Gardner Color Number-3.00-85.0; Processing Temperature 120-295° C.; Mold Temperature 10.0-163° C.; Drying Temperature 70.0-160° C.; Dry Time 3.00-8.00 hour; Moisture Content 0.0100-0.400%; Injection Pressure 68.9-120 MPa; Back Pressure 8.00-18.0 MPa.

Polyethylene terephthalate films are available from Mitsubishi Polyester Film of Wiesbaden, Germany under the trade name Hostaphan®. Hostaphan® GN is a glass clear biaxially oriented film, made of polyethylene terephthalate (PET) and is characterized by its high transparency and surface gloss and its low haze accompanied by its excellent mechanical strength and dimensional stability. Hostaphan® GN is one or two side chemically treated for improved slip and processability as well as for improvement of the adhesion of coatings, printing inks or metallic layers. Hostaphan® RHBY is a biaxially oriented film made of polyethylene terephthalate (PET) with a structure optimized to offer previously unattainable barrier properties against oxygen, water vapor and other gases as well as aroma substances after vacuum coating with aluminum, Al2O3 or SiOx.

Linear Low-Density Polyethylene (LLDPE)

Linear low-density polyethylene (LLDPE) is a substantially linear polymer (polyethylene), with significant numbers of short branches, commonly made by copolymerization of ethylene with longer-chain olefins. Linear low-density polyethylene differs structurally from conventional low-density polyethylene because of the absence of long chain branching. The linearity of LLDPE results from the different manufacturing processes of LLDPE and LDPE. In general, LLDPE is produced at lower temperatures and pressures by copolymerization of ethylene and such higher alpha olefins as butene, hexene, or octene. The copolymerization process produces an LLDPE polymer that has a narrower molecular weight distribution than conventional LDPE and in combination with the linear structure, significantly different rheological properties.

The production of LLDPE is initiated by transition metal catalysts, particularly Ziegler or Philips type of catalyst. The actual polymerization process can be done in either solution phase or gas phase reactors. Usually, octene is the copolymer in solution phase while butene and hexene are copolymerized with ethylene in a gas phase reactor. The LLDPE resin produced in a gas phase reactor is in granular form and may be sold as granules or processed into pellets. LLDPE has higher tensile strength and higher impact and puncture resistance than LDPE. It is very flexible and elongates under stress. It can be used to make thinner films, with better environmental stress cracking resistance. It has good resistance to chemicals and to ultraviolet radiation. It has good electrical properties. However it is not as easy to process as LDPE, has lower gloss, and narrower range for heat sealing.

LDPE and LLDPE have unique theoretical or melt flow properties. LLDPE is less shear sensitive because of its narrower molecular weight distribution and shorter chain branching. During a shear process, such as extrusion, LLDPE remains more viscous, therefore harder to process than an LDPE of equivalent melt index. The lower shear sensitivity of LLDPE allows for a faster stress relaxation of the polymer chains during extrusion and therefore the physical properties are susceptible to changes in blow-up ratios. In melt extension, LLDPE has lower viscosity at all strain rates. This means it will not strain harden the way LDPE does when elongated. As the deformation rate of the polyethylene increases, LDPE demonstrates a dramatic rise in viscosity because of chain entanglement. This phenomena is not observed with LLDPE because of the lack of long-chain branching in LLDPE allows the chains to "slide by" one another upon elongation without becoming entangled. This characteristic is important for film applications because LLDPE films can be downgauged easily while maintaining high strength and toughness.

Properties of film grade LLDPE include: Density 0.902-0.960 g/cc; Moisture Vapor Transmission 0.240-0.470 cc-mm/$m^2$–24 hr-atm; Water Vapor Transmission 6.00-8.00 g/$m^2$/day; Oxygen Transmission 0.720-236 cc-mm/$m^2$–24 hr-atm; Oxygen Transmission Rate 3500-5000 cc/$m^2$/day; Viscosity 37000-79000 cP @Temperature 190-190° C.; 37000-79000 cP @Shear Rate 300-5000 l/s; 37000-79000 cP @Shear Rate 300-5000 l/s; Thickness 12.7-76.2 microns; Melt Flow 0.200-40.0 g/10 min; Base Resin Melt Index 0.700-3.50 g/10 min; Antiblock Level 3500-9000 ppm; Slip Level 0.000-1700 ppm; Tensile Strength, Ultimate 9.80-26.2 MPa; Film Tensile Strength at Yield, MD 7.38-74.0 MPa; Film Tensile Strength at Yield, TD 6.90-77.0 MPa; Film Elongation at Break, MD 80.0-1460%; Film Elongation at Break, TD 460-1710%; Film Elongation at Yield, MD 435-640%; Film Elongation at Yield, TD 670-890%; Tensile Strength, Yield 9.70-22.1 MPa; Elongation at Break 8.00-1000%; Modulus of Elasticity 0.0110-0.413 GPa; Secant Modulus, MD 0.0103-0.717 GPa; Secant Modulus, TD 0.0106-0.869 GPa; Impact 48.0-65.0; Impact Test 0.452-5.00 J; Coefficient of Friction 0.100-2.00; Coefficient of Friction, Static 0.170-1.00; Elmendorf Tear Strength MD 25.0-1080 g 2; Elmendorf Tear Strength TD 180-1470 g; Elmendorf Tear Strength, MD 0.0750-20.9 g/micron; Elmendorf Tear Strength, TD 0.275-37.8 g/micron; Dart Drop 1.57-42.5 g/micron; Dart Drop Test 30.0-1350 g; Seal Strength 1800-2400 g/25 mm; Film Tensile Strength at Break, MD 9.65-82.7 MPa; Film Tensile Strength at Break, TD 7.24-55.1 MPa; Heat Seal Strength Initiation Temperature 72.0-100° C.; Melting Point 120-128° C.; Crystallization Temperature 104-115° C.; Vicat Softening Point 93.0-123° C.; Haze 0.700-80.0%; Gloss 3.00-140%; Processing Temperature 90.0-310° C.; Die Opening 0.0810-0.254 cm; Blow-up Ratio (BUR) 1.50-4.00.

Ethylene Vinyl Alcohol (EVOH)

Ethylene Vinyl Alcohol is a formal copolymer of ethylene and vinyl alcohol. Because the latter monomer mainly exists as its tautomer acetaldehyde, the copolymer is prepared by polymerization of ethylene and vinyl acetate followed by hydrolysis. The plastic resin is commonly used in food applications, and in plastic gasoline tanks for automobiles. Its primary purpose is to provide barrier properties, primarily as an oxygen barrier for improved food packaging shelf life and as a hydrocarbon barrier for fuel tanks. EVOH is typically coextruded or laminated as a thin layer between cardboard, foil, or other plastics. EVOH copolymer is defined by the mole % ethylene content: lower ethylene content grades have higher barrier properties; higher ethylene content grades have lower temperatures for extrusion.

Ethylene Vinyl Alcohol (EVOH) is one of the most common clear high barrier films used today. It is applied as a discrete layer in a coextrusion. EVOH provides excellent oxygen barrier properties (0.006-0.12 cc-mil/100 in2-day). The barrier that a particular EVOH film provides is dependent upon a number of factors: mole percent—as the ethylene mole percent increases, the barrier decreases; degree of crystallinity—as the degree of crystallinity increases, the barrier properties improve; thickness—as with all films, as the thickness increases, the barrier increases; temperature—as the temperature increases, the barrier decreases; humidity—at high humidity levels, the barrier provided by EVOH drops rapidly (it is the humidity level at the EVOH interface rather than ambient humidity that is critical). In addition to providing an excellent oxygen barrier, EVOH is also an excellent odor and aroma barrier. It has the added advantage of being thermoformable making it popular for 3D applications.

EVALCA EVAL® EF-XL Ethylene Vinyl Alcohol Copolymer Film has the following properties: Moisture Vapor Transmission 0.600 cc-mm/$m^2$–24 hr-atm 40° C., 90% RH; Oxygen Transmission 0.00400 cc-mm/$m^2$–24 hr-atm 20° C.; 65% RH (permeability increases significantly at higher moisture content); thickness 15.2 microns; Film Elongation at Break, MD 100% 10%/min.; ASTM D638 Film Elongation at Break, TD 100% 10%/min.; ASTM D638 Secant Modulus, MD 3.50 GPa; Youngs Modulus, ASTM D638, 10%/min.; Secant Modulus, TD 3.50 GPa; Youngs Modulus, ASTM D638, 10%/min.; Elmendorf Tear Strength MD 260 g; ASTM D638 Elmendorf Tear Strength TD 330 g; ASTM D638 Elmendorf Tear Strength, MD 17.0 g/micron; ASTM D638 Elmendorf Tear Strength, TD 21.7 g/micron; ASTM D638 Film Tensile Strength at Break, MD 205 MPa 10%/min.; ASTM D638 Film Tensile Strength at Break, TD 195 MPa 10%/min.; Surface Resistance 2.70e+15 ohm; Dielectric Constant 5.00; Dissipation Factor 0.220; Specific Heat Capacity 2.40 J/g-° C.; Thermal Conductivity 0.340 W/m-K; Melting Point 181° C. DSC; Haze 0.500% 65% RH; Gloss 95.0% 65% RH. EVAL® ethylene vinyl alcohol films are available from Kuraray America, Inc. of Houston, Tex.

Nylon

Nylon is a generic designation for a family of synthetic polymers known generically as polyamides. Nylon is a thermoplastic silky material. There are two common methods of making nylon for fiber applications. In one approach, molecules with an acid (COOH) group on each end are reacted with molecules containing amine ($NH_2$) groups on each end. The resulting nylon is named on the basis of the number of carbon atoms separating the two acid groups and the two amines. These are formed into monomers of intermediate molecular weight, which are then reacted to form long polymer chains.

Solid nylon is used for mechanical parts such as machine screws, gears and other low- to medium-stress components previously cast in metal. Engineering-grade nylon is processed by extrusion, casting, and injection molding. Solid nylon is used in hair combs. Type 6/6 Nylon 101 is the most common commercial grade of nylon, and Nylon 6 is the most common commercial grade of molded nylon. Nylon is available in glass-filled variants which increase structural and impact strength and rigidity, and molybdenum sulfide-filled variants which increase lubricity.

Aramids are another type of polyamide with quite different chain structures which include aromatic groups in the main chain. Such polymers make excellent ballistic fibers.

Nylons are condensation copolymers formed by reacting equal parts of a diamine and a dicarboxylic acid, so that peptide bonds form at both ends of each monomer in a process analogous to polypeptide biopolymers. The numerical suffix specifies the numbers of carbons donated by the monomers; the diamine first and the diced second. The most common variant is nylon 6-6 which refers to the fact that the diamine (hexamethylene diamine) and the diacid (adipic acid) each donate 6 carbons to the polymer chain. As with other regular copolymers like polyesters and polyurethanes, the "repeating unit" consists of one of each monomer, so that they alternate in the chain. Since each monomer in this copolymer has the same reactive group on both ends, the direction of the amide bond reverses between each monomer, unlike natural polyamide proteins which have overall directionality. In the laboratory, nylon 6-6 can also be made using adipoyl chloride instead of adipic. It is difficult to get the proportions exactly correct, and deviations can lead to chain termination at molecular weights less than a desirable 10,000 daltons. To overcome this problem, a crystalline, solid "nylon salt" can be formed at room temperature, using an exact 1:1 ratio of the acid and the base to neutralize each other. Heated to 285° C., the salt reacts to form nylon polymer. Above 20,000 daltons, it is impossible to spin the chains into yarn, so to combat this some acetic acid is added to react with a free amine end group during polymer elongation to limit the molecular weight. In practice, and especially for nylon 6,6, the monomers are often combined in a water solution. The water used to make the solution is evaporated under controlled conditions, and the increasing concentration of "salt" is polymerized to the final molecular weight.

Homopolymer nylon 6, or polycaprolactam, is not a condensation polymer, but formed by a ring-opening polymerization (alternatively made by polymerizing aminocaproic acid). The peptide bond within the caprolactam is broken with the exposed active groups on each side being incorporated into two new bonds as the monomer becomes part of the polymer backbone. In this case, all amide bonds lie in the same direction, but the properties of nylon 6 are sometimes indistinguishable from those of nylon 6,6-except for melt temperature (N6 is lower) and some fiber properties in products like carpets and textiles. There is also nylon 9.

Nylon 5,10, made from pentamethylene diamine and sebacic acid has superior properties, but is more expensive to make. In keeping with this naming convention, "nylon 6,12" (N-6,12) or "PA-6,12" is a copolymer of a 6C diamine and a 12C diacid. Similarly for N-5,10 N-6,11; N-10,12, etc. Other nylons include copolymerized dicarboxylic acid/diamine products that are not based upon the monomers listed above. For example, some aromatic nylons are polymerized with the addition of diacids like terephthalic acid (Kevlar) or isophthalic acid (Nomex), more commonly associated with polyesters. There are copolymers of N-6,6/N6; copolymers of N-6,6/N-6/N-12; and others. Because of the way polyamides are formed, nylon can seem to be limited to unbranched, straight chains. But "star" branched nylon can be produced by the condensation of dicarboxylic acids with polyamines having three or more amino groups.

Above their melting temperatures, Tm, thermoplastics like nylon are amorphous solids or viscous fluids in which the chains approximate random coils. Below Tm, amorphous regions alternate with regions which are lamellar crystals. The amorphous regions contribute elasticity and the crystalline regions contribute strength and rigidity. The planar amide (—CO—NH—) groups are very polar, so nylon forms multiple hydrogen bonds among adjacent strands. Because the nylon backbone is so regular and symmetrical, especially if all the amide bonds are in the trans configuration, nylons often have high crystallinity and make excellent fibers. The amount of crystallinity depends on the details of formation, as well as on the kind of nylon. Apparently it can never be quenched from a melt as a completely amorphous solid.

Nylon 6,6 can have multiple parallel strands aligned with their neighboring peptide bonds at coordinated separations of exactly 6 and 4 carbons for considerable lengths, so the carbonyl oxygens and amide hydrogens can line up to form interchain hydrogen bonds repeatedly, without interruption. Nylon 5,10 can have coordinated runs of 5 and 8 carbons. Thus parallel (but not antiparallel) strands can participate in extended, unbroken, multi-chain β-pleated sheets, a strong and tough supermolecular structure similar to that found in natural silk fibroin and the β-keratins in feathers (proteins have only an amino acid a-carbon separating sequential —CO—NH— groups). Nylon 6 will form uninterrupted H-bonded sheets with mixed directionalities, but the β-sheet wrinkling is somewhat different. The three-dimensional disposition of each alkane hydrocarbon chain depends on rotations about the 109.47° tetrahedral bonds of singly-bonded carbon atoms.

Block nylon tends to be less crystalline, except near the surfaces due to shearing stresses during formation. Nylon is clear and colorless, or milky, but is easily dyed. Multistranded nylon cord and rope is slippery and tends to unravel. The ends can be melted and fused with a heat source such as a flame or electrode to prevent this.

When dry, polyamide is a good electrical insulator. However, polyamide is hygroscopic. The absorption of water will change some of the material's properties such as its electrical resistance. Nylon is less absorbent than wool or cotton.

Nylon can be used as the matrix material in composite materials, with reinforcing fibers like glass or carbon fiber, and has a higher density than pure nylon. Such thermoplastic composites (25% glass fiber) are frequently used in car components next to the engine, such as intake manifolds, where the good heat resistance of such materials makes them feasible competitors to metals.

All nylons are susceptible to hydrolysis, especially by strong acids, a reaction essentially the reverse of the synthetic reaction shown above. The molecular weight of nylon products so attacked drops fast, and cracks form quickly at the affected zones. Lower members of the nylons (such as nylon 6) are affected more than higher members such as nylon 12. This means that nylon parts cannot be used in contact with sulfuric acid for example, such as the electrolyte used in lead-acid batteries. When being molded, nylon must be dried to prevent hydrolysis in the molding machine barrel since water at high temperatures can also degrade the polymer.

Polyimide (PI)

Polyimide is a polymer of imide monomers. Thermosetting polyimides are commercially available as uncured resins, stock shapes, thin sheets, laminates and machines parts. Thermoplastic polyimides are very often called pseudothermoplastic. There are two general types of polyimides. One type, so-called linear polyimides, is made by combining imides into long chains. Aromatic heterocyclic polyimides are the other usual kind. Examples of polyimide films include Apical, Kapton, UPILEX, VTEC PI, Norton TH and Kaptrex. Polyimide parts and shapes include VTEC PI, Meldin, Vespel and typical monomers include pyromellitic dianhydride and 4,4'-oxydianiline.

Thermosetting polyimides are known for thermal stability, good chemical resistance, excellent mechanical properties, and characteristic orange/yellow color. Polyimides compounded with graphite or glass fiber reinforcements have flexural strengths of up to 50,000 psi and flexural moduli of 3,000,000 psi. Thermoset polyimides exhibit very low creep and high tensile strength. These properties are maintained during continuous use to temperatures of 232° C. and for short excursions, as high as 482° C. Molded polyimide parts and laminates have very good heat resistance. Normal operating temperatures for such parts and laminates range from cryogenic to those exceeding 260° C. Polyimides are also inherently resistant to flame combustion and do not usually need to be mixed with flame retardants. Most carry a UL rating of VTM-0. Polyimide laminates have a flexural strength half-life at 249° C. of 400 hours.

Typical polyimide parts are not affected by commonly used solvents and oils including hydrocarbons, esters, ethers, alcohols and freons. They also resist weak acids but are not recommended for use in environments that contain alkalis or inorganic acids. Some polyimides, such as CP1 and CORIN XLS, are solvent-soluble and exhibit high optical clarity. The solubility properties lend them towards spray and low temperature cure applications.

The polyimide materials are lightweight, flexible, resistant to heat and chemicals. Therefore, they are used in the electronics industry for flexible cables, as an insulating film on magnet wire and for medical tubing. For example, in a laptop computer, the cable that connects the main logic board to the display (which must flex every time the laptop is opened or closed) is often a polyimide base with copper conductors. The semiconductor industry uses polyimide as a high-temperature adhesive; it is also used as a mechanical stress buffer. Some polyimide can be used like a photoresist; both "positive" and "negative" types of photoresist-like polyimide exist in the market.

Thermoset film polyimide has the following properties: Density 1.40-1.67 g/cc; Water Absorption 1.40-3.00%; Moisture Absorption at Equilibrium 0.400-1.80%; Water Absorption at Saturation 1.20-2.50%; Moisture Vapor Transmission 2.40-17.5 cc-mm/m$^2$–24 hr-atm; Oxygen Transmission 9.90 cc-mm/m$^2$–24 hr-atm; Thickness 22.0-187 microns; Film Tensile Strength at Yield, MD 49.0-255 MPa; Film Tensile Strength at Yield, TD 100-160 MPa; Film Elongation at Break, MD 10.0-85.0%; Film Elongation at Yield, MD 40.0-50.0%; Film Elongation at Yield, TD 45.0-55.0%; Tensile Strength, Yield 73.3-160 MPa; Elongation at Yield 10.0-45.0%; Poissons Ratio 0.340; Secant Modulus 2.28-5.20 GPa; Secant Modulus, MD 1.76-9.12 GPa; Impact Test 0.686-1.56 J; Coefficient of Friction 0.400-0.480; Coefficient of Friction, Static 0.630; Tear Strength Test 7.20-430; Peel Strength 0.240 kN/m; Elmendorf Tear Strength MD 8.20-270 g; Film Tensile Strength at Break, MD 98.1-736 MPa; Electrical Resistivity 1.00e+10-2.30e+17 ohm-cm; 1.00e+15-1.00e+16 ohm-cm @Temperature 200° C.; Surface Resistance 10000-1.00e+17 ohm; 1.00e+15-1.00e+15 ohm @Temperature 200° C.; Dielectric Constant 2.70-4.00; Dielectric Strength 48.0-272 kV/mm @Temperature 200° C.; Dissipation Factor 0.00130-0.0100; CTE, linear 12.0-20.0 µm/m-° C.; 32.0-40.0 µm/m-° C. @Temperature 100-300° C.; Specific Heat Capacity 1.09-1.13 J/g-° C.; Thermal Conductivity 0.120-0.289 W/m-K; Maximum Service Temperature, Air 180-400° C.; Minimum Service Temperature, Air −269° C.; Glass Temperature 360-500° C.; Oxygen Index 37.0-66.0%; Shrinkage 0.0100-0.200%; Refractive Index 1.70.

Liquid Crystal Polymer (LCP)

Liquid-crystal polymers (LCPs) are a class of aromatic polyester polymers. They are extremely unreactive and inert, and highly resistant to fire. Liquid crystallinity in polymers may occur either by dissolving a polymer in a solvent (lyotropic liquid-crystal polymers) or by heating a polymer above its glass or melting transition point (thermotropic liquid-crystal polymers). Liquid-crystal polymers are present in melted/liquid or solid form. In liquid form liquid-crystal polymers have primarily applications in liquid-crystal displays (LCDs). In solid form the main example of lyotropic LCPs is the commercial aramid known as Kevlar. The chemical structure of this aramid consists of linearly substituted aromatic rings linked by amide groups. In a similar way, several series of thermotropic LCPs have been commercially produced by several companies (e.g., Vectra). A high number of LCPs, produced in the 1980s, displayed order in the melt phase analogous to that exhibited by nonpolymeric liquid crystals. Processing of LCPs from liquid-crystal phases (or mesophases) gives rise to fibers and injected materials having high mechanical properties as a consequence of the self-reinforcing properties derived from the macromolecular orientation in the mesophase. Today, LCPs can be melt-processed on conventional equipment at high speeds with excellent replication of mold details.

A unique class of partially crystalline aromatic polyesters based on p-hydroxybenzoic acid and related monomers, liquid-crystal polymers is capable of forming regions of highly ordered structure while in the liquid phase. However, the degree of order is somewhat less than that of a regular solid crystal. Typically LCPs have a high mechanical strength at high temperatures, extreme chemical resistance, inherent flame retardancy, and good weatherability. Liquid-crystal polymers come in a variety of forms from sinterable high temperature to injection moldable compounds. LCP can be welded, though the lines created by welding are a weak point in the resulting product. LCP has a high Z-axis coefficient of thermal expansion.

LCPs are exceptionally inert. They resist stress cracking in the presence of most chemicals at elevated temperatures, including aromatic or halogenated hydrocarbons, strong acids, bases, ketones, and other aggressive industrial substances. Hydrolytic stability in boiling water is excellent. Environments that deteriorate the polymers are high-temperature steam, concentrated sulfuric acid, and boiling caustic materials. Because of their various properties, LCPs are useful for electrical and mechanical parts, food containers, and any other applications requiring chemical inertness and high strength.

High-Density Polyethylene (HDPE)

High-density polyethylene (HDPE) or polyethylene high-density (PEHD) is a polyethylene thermoplastic made from petroleum. HDPE has little branching, giving it stronger intermolecular forces and tensile strength than lower-density polyethylene. It is also harder and more opaque and can withstand somewhat higher temperatures (120° C. for short periods, 110° C. continuously). High-density polyethylene, unlike polypropylene, cannot withstand normally-required autoclaving conditions. The lack of branching is ensured by an appropriate choice of catalyst (e.g., Ziegler-Natta catalysts) and reaction conditions. HDPE contains the chemical elements carbon and hydrogen. Hollow goods manufactured through blow molding are the most common application area for HDPE.

Polypropylene (PP)

Polypropylene or polypropene (PP) is a thermoplastic polymer, made by the chemical industry and used in a wide variety of applications, including packaging, textiles (e.g. ropes, thermal underwear and carpets), stationery, plastic parts and reusable containers of various types, laboratory equipment, loudspeakers, automotive components, and polymer banknotes. An addition polymer made from the monomer propylene, it is rugged and unusually resistant to many chemical solvents, bases and acids.

Most commercial polypropylene is isotactic and has an intermediate level of crystallinity between that of low density polyethylene (LDPE) and high density polyethylene (HDPE); its Young's modulus is also intermediate. PP is normally tough and flexible, especially when copolymerized with ethylene. This allows polypropylene to be used as an engineering plastic, competing with materials such as ABS. Polypropylene is reasonably economical, and can be made translucent when uncolored but is not as readily made transparent as polystyrene, acrylic or certain other plastics. It is often opaque and/or colored using pigments. Polypropylene has good resistance to fatigue.

Polypropylene has a melting point of ~160° C. (320° F.), as determined by Differential scanning calorimetry (DSC). The MFR (Melt Flow Rate) or MFI (Melt Flow Index) is a measure of PP's molecular weight. This helps to determine how easily the molten raw material will flow during processing. Higher MFR PPs fill the plastic mold more easily during the injection or blow molding production process. As the melt flow increases, however, some physical properties, like impact strength, will decrease.

There are three general types of PP: homopolymer, random copolymer and block copolymer. The comonomer used is typically ethylene. Ethylene-propylene rubber or EPDM added to PP homopolymer increases its low temperature impact strength. Randomly polymerized ethylene monomer added to PP homopolymer decreases the polymer crystallinity and makes the polymer more transparent.

Polypropylene is liable to chain degradation from exposure to UV radiation such as that present in sunlight. For external applications, UV-absorbing additives must be used. Carbon black also provides some protection from UV attack. The polymer can also be oxidized at high temperatures, a common problem during molding operations. Anti-oxidants are normally added to prevent polymer degradation.

The relative orientation of each methyl group relative to the methyl groups on neighboring monomers has a strong effect on the finished polymer's ability to form crystals, because each methyl group takes up space and constrains backbone bending.

Like most other vinyl polymers, useful polypropylene cannot be made by radical polymerization due to the higher reactivity of the allylic hydrogen (leading to dimerization) during polymerization. Moreover, the material that can result from such a process can have methyl groups arranged randomly, so called atactic PP. The lack of long-range order prevents any crystallinity in such a material, giving an amorphous material with very little strength and only specialized qualities suitable for niche end uses.

A Ziegler-Natta catalyst is able to limit incoming monomers to a specific orientation, only adding them to the polymer chain if they face the right direction. Most commercially available polypropylene is made with such Ziegler-Natta catalysts, which produce mostly isotactic polypropylene. With the methyl group consistently on one side, such molecules tend to coil into a helical shape; these helices then line up next to one another to form the crystals that give commercial polypropylene many of its desirable properties.

More precisely engineered Kaminsky catalysts have been made, which offer a much greater level of control. Based on metallocene molecules, these catalysts use organic groups to control the monomers being added, so that a proper choice of catalyst can produce isotactic, syndiotactic, or atactic polypropylene, or even a combination of these. Aside from this qualitative control, they allow better quantitative control, with a much greater ratio of the desired tacticity than previous Ziegler-Natta techniques. They also produce narrower molecular weight distributions than traditional Ziegler-Natta catalysts, which can further improve properties.

To produce a rubbery polypropylene, a catalyst can be made which yields isotactic polypropylene, but with the organic groups that influence tacticity held in place by a relatively weak bond. After the catalyst has produced a short length of polymer which is capable of crystallization, light of the proper frequency is used to break this weak bond, and remove the selectivity of the catalyst so that the remaining length of the chain is atactic. The result is a mostly amorphous material with small crystals embedded in it. Since each chain has one end in a crystal but most of its length in the soft, amorphous bulk, the crystalline regions serve the same purpose as vulcanization.

Melt processing of polypropylene can be achieved via extrusion and molding. Common extrusion methods include production of melt blown and spun bond fibers to form long rolls for future conversion into a wide range of useful products such as face masks, filters, nappies and wipes. The most common shaping technique is injection molding, which is used for parts such as cups, cutlery, vials, caps, containers, housewares and automotive parts such as batteries. The related techniques of blow molding and injection-stretch blow molding are also used, which involve both extrusion and molding.

The large number of end use applications for PP is often possible because of the ability to tailor grades with specific molecular properties and additives during its manufacture. For example, antistatic additives can be added to help PP surfaces resist dust and dirt. Many physical finishing techniques can also be used on PP, such as machining. Surface treatments can be applied to PP parts in order to promote adhesion of printing ink and paints.

Since polypropylene is resistant to fatigue, most plastic living hinges, such as those on flip-top bottles, are made from this material. However, it is important to ensure that chain molecules are oriented across the hinge to maximize strength. Very thin sheets of polypropylene are used as a dielectric within certain high performance pulse and low loss RF capacitors.

High-purity piping systems are built using polypropylene. Stronger, more rigid piping systems, intended for use in potable plumbing, hydronic heating and cooling, and reclaimed water applications, are also manufactured using polypropylene. This material is often chosen for its resistance to corrosion and chemical leaching, its resilience against most forms of physical damage, including impact and freezing, and its ability to be joined by heat fusion rather than gluing.

Many plastic items for medical or laboratory use can be made from polypropylene because it can withstand the heat in an autoclave. Its heat resistance also enables it to be used as the manufacturing material of consumer-grade kettles. Food containers made from it will not melt in the dishwasher, and do not melt during industrial hot filling processes. For this reason, most plastic tubs for dairy products are polypropylene sealed with aluminum foil (both heat-resistant materials). After the product has cooled, the tubs are often given lids made of a less heat-resistant material, such as LDPE or polystyrene. Such containers provide a good hands-on example of the difference in modulus, since the rubbery (softer, more flexible) feeling of LDPE with respect to PP of the same thickness is readily apparent. Rugged, translucent, reusable plastic containers made in a wide variety of shapes and sizes for consumers from various companies such as Rubbermaid and Sterilite are commonly made of polypropylene, although the lids are often made of somewhat more flexible LDPE so they can snap on to the container to close it. Polypropylene can also be made into disposable bottles to contain liquid, powdered or similar consumer products, although HDPE and polyethylene terephthalate are commonly also used to make bottles. Plastic pails, car batteries, wastebaskets, cooler containers, dishes and pitchers are often made of polypropylene or HDPE, both of which commonly have rather similar appearance, feel, and properties at ambient temperature.

Polypropylene is a major polymer used in nonwovens, with over 50% used for diapers or sanitary products where it is treated to absorb water (hydrophilic) rather than naturally repelling water (hydrophobic). Other interesting non-woven uses include filters for air, gas and liquids where the fibers can be formed into sheets or webs that can be pleated to form cartridges or layers that filter in various efficiencies in the 0.5 to 30 micron range. Such applications can be seen in the house as water filters or air conditioning type filters. The high surface area and naturally hydrophobic polypropylene nonwovens are ideal absorbers of oil spills with the familiar floating barriers near oil spills on rivers.

A common application for polypropylene is as Biaxially Oriented polypropylene (BOPP). These BOPP sheets are used to make a wide variety of materials including clear bags. When polypropylene is biaxially oriented, it becomes crystal clear and serves as an excellent packaging material for artistic and retail products.

Polypropylene's most common medical use is in the synthetic, nonabsorbable suture Prolene, manufactured by Ethicon Inc.

Polypropylene is most commonly used for plastic moldings where it is injected into a mold while molten, forming complex shapes at relatively low cost and high volume, examples include bottle tops, bottles and fittings.

Recently it has been produced in sheet form and this has been widely used for the production of stationary folders, packaging and storage boxes. The wide color range, durability and resistance to dirt make it ideal as a protective cover for papers and other materials. It is used in Rubik's cube stickers because of these characteristics.

Expanded Polypropylene (EPP) is a foam form of polypropylene. EPP has very good impact characteristics due to its low stiffness; this allows EPP to resume its shape after impacts. EPP is extensively used in model aircraft and other radio controlled vehicles by hobbyists. This is mainly due to its ability to absorb impacts, making this an ideal material for RC aircraft for beginners and amateurs.

Silicon Dioxide ($SiO_2$)

The chemical compound silicon dioxide, also known as silica, is an oxide of silicon with a chemical formula of $SiO_2$. Oxides of silicon, commonly referred to as "SiOx," include silicon dioxide. Silica is most commonly found in nature as sand or quartz, as well as in the cell walls of diatoms. It is a principal component of most types of glass and substances such as concrete. Silica is the most abundant mineral in the Earth's crust.

$SiO_2$ has a number of distinct crystalline forms in addition to amorphous forms. With the exception of stishovite and fibrous silica, all of the crystalline forms involve tetrahedral $SiO_4$ units linked together by shared vertices in different arrangements. Silicon-oxygen bond lengths vary between the different crystal forms. In a-quartz the Si—O—Si angle is 144°. The only stable form under normal conditions is a-quartz and this is the form in which crystalline silicon dioxide is usually encountered.

Silicon dioxide is formed when silicon is exposed to oxygen (or air). A very thin layer (approximately 1 nm or 10 Å) of so-called 'native oxide' is formed on the surface when silicon is exposed to air under ambient conditions. Higher temperatures and alternative environments are used to grow well-controlled layers of silicon dioxide on silicon, for example at temperatures between 600 and 1200° C., using the so-called "dry" or "wet" oxidation with $O_2$ or $H_2O$, respectively. The thickness of the layer of silicon replaced by the dioxide is 44% of the thickness of the silicon dioxide layer produced. Alternative methods used to deposit a layer of $SiO_2$ include: Low temperature oxidation (400-450° C.) of silane; Decomposition of tetraethyl orthosilicate (TEOS) at 680-730° C.; Plasma enhanced chemical vapor deposition using TEOS at about 400° C.; Polymerization of tetraethyl orthosilicate (TEOS) at below 100° C. using amino acid as catalyst.

Pyrogenic silica (sometimes called fumed silica or silica fume), which is a very fine particulate form of silicon dioxide, is prepared by burning $SiCl_4$ in an oxygen rich hydrocarbon flame to produce a "smoke" of $SiO_2$. Amorphous silica, silica gel, is produced by the acidification of solutions of sodium silicate to produce a gelatinous precipitate that is then washed and then dehydrated to produce colorless microporous silica.

Aluminum Oxide ($Al_2O_3$)

Aluminum oxide is an amphoteric oxide of aluminum with the chemical formula $Al_2O_3$. It is also commonly referred to as alumina, corundum, sapphire, ruby or aloxite. Aluminum oxide is an electrical insulator but has a relatively high thermal conductivity (40 $Wm{-}1K{-}1$) for a ceramic material. In its most commonly occurring crystalline form, called corundum or a-aluminum oxide, its hardness makes it suitable for use as an abrasive and as a component in cutting tools. Aluminum oxide is responsible for resistance of metallic aluminum to weathering. Metallic aluminum is very reactive with atmospheric oxygen, and a thin passivation layer of alumina (4 nm thickness) forms in about 100 picoseconds on any exposed aluminum surface. This layer protects the metal from further oxidation. The thickness and properties of this oxide layer can be enhanced using a process called anodizing. A number of alloys, such as aluminum bronzes, exploit this property by including a proportion of aluminum in the alloy to enhance corrosion resistance. The alumina generated by anodizing is typically amorphous, but discharge assisted oxidation processes such as plasma electrolytic oxidation result in a significant proportion of crystalline alumina in the coating, enhancing its hardness. The most common form of crystalline alumina, a-aluminum oxide, is known as corundum. Alumina also exists in other phases. Each has a unique crystal structure and properties. Aluminum hydroxide minerals are the main component of bauxite, the principal ore of aluminum. Alumina tends to be multi-phase; e.g., constituting several of the alumina phases rather than solely corundum.

Polyvinyl Alcohol (PVOH, PVA, or PVAL)

Polyvinyl alcohol (PVOH, PVA, or PVAL) is a water-soluble synthetic polymer. Polyvinyl alcohol has excellent film forming, emulsifying, and adhesive properties. It is also resistant to oil, grease and solvent. It is odorless and non-toxic. It has high tensile strength and flexibility, as well as high oxygen and aroma barrier properties. However these properties are dependent on humidity, in other words, with higher humidity more water is absorbed. The water, which acts as a plasticizer, will then reduce its tensile strength, but increase its elongation and tear strength. PVA is fully degradable and is a quick dissolver. PVA has a melting point of 230° C. and 180-190° C. for the fully hydrolyzed and partially hydrolyzed grades, respectively. It decomposes rapidly above 200° C. as it can undergo pyrolysis at high temperatures.

PVA is an atactic material but exhibits crystallinity as the hydroxyl groups are small enough to fit into the lattice without disrupting it. Unlike most vinyl polymers, PVA is not prepared by polymerization of the corresponding monomer. The monomer, vinyl alcohol, almost exclusively exists as the tautomeric form, acetaldehyde. PVA instead is prepared by partial or complete hydrolysis of polyvinyl acetate to remove acetate groups.

Nanopolymers

Polymer nanocomposite (PNC) is a polymer or copolymer having dispersed in its nanoparticles. These may be of different shape (e.g., platelets, fibers, spheroids), but at least one dimension is in the range of 1 to 50 nm. The transition from micro- to nano-particles leads to changes in physical as well as chemical properties. Two of the major factors in this are the increase in the ratio of the surface area to volume, and the size of the particle. The increase in surface area-to-volume ratio, which increases as the particles get smaller, leads to an increasing dominance of the behavior of atoms on the surface area of particle over that of those interior of the particle. This affects the properties of the particles when they are reacting with other particles. Because of the higher surface area of the nano-particles the interaction with the other particles within the mixture is more and this increases the strength, heat resistance etc. and many factors do change for the mixture.

An example of a nanopolymer is silicon nanospheres which show quite different characteristics. The particle size is 40-100 nm and it is much harder than silicon (a hardness between that of sapphire and diamond). Many technical applications of biological objects like proteins, viruses or bacteria such as chromatography, optical information technology, sensors, catalysis and drug delivery require their immobilization. Carbon nanotubes, gold particles and synthetic polymers are used for this purpose. This immobilization has been achieved predominantly by adsorption or by chemical binding and to a lesser extent by incorporating these objects as guests in host matrices. In the guest host systems, an ideal method for the immobilization of biological objects and their integration into hierarchical architectures should be structured on a nanoscale to facilitate the interactions of biological nano-objects with their environment. Due to the large number of natural or synthetic polymers available and the advanced techniques developed to process such systems to nanofibers, rods, tubes etc. make polymers a good platform for the immobilization of biological objects.

Polymer fibers are, in general, produced on a technical scale by extrusion, e.g., a polymer melt or a polymer solution is pumped through cylindrical dies and spun/drawn by a take-up device. The resulting fibers have diameters typically on the 10-μm scale or above. To come down in diameter into the range of several hundreds of nanometers or even down to a few nanometers, electrospinning is today still the leading polymer processing technique available. A strong electric field of the order of 103 V/cm is applied to the polymer solution droplets emerging from a cylindrical die. The electric charges, which are accumulated on the surface of the droplet, cause droplet deformation along the field direction, even though the surface tension counteracts droplet evolution. In supercritical electric fields, the field strength overbears the surface tension and a fluid jet emanates from the droplet tip. The jet is accelerated towards the counter electrode. During this transport phase, the jet is subjected to strong electrically driven circular bending motions that cause a strong elongation and thinning of the jet, a solvent evaporation until, finally, the solid nanofiber is deposited on the counter electrode.

Electro spinning, co-electrospinning, and the template methods based on nanofibers yield nano-objects which are, in principle, infinitively long. For a broad range of applications including catalysis, tissue engineering, and surface modification of implants this infinite length is an advantage. But in some applications like inhalation therapy or systemic drug delivery, a well-defined length is required. The template method to be described in the following has the advantage such that it allows the preparation of nanotubes and nanorods with very high precision. The method is based on the use of well-defined porous templates, such as porous aluminum or silicon. The basic concept of this method is to exploit wetting processes. A polymer melt or solution is brought into contact with the pores located in materials characterized by high energy surfaces such as aluminum or silicon. Wetting sets in and covers the walls of the pores with a thin film with a thickness of the order of a few tens of nanometers. This process happens typically within a minute for temperatures about 50 K above the melting temperature or glass transition temperature, even for highly viscous polymers, such as, for instance, polytetrafluoroethylene, and this holds even for pores with an aspect ratio as large as 10,000. To obtain nanotubes, the polymer/template system is cooled down to room temperature or the solvent is evaporated, yielding pores covered with solid layers. The resulting tubes can be removed by mechanical forces for tubes up to 10 μm in length, e.g., by just drawing them out from the pores or by selectively dissolving the template. The diameter of the nanotubes, the distribution of the diameter, the homogeneity along the tubes, and the lengths can be controlled.

The size-dependent and pressure-dependent glass transition temperatures of free-standing films or supported films having weak interactions with substrates decreases with decreasing of pressure and size. However, the glass transition temperature of supported films having strong interaction with substrates increases of pressure and the decrease of size.

Nanocomposites are polymer structures that contain fillers, typically silicate nanoclays, with at least one dimension in the nanometer range. The fillers separate into tiny platelets that disperse into a matrix of layers. Because the matrix of layers creates a tortuous path for gasses trying to permeate through the film, the barrier properties of the modified polymer are improved. However, the challenge is to ensure that that the filler dispersion is consistent. In addition to better barrier properties, nanocomposites modified films also have improved dimensional stability and stiffness and, because crystallinity is increased, enhanced clarity. Nanocomposite masterbatches are commercially available for nylon and polyolefins. The oxygen barrier of nylon nanocomposite films can be as much as 50 percent higher than a nonmodified nylon. Polyethylene and polypropylene nanocomposite structures have shown improvement in gas barrier of 25 to 50 percent and in water vapor of 10 to 15 percent in laboratory settings. Achieving consistent barrier properties on a commercial scale remains challenging. Nanocomposite technology is very much an emerging science. It shows a great deal of promise and as more options become available for film applications it will have a significant impact on barrier material options.

Saran

Saran is the trade name for a number of polymers made from vinylidene chloride (especially polyvinylidene chloride or PVDC), along with other monomers. Saran film has a very low permeability to water vapor, flavor and aroma molecules, and oxygen compared to other plastics. The barrier to oxygen prevents food spoilage, and the barrier to flavor and aroma molecules helps food retain its flavor and aroma. Saran also possesses gas barrier properties.

Polytrimethylene Terephthalate (PTT)

Polytrimethylene Terephthalate (PTT) is a semi crystalline polymer that has many of the same advantages as PET. PTT exhibits good tensile strength, flexural strength, and stiffness. It has excellent flow and surface finish. PTT can have more uniform shrinkage and better dimensional stability in some applications than competing semicrystalline materials. PTT has excellent resistance to a broad range of chemicals at room temperature, including aliphatic hydrocarbons, gasoline, carbon tetrachloride, perchloroethylene, oils, fats, alcohols, glycols, esters, ethers and dilute acids and bases. Strong bases may attack PTT compounds. Impact modifiers and reinforcing fibers (long glass, short glass, or carbon) can be used to increase the impact properties, as well as the strength and stiffness of PTT.

Polytrimethylene Naphthalate (PTN)

Poly(trimethylene phthalates or naphthalate) and copolymers are aromatic polyesters made by polycondensation of 1,3-propanediol (PDO) and terephthalic acid (PTT), isophthalic acid (PTI) or naphthalic acid (PTN) and/or with comonomers (isophthalic acid, 1,4-butanediol, etc.). Films of PTN possess good barrier properties.

Polyethylene Naphthalate (PEN)

Polyethylene naphthalate (PEN) is a polyester with good barrier properties (even better than polyethylene terephthalate). Because it provides a very good oxygen barrier, it is particularly well-suited for bottling beverages that are susceptible to oxidation, such as beer. It is prepared from ethylene glycol and one or more naphthalene dicarboxylic acids by condensation polymerization.

Polyurethane

A polyurethane is any polymer consisting of a chain of organic units joined by urethane (carbamate) links. Polyurethane polymers are formed through step-growth polymerization by reacting a monomer containing at least two isocyanate functional groups with another monomer containing at least two hydroxyl (alcohol) groups in the presence of a catalyst. Polyurethane formulations cover an extremely wide range of stiffness, hardness, and densities. Though the properties of the polyurethane are determined mainly by the choice of polyol, the diisocyanate exerts some influence, and must be suited to the application. The cure rate is influenced by the functional group reactivity and the number of functional isocyanate groups. The mechanical properties are influenced by the functionality and the molecular shape. The choice of diisocyanate also affects the stability of the polyurethane upon exposure to light. Polyurethanes made with aromatic diisocyanates yellow with exposure to light, whereas those made with aliphatic diisocyanates are stable. Softer, elastic, and more flexible polyurethanes result when linear difunctional polyethylene glycol segments, commonly called polyether polyols, are used to create the urethane links. This strategy is used to make spandex elastomeric fibers and soft rubber parts, as well as foam rubber. More rigid products result if polyfunctional polyols are used, as these create a three-dimensional crosslinked structure which, again, can be in the form of a low-density foam.

Polyether Block Amide (PEBAX®)

Polyether block amide is a thermoplastic elastomer or a flexible polyamide without plasticizer consisting of a regular linear chain of rigid polyamide segments and flexible polyether segments.

Parylene C

Parylene is the trade name for a variety of chemical vapor deposited poly(p-xylylene) polymers used as moisture barriers and electrical insulators. Among them, Parylene C is the most popular due to its combination of barrier properties, cost, and other manufacturing advantages.

Silicone

Silicones, also referred to as polymerized siloxanes or polysiloxanes, are mixed inorganic-organic polymers with the chemical formula $[R_2SiO]_n$, where R is an organic group such as methyl, ethyl, or phenyl. These materials consist of an inorganic silicon-oxygen backbone ( . . . —Si—O—Si—O—Si—O— . . . ) with organic side groups attached to the silicon atoms, which are four-coordinate. In some cases organic side groups can be used to link two or more of these —Si—O— backbones together. By varying the —Si—O— chain lengths, side groups, and crosslinking, silicones can be synthesized with a wide variety of properties and compositions. They can vary in consistency from liquid to gel to rubber to hard plastic. The most common siloxane is linear polydimethylsiloxane (PDMS), a silicone oil. The second largest group of silicone materials is based on silicone resins, which are formed by branched and cage-like oligosiloxanes.

Fabrication of the Composite Wall

The various layers of the composite wall, including the gas barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.0254 cm) to 0.004 inches (0.010 cm) thick is desirable such that the resulting balloon compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon containing nitrogen, oxygen, $CO_2$ or a mixture thereof as the inflation gas or where the external environment the product is to be placed in, contains a mixture of gases including $CO_2$, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon wall as a monolayer film; however they can also be used in conjunction with other film resins to meet the desired gas retention and mechanical specifications for the useful life of the balloon based on the inflation gas and external environment the balloon is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified gas retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET, or a uniform polymeric blend), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si—Ox is provided on a supporting PET layer. In the following table, as well as other tables referring to composite walls, a forward slash ("/") is used to indicate a boundary between layers of the specified chemistries. The boundary can be a discontinuity, or can be a tie layer, adhesive layer, or other layer separating the layers of recited chemistry.

TABLE 2

| Example Film Composite Walls* | Abbreviation | Trade name |
|---|---|---|
| polyethylene terephthalate | PET | Mylar |
| metalized oriented polyethylene terephthalate | metalized OPET | Custom |
| polyvinyl alcohol coated oriented polypropylene | PVOH coated OPP | Bicor |
| metalized biaxially oriented nylon 6 | metalized OPA6 | Custom |
| Biaxally oriented Nylon/ethylene vinyl alcohol/biaxially oriented Nylon | OPA/EVOH/OPA | Honeywell Oxyshield Plus |
| Nylon/ethylene vinyl alcohol/Low Density Polyethylene | Nylon/EVOH/LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated | PVCD/OPA6 | Honeywell |

TABLE 2-continued

| Example Film Composite Walls* | Abbreviation | Trade name |
|---|---|---|
| biaxially oriented Nylon 6 | | Oxyshield |
| high density polyethylene/ethylene vinyl alcohol | HDPE/EVOH | Custom |
| polypropylene/ethylene vinyl alcohol laminate | PP/EVOH | Custom |
| polyethylene terephthalate/ethylene vinyl alcohol | PET/EVOH | Custom |
| metalized oriented polypropylene | metalized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |
| Nylon-High Density Polyethylene | Nylon-HDPE laminate | Custom |
| Nylon 12/Ethyl Methyl Acrylate/Polyvinylidene Chloride/ Ethyl Methyl Acrylate/Nylon 12/Linear Low Density Polyethylene + Low Density Polyethylene | Co-extruded Nylon 12-encapsulated PVDC-Nylon 12-LLDPE + LDPE | Custom Co-extruded blend |
| Multi-layer Nylon 12/Linear Low Density Polyethylene + Low Density Polyethylene | Co-extruded multi-layer Nylon 12-LLDPE + LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |
| acetylene plasma coating on polypropylene | PP/A | Custom |
| acetylene plasma coating on low density polyethylene | LDPE/A | Custom |
| polybutylene terephthalate polyether glycol copolymer | TPC-ET | Hytrel |
| polyether block amide TPE | PEBA | Pebax |
| oxide coated biaxially oriented Nylon | oxide coated PA | Honeywell Oxyshield Ultra |
| Nanoclay/nylon | MXD6/Nanoclay | Imperm/Aegis OXCE |
| Polyethylene Terephthalate/Silicone Dioxide | PET/SiOx | BestPET/ TechBarrier |
| Polyethylene Terephthalate/Oxygen scavengers | PET + 02 Scavengers | MonoxBar |
| Modified Polyethylene Terephthalate | Modified PET | DiamondClear |
| Polyethylene Terephthalate/Nylon 6 | PET/MXD6 | HP867 |
| Amorphous polyvinyl alcohol | Amorphous PVOH | Nichigo G-Polymer |
| Nylon 6/Ethyl vinyl alcohol/Linear Low Density Polyethylene | Nylon 6/EVOH/LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/ Polyethylene Terephthalate | PE/EVOH/PET | Custom |
| Silicon dioxide-coated Polyethylene Terephthalate/Linear | PET-SiOx/LLDPE/EVOH/LLDPE | Custom |

TABLE 2-continued

| Example Film Composite Walls* | Abbreviation | Trade name |
|---|---|---|
| Low Density Polyethylene/Ethyl vinyl alcohol/Linear Low Density Polyethylene | | |
| Aluminum Oxide-coated Polyethylene Terephthalate/Polyethylene | PET-Al$_2$O$_3$/LLDPE | Custom |
| Polyethylene/Ethyl vinyl alcohol/Linear Low Density Polyethylene | PE/EVOH/LLDPE | Custom |
| Polyethylene Terephthalate/Polyethylene/Polyethylene/Bi-axially oriented Ethyl vinyl alcohol | PET/PE/OEVOH/PE | Custom |
| Polyethylene Terephthalate/Polyethylene/Ethyl vinyl alcohol/Ethyl vinyl alcohol/Ethyl vinyl alcohol/Polyethylene | PET/PE/EVOH/EVOH/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Silicon dioxide-coated Polyethylene Terephthalate/Polyethylene/Ethyl vinyl alcohol/Polyethylene | PET-SiOx/PE/EVOH/PE | Custom |
| Polyethylene/Ethyl vinyl alcohol/polyvinylchloride | PE/EVOH/PVDC | Custom |
| Polyethylene Terephthalate/Linear Low Density Polyethylene/Ethyl vinyl alcohol/Linear Low Density Polyethylene | PET/LLDPE/EVOH/LLDPE | Custom |
| Kurrarister C-coated Polyethylene Terephthalate/Polyethylene/Ethyl vinyl alcohol/Polyethylene | PET-Kurrarister-C/PE/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Nylon 6/Ethyl vinyl alcohol/Polyvinylchloride/Low Density Polyethylene | Nylon 6/EVOH/PVDC/Nylon 6/LDPE | Custom |
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/Linear Low Density Polyethylene | PI/PVdC/LLDPE | Custom |

In particularly preferred embodiments, the composite wall has a thickness of 0.005 inches or less (5.0 mil or less); however, in certain embodiments a thicker composite wall may be acceptable. Generally it is preferred that the composite wall have a thickness of no more than 0.004 inches (4.0 mil).

Fabrication of the Balloon

To ensure good mechanical strength of the balloon, the balloon is preferably thermoformed and sealed such that the edges of the pieces used to form the balloon are overlapping. This can be accomplished by any suitable method. For example, two flat sheets of material can be placed in a frame with magnetized edges to hold the two sheets in place. Slack can be added to the piece of film to orient the material such that it maintains its properties after the thermoforming process. The frame can be placed over a mold that represents a hemisphere the balloon. A heater (e.g., a 4520 watt infrared heater) can be used to form the material, and a vacuum can be pulled. The material, with slack put in it prior to vacuum being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the thermoforming process is trimmed. On a multi-layer film, the sealing layer, a PE or similar layer is bonded to the sealing layer of the second film half. To do this the film of the hemisphere that has the nylon exposed to the external environment is folded up along the edges of the sphere on one half such that it can be bonded to the hemisphere with the polyethylene on the outermost layer.

The two film pieces are then sealed using a roller bonder or a band heater. In the roller bonder, the air provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon due to gastric motility forces, (2) over inflation of the balloon due to increased internal pressure of the balloon from uptake of the gastric environment of the gasses and water vapor and (3) under inflation of the balloon that leads to fatiguing of the excess material and subsequent puncture of the balloon. By managing these two variables and tuning these variables to withstand the dynamic gastric environment, the balloon system can be tailored to ensure it remains inflated throughout its useful life. Instances of spontaneous deflation in this intragastric balloon can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon to be controlled. This method allows for a tunable method for prevention of under inflation and over inflation.

Another phenomenon seen with gastric balloons and obesity in general is stomach accommodation. In the process of stomach accommodation, the stomach grows to accommodate the space occupying device or excess food that is ingested. In the process of stomach accommodation, the volume of a stomach containing an intragastric balloon grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon from the gastric environment, the balloon can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach into the duodenum). Stomach gas usually arises from swallowing air during eating. The composition of air is nitrogen ($N_2$) 78.084%; oxygen ($O_2$) 20.9476%; argon (Ar) 0.934%; carbon dioxide ($CO_2$) 0.0314%; neon (Ne) 0.001818%; methane ($CH_4$) 0.0002%; helium (He) 0.000524%; krypton (Kr) 0.000114%; hydrogen ($H_2$) 0.00005%; and xenon (Xe) 0.0000087%.

Five gases constitute greater than 99% of the gases in gastrointestinal system: $N_2$, $O_2$, $CO_2$, $H_2$ and methane, with nitrogen predominating. Gastric $pCO_2$ closely parallels local (splanchnic) arterial and draining venous blood $pCO_2$ values. Neutralization of stomach acid can also generate gas. For example, when the stomach acid reacts with bicarbonates (e.g., as are present in certain antacids) in the digestive juices, the chemical process creates $CO_2$, which is normally absorbed into the blood stream. Digestion of food in the intestines, mainly through fermentation by colonic bacteria, generates $CO_2$, $H_2$, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

In certain embodiments, it is preferred that the composition of the initial fill gas is substantially characteristic of the composition of the mixture of gases in the in vivo gastric environment. Such an initial fill gas can include only $N_2$ and $CO_2$, or can include only $N_2$, $CO_2$, and $O_2$, or can include $N_2$ and $CO_2$ as well as one or more other gases present in the in vivo environment (e.g., water vapor, $H_2$, $CH_4$, Ar, $H_2S$, or $NH_3$). Argon or another inert gas (or inert gases) can be substituted in part or in whole for $N_2$, which is considered an inert gas in the context of the preferred embodiments. In those embodiments wherein the fill gas includes only $N_2$ or $CO_2$, it is preferred that the initial fill gas comprises from about 75% v/v to about 96% v/v $N_2$, from about 5% v/v to about 15% (vol.) $O_2$, and from about 1% v/v to about 10% v/v $CO_2$, more preferably from about 80% (vol.) to about 85% (vol.) $N_2$, from about 5% (vol.) to about 13% (vol.) $O_2$, and from about 4% (vol.) to about 8% (vol.) $CO_2$. In those embodiments wherein the fill gas includes only $N_2$ or $CO_2$, it is preferred that the initial fill gas comprises from about 4% (vol.) to about 8% (vol.) $CO_2$, with the remainder $N_2$ or another inert gas. In embodiments wherein the initial fill gas comprises other gases in addition to $CO_2$ and the inert gas(es), it is preferred that the initial fill gas comprises from about 4% (vol.) to about 8% (vol.) $CO_2$.

Controlled self-inflation of the intragastric balloon in the in vivo environment can be achieved by using a semipermeable or permeable composite wall in the balloon and initially filling the balloon with a preselected single gas, such as $N_2$ or $O_2$. The balloon utilizes differences in concentrations of gases and water concentration differences between the internal balloon environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon than to other gases present in the in vivo gastrointestinal environment. For example, if nitrogen gas is employed as the inflation gas, over time in the in vivo environment, the volume and/or pressure in the balloon will decrease as nitrogen diffuses out into the in vivo environment through the oxygen permeable wall. Similarly, if oxygen gas is employed as the inflation gas, over time in the in vivo environment, the volume and/or pressure in the balloon will decrease as oxygen diffuses out into the in vivo environment through the oxygen permeable wall. The differential in partial pressure of the single gas in the balloon (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon than to other gases present in the in vivo gastrointestinal environment. For example, if nitrogen gas is employed as the inflation gas, over time in the in vivo environment, the volume and/or pressure in the balloon will increase as $CO_2$, and all of the other gases present in the gastric environment, diffuse into the balloon through the $CO_2$ permeable wall. The differential in partial pressure of the permeable gas in the balloon (lower) versus the in vivo environment (higher) will drive the process until equilibrium is reached.

In addition, maintaining and/or controlling inflation of the balloon can also be done using the differences in concentrations between the internal balloon environment and external gastric environment in which the balloon volume/pressure can be increased or decreased as needed to extend the useful life of the product. One reason to decrease the pressure can be to first inflate the balloon with a large, but highly diffusible/soluble gas molecule such as $CO_2$ in addition to a more inert gas like nitrogen to pre-stretch the balloon, with the soluble gas diffusing out of the balloon and other gases not originally present in the balloon migrating in to fill the balloon.

Inflation gases can be selected to start with the majority of the gas in the balloon comprising a large, inert gas or a gas that has low diffusivity through the selected composite wall. Examples of inert gases include but are not limited to nitrogen, as well as $SF_6$, $C_2F_6$, $C_3F_8$, $C_4F_{10}$, $C_4F_8$, $C_4F_8$, $C_3F_6$, $CF_4$, and $CClF_2$—$CF_3$. An inert gas in conjunction with a less inert gas(es) that are more soluble in the gastric environment, can be combined to comprise the starting balloon inflation gas composition where the inert gas would be in excess to the more soluble/diffusible gas. In certain embodiments, it is preferred to combine nitrogen as a more soluble/diffusible gas with a gas of lower diffusivity/solubility such as $SF_6$, $C_2F_6$, $C_3F_8$, $C_4F_{10}$, $C_4F_8$, $C_4F_8$, $C_3F_6$, $CF_4$, and $CClF_2$—$CF_3$. For example, a fill gas of certain embodiments can comprise 5% (vol.) of the more soluble/diffusible inert gas in combination with 95% (vol.) of the less soluble/diffusible inert gas (e.g., 5% $N_2$ in combination with 95% $SF_6$); or 10% of the more soluble/diffusible inert gas in combination with 90% of the less soluble/diffusible inert gas (e.g., 10% $N_2$ in combination with 90% $SF_6$); or 15% of the more soluble/diffusible inert gas in combination with 85% of the less soluble/diffusible inert gas (e.g., 15% $N_2$ in combination with 85% $SF_6$); or 20% of the more soluble/diffusible inert gas in combination with 80% of the less soluble/diffusible inert gas (e.g., 20% $N_2$ in combination with 80% $SF_6$); or 25% of the more soluble/diffusible inert gas in combination with 75% of the less soluble/diffusible inert gas (e.g., 25% $N_2$ in combination with 75% $SF_6$); or 30% of the more soluble/diffusible inert gas in combination with 70% of the less soluble/diffusible inert gas (e.g., 30% $N_2$ in combination with 70% $SF_6$); or 35% of the more soluble/diffusible inert gas in combination with 65% of the less soluble/diffusible inert gas (e.g., 35% $N_2$ in combination with 65% $SF_6$); or 40% of the more soluble/diffusible inert gas in combination with 60% of the less soluble/diffusible inert gas (e.g., 40% $N_2$ in combination with 60% $SF_6$); or 45% of the more soluble/diffusible inert gas in combination with 55% of the less soluble/diffusible inert gas (e.g., 45% $N_2$ in combination with 55% $SF_6$); or 50% of the more soluble/diffusible inert gas in combination with 50% of the less soluble/diffusible inert gas (e.g., 50% $N_2$ in combination with 50% $SF_6$). In certain embodiments, an initial fill gas consisting of 20% of the less soluble/diffusible inert gas with the remainder a more soluble/diffusible inert gas is employed; or an initial fill gas consisting of 19-21% of the less soluble/diffusible inert gas with the remainder a more soluble/diffusible inert gas is employed; or an initial fill gas consisting of 18-22% of the less soluble/diffusible inert gas with the remainder a more soluble/diffusible inert gas is employed; or an initial fill gas consisting of 17-23% of the less soluble/diffusible inert gas with the remainder a more soluble/diffusible inert gas is employed; or an initial fill gas consisting of 16-24% of the less soluble/diffusible inert gas with the remainder a more soluble/diffusible inert gas is employed; or an initial fill gas consisting of 15-25% of the less soluble/diffusible inert gas with the remainder a more soluble/diffusible inert gas is employed. For example, an initial fill gas comprising 18-20% $SF_6$ with the remainder as nitrogen can be employed, or 19-21% $SF_6$ with the remainder as nitrogen; or 18-22% $SF_6$ with the remainder as nitrogen; or 17-23% $SF_6$ with the remainder as nitrogen; or 16-24% $SF_6$ with the remainder as nitrogen; or 15-25% $SF_6$ with the remainder as nitrogen.

Patient diet and medications can also affect/control balloon inflation status—primarily by $CO_2$ concentration effects produced in the gastric environment. In addition, gastric pH also affects $CO_2$ concentration. This particular method can also allow for a greater degree of tuning of the device's useful life based on the composite wall material, e.g., barrier/non-barrier and whether the gas that diffuses in is maintained longer in the balloon if it has a barrier wall versus a non-barrier wall. This particular form of self-inflation can be employed using a self-inflating gastric balloon (e.g., initially inflated by a gas generating reaction in the balloon initiated after swallowing), or an inflatable gastric balloon (e.g., inflated using a catheter, with or without endoscopic assistance, delivered nasogastrically or any other delivery method). The method can be used with any gastric balloon, including swallowable balloons and balloons placed in the stomach by, e.g., endoscopic methods. The method is particularly preferred for use in connection with intragastric devices; however, it can also be applied to use in, e.g., pulmonary wedge catheters and urinary incontinence balloon devices. The advantages to this technology include the ability to compensate for stomach accommodation, allowing the balloon to adapt to a stomach that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In a particularly preferred embodiment, used in connection with a suitable inert gas such as $SF_6$ and/or $N_2$ (with or without $CO_2$ as an additional inflation gas) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low Density Polyethylene+Low Density Polyethylene (also referred to as co-extruded Nylon 12-encapsulated PVDC-Nylon 12-LLDPE+LDPE multilayer). Another particularly preferred configuration is a co-extruded multi-layer Nylon 12/Linear Low Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Automatic Deflation of Intragastric Balloon Systems

The self-inflating (also referred to as automatic inflating) or inflatable (also referred to as manually inflating) intragastric balloon is provided with mechanisms to reliably control timing of deflation. In preferred embodiments, the balloon auto-deflates and passes through the stomach, through the lower gastrointestinal tract, and out of the body at the end of its pre-determined useful life (non-spontaneous), preferably between 30 and 90 days but can be timed to deflate within 6 months. In the preferred embodiments described below, the timing of deflation can be accomplished via the external gastric environment (by conditions of temperature, humidity, solubility, and/or pH, for example) or via the environment within the lumen of the inflated balloon. It is preferable for consistency to control the initiation of the self-deflation process by manipulating the internal balloon environment.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(es) are of sufficient size to ensure opening of a sufficient surface area to cause rapid deflation, and to prevent re-inflation by seepage of stomach fluid into the balloon. The balloon patch(es) comprise materials that can be applied to the balloon such that a substantially smooth surface is maintained, and preferably comprise a single layer or multi-layered material. The patch(es) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PB SA), aromatic copolyesters (PBAT), poly (lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar fluid retention barrier film or the same film as the remaining wall of the balloon which is adhered to the balloon using a weak adhesive, or welded or adhered such that after a specified amount of time the patch delaminates from the applied area and allows for an opening for inflation fluid release for deflation. Or if deemed necessary for rapid deflation the entire balloon composite wall can be made of the erodible material. The mechanism of using an erodible material or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for fluid release and subsequent deflation of the balloon. Mechanical additions that can be used in conjunction with a plug include a degradable/erodible/disintegrable material that holds a plug (e.g., of a non-degradable or degradable material) in place or a compressed spring housed within the retaining structure or plug structure. More specifically one preferred embodiment to achieve deflation can comprise a housing, a radial seal, a solid eroding core, and a protective film attached to the external surface of the eroding core. The inside of the eroding core is exposed to the internal balloon liquid. The core creates a compressive force that holds the seal against the housing. As the core erodes, the compression between the housing and the radial seal is reduced until there is clearance between the housing and the seal. Once there is clearance, gas can move freely from the inside of the balloon to the outside environment. The seal can fall out of the housing and into the balloon. The diameter, length, and material types can be adjusted in order to create the deflation at a desired time point. Example materials for each component used to achieve this deflation mechanism can be as follows: Housing: Biocompatible structural material, capable of withstanding enough radial force to form an air tight seal. Possible materials include: polyethylene, polypropylene, polyurethane, UHMWPE, titanium, stainless steel, cobalt chrome, PEEK, or nylon; Radial Seal: The radial seal needs to be composed of a biocompatible elastic material, capable of providing liquid and gas barrier to acidic environments. Possible materials include: silicon, polyurethane, and latex; Eroding Core: The eroding core needs to be a material capable of breaking down at a predictable rate at given environmental conditions. Possible materials include: PLGA, PLA, or other polyanhydrides that are capable of losing integrity over time or any materials listed above that provide erodible characteristics.

For the spring mechanism, once the material degrades, the spring is released and/or the plug/septum is pulled into the balloon or pushed out of the balloon, thus releasing fluid once an orifice has been created by release of the spring mechanism and pushing out or pulling in of the plug.

Another preferred embodiment is comprised of a septum, moisture eroding material inside an inlet port, and moisture absorbing expansion material. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired timepoint, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

In certain embodiments, the balloon can incorporate one or more plugs in the wall of the balloon that contain a compressed pellet or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient pressure is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

In certain embodiments, a balloon composed of a septum, moisture eroding material inside an inlet port, and moisture absorbing expansion material is employed. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired time point has been reached, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Another mechanism for self-deflation is to create a forced de-lamination scheme, which can provide a larger surface area to ensure rapid deflation. In, e.g., a balloon having a tri-layer wall, the outermost layer is substantially strong enough to hold the inflation fluid (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time. This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

In another embodiment providing abrupt deflation of the balloon after a desired period of time has elapsed, the composite wall of the entire balloon or a section of the composite wall (patch) includes several material layers that are slowly penetrated by water that has been injected inside the balloon during the manufacturing process or during the inflation process. This water penetrates through the layers, eventually reaching a material that substantially expands, rupturing a thin external protective later, and creating a large hole for gas to escape and the balloon to deflate. The water expanding material is protected from liquid via a coating or sheath, such as parylene, which allows a controllable amount of moisture exposure. Once water reaches the expansion material, it exerts a force on the protective outer layer, causing it to rupture. The outer layer may be created with a weakened bonding area, a partially scored area, or other methods of ensuring a desired rupture location and to facilitate desired timing for auto-deflation to take place. There can be any number of layers between the moist environment and the moisture expanding center. Each material layer can have different erosion rates (e.g., fast or slow)

and can be selected by the predetermined time deflation is desired to occur (e.g., after 30 days, 60 days, or more). By varying the number, thickness, and rate of each of the circumferential layers, the time to deflation can be accurately controlled.

Alternatively a pressure sealing button that is adhesively bonded over a perforation in the balloon material can be provided for deflation. The adhesive bonding the button erodes over time when it comes into contact with moisture derived from the gastric fluid or that has been injected inside the balloon. Once the adhesive can no longer bond and create an airtight seal between the adhesive and the button, the balloon will rapidly deflate. By controlling the hole size and moisture exposure of the adhesive, the erosion time can be accurately predicted.

Deflation can also be facilitated by creating a series of connecting ports within the septum or on another similar structure attached to the balloon composite wall. The ports can be constructed using a water- or acid-dissolving, biologically compatible, low permeability substance, such as gelatin. The diameter of the hole, number of holes, channel width, and channel length can all be adjusted to control the dissolving parameters. Once the material in the ports and channel is dissolved, there is a clear path for gas trapped in the balloon to escape, eventually resulting in a deflated balloon. The water can be gastric fluid or controlled internally by including water inside the balloon at assembly or during the inflation process. There can be a plurality of port openings to guarantee gas transmits. Additionally, there are several variables that can be adjusted to control dissolution time: size of the port openings; number of port openings; the length of the internal channel; the width of the internal channel; and the rate of material dissolution. The port/channel layout design can ensure that only a small amount of surface area is exposed to moisture at any particular time, thereby controlling the rate of erosion and ultimately deflation.

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams." One seam that breaks the balloon open into (at a minimum) two halves, or more seams are provided so that a plurality of smaller balloon pieces is produced in the dissociation reaction. The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that can affect erosion timing is minimized. The internal balloon environment can be manipulated by adding excess water at injection to create a more humid internal environment, or the amount of constituents added can be varied to manipulate the pH, etc.

Confirmation of Deflation of Intragastric Balloon Systems

Whether the balloon is self-deflating or non self-deflating, various mechanisms may be implemented to confirm deflation of the balloon. In preferred embodiments, the balloon deflates and emits a sensory stimulant that is configured to trigger a response by one of the patient's senses. In some embodiments, the device may emit an odor that is smelled by the patient. In some embodiments, the device may emit a taste that is tasted by the patient. In some embodiments, the device may emit a coloring agent that the patient can visually see after passing the agent, for example in a toilet. In some embodiments, the sensory stimulant may cause a physiological response indicative of deflation. For example, the deflated balloon may emit a substance that encourages passage through the bowels.

In some embodiments, flavorants may be used to indicate deflation to the patient. Theses may be the same or different as the flavoring agents that may be used in some embodiments, for example with the ingestible event markers for a voltaic or pH based locating system. Thus, flavorants such as peppermint, oil of wintergreen, cherry flavoring or the like can also be used. Additionally, it may be desirable to add a coloring agent to make the dosage form more attractive in appearance or to help identify the product.

Optical Tracking and Visualization Subcomponents

Tracking and visualization functionality can be incorporated into devices and systems described above or can be incorporated into one or more separate devices. As used herein, "visualization" is used broadly to refer to identifying an item of interest in the body in a number of ways, including by electromagnetic radiation data such as quantity of visible light, change in quantity of visible light, and other attributes of visible light that may be used to facilitate tracking, locating, identifying, and characterizing a visible light source, as well as audio, visual, tactile, or other output based on the visible light data that characterizes the light source or the relationship between the light source and a volume-occupying device when the light source is separate from the volume-occupying device. Due to the non-invasive nature of the present intragastric volume-occupying device, physicians may desire to determine, or confirm, the location and orientation of the volume-occupying device prior to inflation, during the course of treatment, or after deflation. Accordingly, intragastric systems and devices are provided that incorporate visible light components configured for enabling determining and confirming the location, orientation and state of an intragastric balloon device at one or more phases of administration.

This section discusses optical components that may be implemented in the electromagnetic embodiments described herein.

Markers

A light-emitting marker component may comprise a variety of materials or objects that produce visible light. Visible light generally refers to waves in the electromagnetic spectrum having wavelengths between about 380 nm and about 700 nm. In some embodiments a light-emitting marker may produce wavelengths in the ultraviolet range or near-ultraviolet range. The ultraviolet range can generally refer to wavelengths between about 400 nm and about 10 nm. The near-ultraviolet range can generally refer to wavelengths between about 400 nm and about 300 nm. In some embodiments, a light-emitting marker produces wavelengths in the infrared range or near-infrared range. The infrared range can generally refer to wavelengths between about 700 nm and about 1 mm. The near-infrared range can generally refer to wavelengths between about 700 nm and about 2,500 nm.

One or more light-emitting markers may be implemented in the optical intragastric volume-occupying device locating system with optical sensors or detectors. The light-emitting markers comprise any light-emitting substance, material, or object, to which the sensors or detectors are responsive. The optical intragastric volume-occupying device locating system may use any light source capable of generating visible light. In some embodiments, the optical intragastric device locating system includes a high intensity LED light source, which can include one or more LED lights. However, any type of light source or lights capable of producing visible light may be used. In some embodiments, the optical intragastric volume-occupying device may use any light source capable of generating ultraviolet, near-ultraviolet, infrared, or near-infrared light.

In some embodiments, a light source includes one or more RGB LEDs. An RGB LED includes one red LED, one green LED, and one blue LED, each of which can be attenuated to produce a variety of spectral colors, as well as white light. In some embodiments, a light source can include one or more white LEDs (WLEDs). A WLED can be an RGB LED configured to produce white light or a short-wavelength LED used in combination with phosphor materials. For example, a blue LED, near-ultraviolet LED, or ultraviolet LED can be used in combination with phosphors to produce light that appears white. For example a blue LED having a blue light-emitting indium gallium nitride (InGaN) die can be combined with a yellow phosphor, such as for example, a yttrium aluminum garnet (YAG) or silicate phosphor coating, to cause emitted light to appear white. In some embodiments, a near-ultraviolet or ultraviolet LED can be combined with a RGB phosphor to produce light that appears white. Other phosphors that can be used with an LED include lutetium aluminum garnet (LuAG), red nitrides, and green aluminates. A light source can also include one or more organic light-emitting diodes (OLEDs), one or more quantum dot LEDS, one or more red LEDs, one or more blue LEDS, one or more green LEDs, one or more infrared LEDs, one or more ultraviolet LEDs, and/or one or more near-ultraviolet LEDs. A light source can include LEDs emitting light throughout the ultraviolet, near-ultraviolet, visible, near-infrared, or infrared spectrum. In some embodiments, one or more LEDs may emit light between about 380 nm to about 700 nm, from about 10 nm to about 400 nm, about 10 nm to about 400 nm, about 300 nm to about 400 nm, about 700 nm to about 2,500 nm, about 700 nm to about 1 mm, about 400 nm to about 450 nm, about 450 nm to about 500 nm, about 500 nm to about 570 nm, about 570 nm to about 590 nm, about 590 nm to about 610 nm, or about 610 nm to about 760 nm. In some embodiment one or more LEDs may emit light less than about 400 nm, less than about 380 nm, greater than about 700 nm, or greater than about 760 nm. A light source may include LEDs having one or more of the following semiconductor materials: gallium arsenide, aluminum gallium arsenide, gallium arsenide phosphide, aluminum gallium indium phosphide, gallium (III) phosphide, aluminum gallium phosphide, indium gallium nitride, gallium(III) nitride, zinc selenide, silicon carbide, diamond, boron nitride, aluminum nitride, aluminum gallium nitride, and aluminum gallium indium nitride.

In some embodiments, a light source can include one or more low power lasers. For example, a light source may include on or more laser diodes. A low power laser may have a power of less than 1 mw, less than 5 mw, less than 10 mw, between 1 mw to 5 mw, between 1 mw to 10 mw, between 5 mw to 10 mw, or greater than 10 mw. Laser diodes can be configured to emit light between about 375 nm, to about 3,500 nm. In some embodiments, one or more laser diodes may emit light between about 380 nm to about 700 nm, from about 10 nm to about 400 nm, about 10 nm to about 400 nm, about 300 nm to about 400 nm, about 700 nm to about 2,500 nm, about 700 nm to about 1 mm, about 400 nm to about 450 nm, about 450 nm to about 500 nm, about 500 nm to about 570 nm, about 570 nm to about 590 nm, about 590 nm to about 610 nm, or about 610 nm to about 760 nm. In some embodiment one or more laser diodes may emit light less than about 400 nm, less than about 380 nm, greater than about 700 nm, or greater than about 760 nm. In some embodiments, a light source may include one or more visible lasers.

In some embodiments, a light source can configured to prevent thermal burns from contact with the light source or a material or component encapsulating the light source. Thermal burns can occur at temperatures above about 44° C. over an exposure period of about 5-6 hours. The time required for a thermal burn increases as temperature increases. At a temperature of about 65° C., a thermal burn may occur in about 2 seconds. In some embodiments, a highest temperature of a light source may be less than 44° C., less than 45° C., less than 46° C., or less than 47° C. In some embodiments, a material or component, such as a capsule, encapsulating the light source has insulating properties to prevent a high temperature region from contact with the body when positioned therein. Emitted light may also damage tissue based on one or more of the amount of power or energy emitted, the wavelength of the light, the amount of exposure time, the distance between the light source and the tissue, and the width of a beam of light. The light source can be configured to prevent tissue damage due to radiating light. For example, a light source may emit continuous light with a power of less than 0.5 W within a wavelength range between 315 nm to 2,500 nm. In some embodiments, a light source may emit pulsed light at an energy of less than 30 mJ within a wavelength range between 400 nm to 700 nm. In some embodiments, a light source may emit light at a power of less than 1 mw, less than 5 mw, less than 10 mw, between 1 mw to 5 mw, between 1 mw to 10 mw, between 5 mw to 10 mw, or greater than 10 mw.

In some embodiments, the light source may be configured to radiate through fluid in the stomach, such as for example stomach acid, water, and any liquid ingested by a user, or any other stomach contents, such as, for example, food particles. Radiation of emitted light through liquid may depend on one or more the color of emitted light, the power or energy of emitted light, and the width of a beam of light. Short wavelengths may be preferable in penetrating liquid, such as water, over greater depths. In some embodiments, a light source emits blue light, light having a wavelength between about 450 nm to about 495 nm. A light source may also emit green light, light having a wavelength between about 49 nm to about 570 nm, or violet light, light having a wavelength between about 380 nm to about 450 nm. In some embodiments, the light source is configured to emit white light, which includes a combination of different wavelengths in the visible light range.

A light source can be configured to emit light in one or more directions. In some embodiments, a light source can be configured to emit light radially outward in all directions or nearly all directions from a center point of the light source. In some embodiments a light source can be configured to radiate one or more beams of light in one or more particular directions. In some embodiments, a light source can be configured to illuminate less than 25% of the stomach, less than 50% of the stomach, less than 75% of the stomach, greater than 75% of the stomach, between 25% and 50% of the stomach, between 50% and 75% of the stomach, or between 75% and 100% of the stomach. In some embodiments, the light source is configured to float on top of liquid in the stomach. The light source can be configured to emit light into the non-fluid filled portion of the stomach. For example, the light source can be configured to emit light radially outward in a horizontal or vertically upward direction.

In certain embodiments, one or more light-emitting markers may be affixed to or incorporated into the materials of the intragastric volume-occupying device, the delivery components, or the inflation assembly. For example, one or more light-emitting markers may be affixed to a volume-occupying device catheter, such as an inflation catheter. In other embodiments, one or more light-emitting markers can be incorporated into a separate swallowable device, such as a swallowable capsule or catheter.

In some embodiments, one or more light-emitting markers are positioned on the intragastric volume-occupying device such that light emitted from the light-emitting markers is shielded in at least one direction when the intragastric volume-occupying device is in its deflated state and such that the light emitted from the light-emitting markers is unshielded upon inflation of the intragastric volume-occupying device.

In some embodiments, one or more light-emitting markers can be part of an electronics package containing a plurality of electronics components such as a printed circuit board, a battery and a power switch. The light-emitting markers may be activated by the power switch. In some embodiments, the power switch can be activated based on environmental conditions, such as for example, contact with stomach acid. Alternatively, the power switch may be manually activated prior to insertion of the marker into the body. In some embodiments, the power switch may be connected to a timer, wherein activation of the power switch is initiated after a predetermined amount of time. The electronics package may further include a wireless transmitter for communication with one or more external devices. In some embodiments, the power switch may be activated wirelessly or through a wired connection following introduction into the body.

In embodiments in which one or more light-emitting markers are incorporated into a separate swallowable device, the one or more light-emitting markers may be positioned within the interior of the separate swallowable device. The separate swallowable device may be transparent or semi-transparent or can include one or more transparent or semi-transparent sections to allow for light to radiate out of the separate swallowable device. Alternatively, the one or more light-emitting markers may be affixed to the exterior of the separate swallowable device. The separate swallowable device may further include one or more additional components of the intragastric device locating system, such as for example, an electronics package.

In certain embodiments, the separate swallowable device is a clear polymer capsule. However, any biocompatible material may be used. The capsule can house a one or more light-emitting markers located within the interior of the capsule.

In some embodiments, the one or more light-emitting markers can be positioned within the capsule so that light radiates out of the capsule in all or substantially all directions. In some embodiments, the one or more light-emitting markers can be positioned to radiate light out of one or more particular sections of the capsule. For example, the light-emitting markers can be positioned so that light radiates out of less than 25% of the capsule, less than 50% of the capsule, less than 75% of the capsule, greater than 75% of the capsule, between 25% and 50% of the capsule, between 50% and 75% of the capsule, or between 75% and 100% of the capsule. In some embodiments, the capsule can be shaped or weighted so that light is emitted in one or more particular directions in the stomach. For example, a capsule may have a weight in a lower section such that the lower section is positioned in contact with the fluids in the stomach when inserted therein. One or more light-emitting markers can be positioned so as to radiate light out of an upper section of the capsule in a direction at least partially away from the weight and/or fluid.

One or more of a printed circuit board, a battery, and a power switch may further be positioned on the interior of the capsule and connected to the light-emitting markers. In some embodiments, the power switch may be positioned on the exterior of the capsule, or extending out of the capsule. In some embodiments, the capsule is configured to be passed through the body naturally after placement in the stomach.

In certain embodiments, the separate swallowable device is lubricated or otherwise treated so as to facilitate swallowing. For example, the separate swallowable device may be wetted, heated, or cooled, prior to swallowing by the patient. Alternatively, the separate swallowable device may be dipped in a viscous substance that will serve to lubricate the device's passage through the esophagus. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the separate swallowable is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the separate swallowable may be weighted at a certain end in order for it to be oriented appropriately when it is administered, as it travels down the esophagus, and/or when it is in the stomach. The weighting components may include polymer materials.

Optical Detection

It is envisioned that the light-emitting marker may be incorporated into the intragastric volume-occupying device locating system to facilitate various optical location systems comprising a variety of methods and apparatuses for sensing and detecting an optical marker.

In some embodiments, the optical location system uses one or more optical sensors configured to detect light and convert the detected light to an electronic signal. Embodiments of optical sensors can include, but are not limited to photoconductive devices, photovoltaic devices, photodiodes, phototransistors, reflective sensors, optical position sensors, ambient light sensors, or any other sensors capable of detecting light or changes in light.

In some embodiments, one or more optical sensors may be affixed to or incorporated into the materials of the intragastric volume-occupying device, the delivery components, or the inflation assembly. For example, one or more optical sensors may be affixed to a volume-occupying device catheter, such as an inflation catheter. In other embodiments, one or more optical sensors can be incorporated into a separate swallowable device, such as a swallowable catheter or capsule.

In certain embodiments, the optical location system uses an optical sensor coupled with the intragastric volume-occupying device and one or more light-emitting markers coupled with a separate device such as a swallowable catheter or capsule. With the swallowable catheter or capsule positioned within the stomach, the intragastric volume-occupying device can be introduced into the body. As the intragastric volume-occupying device travels through the body, the optical sensor can detect a quantity of light or change in quantity of light. When a particular threshold light measurement is reached, it can be inferred that the volume-occupying device is positioned within the stomach.

In alternative embodiments, the optical location system using a light-emitting marker coupled with the intragastric volume-occupying device and an optical sensor coupled with a separate device such as a swallowable catheter or capsule. With the swallowable catheter or capsule positioned within the stomach, the intragastric volume-occupying device can be introduced into the body. As the intragastric volume-occupying device travels through the body, the optical sensor can detect a quantity of light. When a particular threshold light measurement is reached, it can be inferred that the volume-occupying device is positioned within the stomach.

In certain embodiments, the optical location system further includes one or more optical fibers. The one or more optical fibers can be coupled at a first end with the intragastric volume-occupying device or with a separate device such as a swallowable catheter or capsule. The second end of the optical fibers can be coupled with an optical sensor such that light entering the first end of the optical fibers can be transmitted to the second end of the optical fibers and detected by the optical sensor. This can allow the optical sensor to be located externally to the body or to the stomach. In certain embodiments, the one or more optical fibers can be affixed to or incorporated into the materials of the intragastric volume-occupying device, the delivery components, or the inflation assembly. In other embodiments, the one or more optical fibers are located within a catheter coupled to the intragastric volume-occupying device, such as the inflation catheter described above. Alternatively, the one or more optical fibers can be affixed to or incorporated into one or more separate devices, such as a swallowable catheter or capsule.

A computing system may be implemented in the optical location system. The computing system comprises hardware and software that receives data from the optical sensor and calculates information related to the location, orientation, and/or state of an intragastric volume-occupying device according to certain algorithms.

In some embodiments, the hardware may comprise a central processing unit, memory, an analog to digital converter, analog circuitry, and a display.

In some embodiments, the software proceeds through a number of steps including calibration, initialization, prediction, estimation, measuring optical sensor data, calculating various desired outputs including location, orientation, size, and configuration.

In some embodiments, the computing system predicts or estimates a location, position, orientation, state, or configuration of a light-emitting marker and determines a corresponding estimated or predicted location, position, orientation, state, or configuration of a volume-occupying intragastric device. In some embodiments, the computing system determines that an optical sensor has detected a measurement exceeding a predefined threshold measurement, and based on the detected measurement exceeding the predefined threshold measurement, determines that a volume-occupying device is positioned within a patient's stomach.

In embodiments using estimation or prediction, the computation may be done using iterative calculations and/or neural networks, and the hardware may further include an estimation processor.

The processor's output relating to the location, orientation and/or state of an intragastric volume-occupying device may be communicated to a user in a number of manners. In some embodiments, the output is shown visually on a display.

In some embodiments, the processor's output related to an intragastric volume-occupying device's location, orientation, and/or state is audibly communicated to a user through a speaker.

In some embodiments, the processor's output related to an intragastric volume-occupying device's location, orientation, and/or state is communicated to a user through a combination of methods. For instance, the system may employ a visual graphical display with audible alerts sent through speakers.

In some embodiments, the optical location system is calibrated before use. The light-emitting marker and the optical sensor are positioned in pre-planned locations and orientations to verify the output signal is within an expected range or exceeds an expected threshold measurement.

In some embodiments, the optical location systems are calibrated or otherwise verified using a human patient simulator, or dummy, to test the optical location system as an intragastric volume-occupying device travels through the simulators.

The intragastric volume-occupying devices once ingested may be located using the optical location system.

The orientation of the devices once ingested may be ascertained using the optical location system.

Further, the various sizes and configurations of the devices once ingested may be characterized using the optical location system. For instance, inflation of a balloon, or the inflation or configuration of multiple balloons, may be characterized and assessed.

The optical location system may also be used in conjunction with a deflating system to characterize the deflation process.

The timing and other attributes of the various methods of administration can be characterized using the disclosed optical location system. Whether the device is administered using endoscopic techniques or orally, the progress of the device as it makes its way to the stomach can be tracked with the optical location system. For instance, the effects of swallowing the device with hard gelatin or water or other consumables may be characterized by tracking the location and orientation as it is ingested.

FIG. 1 depicts an embodiment of a part of an optical location system for locating a light-emitting marker. The system includes a balloon capsule 100, a catheter 105, a connector 110, a light sensor 115, and a balloon valve 120. Preferably, the balloon capsule 100 is non-toxic, does not cause sensitization, and is non-irritating. A distal end 106 of the catheter 105 extends through a proximal end 104 of the balloon capsule 100 into the interior of the balloon capsule 100 and connects to the balloon valve 120. A proximal end 108 of the catheter 105 is connected to a distal end of the connector 110. The proximal end of the connector 110 is connected to the light sensor 115. At least one optical fiber extends along the length of the interior of the catheter 105 and through the valve 120 such that a distal end of the optical fiber is positioned at a distal end 102 of the balloon capsule 100 when the catheter 105 is placed within the balloon capsule 100, and such that a proximal end of the optical fiber can be received by the light sensor 115. In some embodiments, the optical fiber may have a diameter of about 0.006 inches. The diameter of the optical fiber may be between less than 0.0001 inches to greater than 0.01 inches. In some embodiments, the diameter of the optical fiber can be between 0.0001 inches to 0.0005 inches, 0.0005 inches to 0.001 inches, 0.001 inches to 0.002 inches, 0.002 inches to 0.003 inches, 0.003 inches to 0.004 inches, 0.004 inches to 0.005 inches, 0.005 inches to 0.006 inches, 0.006 inches to 0.007 inches, 0.007 inches to 0.008 inches, 0.008 inches to 0.009 inches, or 0.009 inches to 0.010 inches. The catheter 105 may be a small 2 Fr diameter catheter. The catheter can be a flexible, hydrophilic coated, 2-Fr catheter which contains a swallowable catheter (approximately 30 inches) which is bonded to approximately 40 inches of pellethane extension tubing to allow connection to the light sensor 115.

The distal end of the optical fiber is exposed at the distal end 102 of the balloon capsule 100. In operation, light radiating into the distal end of the optical fiber can then transmit to the proximal end of the optical fiber, where it can be detected by the light sensor 115. The light sensor 115 can include any optical detector or power meter capable of detecting light, such as, for example, photoconductive devices, photovoltaic devices, photodiodes, phototransistors, reflective sensors, optical position sensors, and ambient light sensors.

In some embodiments the light sensor 115 can be configured to detect light in the visible light range. The light sensor 115 can also be configured to detect light in the ultraviolet range, near ultraviolet range, infrared range, and near infrared range.

In some embodiments, the light sensor 115 can detect the amount of light energy received at the distal end of the optical fiber. In other embodiments, the light sensor 115 can detect a change in the amount of light energy received at the distal end of the optical fiber. The light sensor 115 can then convert the amount of light energy detected or change in amount of light energy detected to an electrical signal. In some embodiments, the light sensor 115 can amplify and digitize the electrical signal. The light sensor 115 can further include a processor configured to determine, based on the electronic signal, an amount of light energy or change in amount of light energy received at the distal end of the optical fiber. In some embodiments, the processor can further determine if the amount of light energy or change in amount of light energy received at the distal end of the optical fiber exceeds a predefined threshold limit. The sensor 115 may also be connected, through a wired or wireless connection to one or more external devices, such as, for example, computing devices or mobile devices. The light sensor 115 may include a sensor interface unit configured to electrically communicate with one or more of optical detectors, light-emitting markers or light-emitting devices, and external electronic devices. In some embodiments, one or more external devices can amplify and digitize the electrical signal. In some embodiments, data from the light sensor 115 is processed at the external devices. The light sensor and/or external devices may further include a memory for storage of date detected by the light sensor 115. The light sensor 115 and/or external devices may further include a display for displaying information related to the measurements detected by the light sensor 115. For example, the display may be configured to display a measurement of a quantity of light detected or a measurement of a change in quantity of light detected. The display can also be configured to display whether a quantity of light detected or change in quantity of light detected is below or above a predefined threshold.

In some embodiments, the balloon capsule 100 or a portion of the balloon capsule 100 may be transparent or semi-transparent in order to receive light into the interior of the balloon capsule. Similarly, the catheter 105 or a portion of the catheter 105 may be transparent or semi-transparent in order to receive light into the interior of the catheter 105, where it may reach the distal end of the optical fibers.

Figure 2:
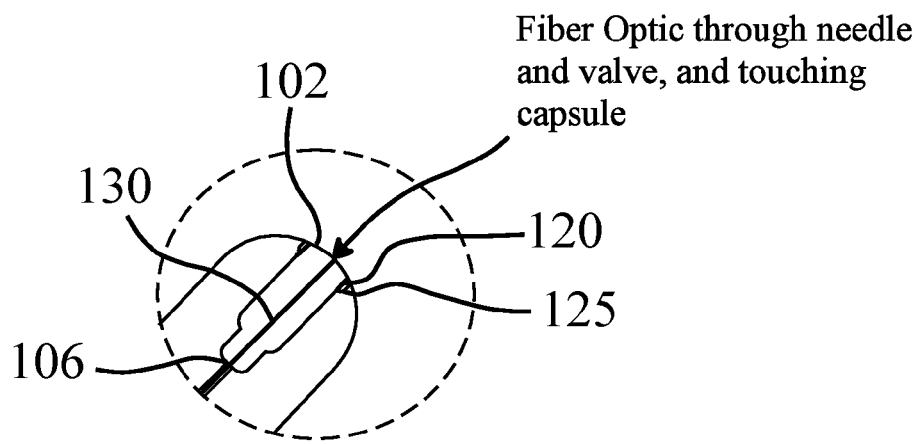
FIG. 2 illustrates a sectional view of a balloon capsule of an optical location system taken along the line labeled Detail A in FIG. 1.

FIG. 2 shows a sectional view of the balloon capsule 100 taken along the line labeled Detail A in FIG. 1. The balloon valve 120 includes a needle assembly and a needle sleeve 125 configured to provide a barrier so that the catheter needle does not pierce the balloon material. The needle assembly includes a needle 130, the distal end of which can contact the distal end 102 of the capsule 100. The optical fiber extends through the needle 130 to the distal end 102 of the capsule 100 in order to be exposed to light at the distal end of the capsule 100. The catheter 105 is configured to be detachable from the balloon capsule 100, for example, when the balloon capsule 100 is in position in the stomach. In some embodiments, the balloon valve may provide a mechanism for detachment of the catheter after inflation has been completed. In some embodiments, the catheter may be reusable.

Figure 3:
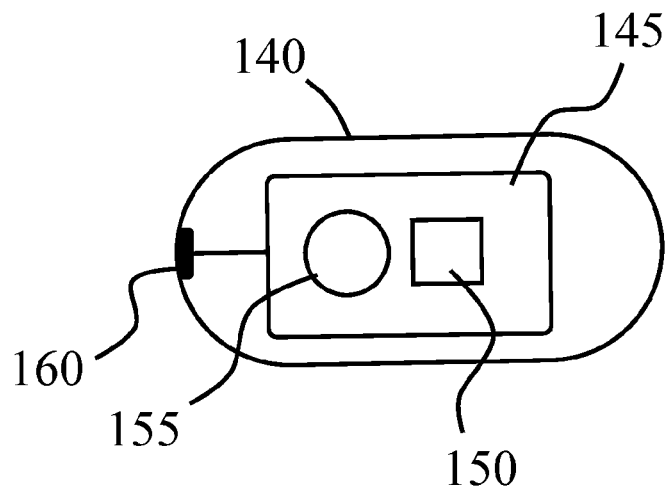
FIG. 3 illustrates an embodiment of a light-emitting capsule in accordance with an embodiment of an optical location system.

FIG. 3 shows a light-emitting capsule 140. Positioned within the interior of the light-emitting capsule 140 is a circuit board 145, a battery 150, and a light-emitting marker 155. The light-emitting capsule 140 further includes a power switch 160. The power switch 160 can be positioned on the exterior of the light-emitting capsule 140 or can at least partially extend out of the light-emitting capsule 140 so that the power switch 160 can contact stomach acid when the capsule 140 is positioned within the stomach. In some embodiments, the power switch 160 is activated based on contact with the stomach acid. The capsule 140 may also include a transmitter and/or receiver capable of capable of communicating to a location outside of the body. In some embodiments, the light-emitting capsule can be in electronic communication with the sensor interface unit of the light sensor 105 or one or more external devices. In some embodiments, the power switch 160 may be manually activated prior to insertion of the capsule 140 into the body. In other embodiments, the power switch 160 is activated based on receipt of a wireless signal.

In some embodiments, the capsule 140 can include a module capable of powering the capsule 140 electronics inductively. In some embodiments, the source of power to the capsule 140 can be external to the capsule 140. For example, the capsule 140 can derive power from an external electromagnetic radiofrequency (RF) source, as occurs with passive RF telemetry techniques, such as RF coupling, that are well known to those skilled in the art. The capsule 140 can be energized by a time-varying RF wave that is transmitted by an external transceiver.

Other possible sources of power for the capsule 140 include light, body heat, and the potential difference in voltage that can be generated in body fluids and detected by electrodes made of varying materials. The harnessing of such power sources for biotelemetry purposes is well described in R. Stuart Mackay: *Bio-Medical Telemetry, Sensing and Transmitting Biological Information from Ani-*

*mals and Man,* 2d ed., IEEE Press, New York, 1993, whose section entitled "Electronics: Power Sources" is hereby incorporated herein by reference in its entirety.

While the capsule 140 is in the shape of a capsule, it is contemplated that a light-emitting device can take a variety of different configurations, such as but not limited to: a cylinder configuration, a spherical configuration, a disc configuration, etc., where a particular configuration may be selected based on intended application, method of manufacture, etc. In some embodiments, the capsule 140 is sized and shaped to allow for normal passage through the body. After the light-emitting capsule is administered to a patient, the light-emitting capsule can be excreted in the patient's stool.

Figure 4:
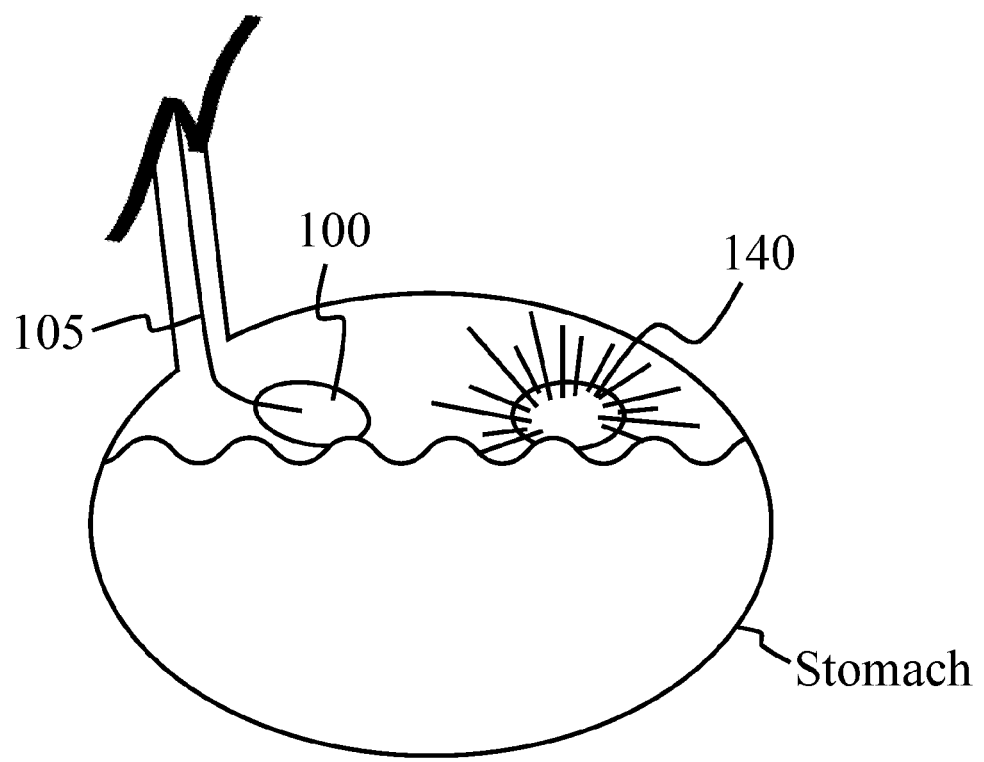
FIG. 4 illustrates a balloon capsule and light-emitting capsule positioned within a patient's stomach in accordance with an embodiment of an optical location system.

FIG. 4 shows the balloon capsule 100 and light-emitting capsule 140 positioned within a patient's stomach. The light-emitting capsule 140 is shown emitting light. As described above, the light can be received by the optical fiber in the balloon capsule 100 and transmitted to the light sensor 115. When a certain threshold measurement is exceeded at the light sensor 115, it can be determined that the balloon capsule 100 is positioned in the stomach. Accordingly, it can be determined that the balloon capsule 100 is in position for inflation of the intragastric balloon.

In some embodiments, the light-emitting capsule 140 can be transparent or semi-transparent or can include one or more transparent or semi-transparent sections to allow for light to radiate out of the light-emitting capsule 140. In some embodiments, one or more sections of the light-emitting capsule 140 may be transparent or semi-transparent and one or more sections of the light-emitting capsule may be non-transparent so that light can be emitted in one or more particular directions based on the orientation of the one or more transparent or semi-transparent sections. One or more sections of the light-emitting capsule 140 may include a clear polymer.

In some embodiments, the light-emitting marker 155 can be positioned within the capsule 140 so that light radiates out of the capsule 140 in all or substantially all directions. In some embodiments, the light-emitting marker 155 can be positioned to radiate light out of one or more particular sections of the capsule. For example, the light-emitting marker 155 can be positioned so that light radiates out of less than 25% of the capsule 140, less than 50% of the capsule 140, less than 75% of the capsule 140, between 25% and 50% of the capsule 140, between 50% and 75% of the capsule 140, or greater than 75% of the capsule 140. In some embodiments, the capsule 140 can be shaped or weighted so that light is emitted in one or more particular directions in the stomach. For example, the capsule 140 may have a weight in a lower section such that the lower section is positioned in contact with the fluids in the stomach when inserted therein. The light-emitting marker 155 can be positioned so as to radiate light out of an upper section of the capsule 140 in a direction away from the fluid.

In some embodiments the light-emitting marker 155 can be configured to emit light in the visible light range. The light-emitting marker 155 can also be configured to emit light in the ultraviolet range, near ultraviolet range, infrared range, or near infrared range.

The components of the optical location system can be made of many different materials or combinations of materials. For example, components of the optical location system can be made of Nitinol, shape memory plastics, shape memory gels, stainless steel, superalloys, titanium, silicone, elastomers, teflons, polyurethanes, polynorborenes, styrene butadiene co-polymers, cross-linked polyethylenes, cross-linked polyclooctenes, polyethers, polyacrylates, polyamides, polysiloxanes, polyether amides, polyether esters, and urethane-butadiene co-polymers, other polymers, or combinations of the above, or other suitable materials or materials as described elsewhere herein.

Some embodiments of an optical location system include a system control unit. The system control unit may be connected to the light sensor 115 wirelessly or through a wired connection for communication of signals therebetween. The system control unit may include a power cable and an auxiliary cable, for example a USB cable or Serial RS-232 cable, for example to connect to a computing device or other component. The system control unit may provide power to the sensor 115.

The system control unit may control the operation of the optical location system. In some embodiments, the system control unit provides an interface between components of the optical location system. The system control unit may provide power to the capsule 140 and/or control the output of the light-emitting marker 155. The system control unit may also collect sensor data (via the light sensor 115) and calculate intragastric volume-occupying device locations. The system control unit can then send the location data to a host computer. Therefore, the system control unit may also interface with the computer. The system control unit may also provide visual status indications.

In an alternative embodiment, one or more components of the capsule 140 may be included in a catheter. In some embodiments, the catheter may connect to the light sensor 115 or the system control unit.

In some embodiments, a distal end of a catheter in an optical location system, such as catheter 105, is sealed with an adhesive plug. Attached to the distal end of the catheter is a 31×12.41 mm pharmaceutical grade porcine gelatin capsule with a hydrophilic coating containing food-grade sugar. The catheter may include a 2 Fr catheter shaft formed from Pebax® (Polyether Block Amides) and Polyvinylpyrrolidone to provide a swallowable catheter with a hydrophilic coating to provide lubricity. The catheter may include one or more light detectors or optical fibers for tracking the catheter. The catheter may include an outer capsule formed from a USP-grade hard porcine gelatin capsule supplied by Torpac, Inc. (New Jersey, USA) containing food grade sugar to mimic food bolus weight for swallowing. The outer capsule may have a polyvinylpyrrolidone hydrophilic coating to provide lubricity. The catheter may include a distal strain relief formed from a thermoplastic polyurethane elastomer to provide strength to hold the gelatin capsule on the catheter shaft. The catheter may include an extension tube formed from a thermoplastic polyurethane elastomer to extend the length of the catheter for attachment to light sensor 115.

In some embodiments, the catheter may include a proximal luer hub. The luer hub may allow for attaching peripheral components or for grasping the catheter. The catheter may also include a catheter inner assembly that includes a catheter needle, a monofilament thread, and a needle holder. The catheter may also include a needle sleeve that surrounds and protects the needle assembly.

The catheter may also include a Y-port. The Y-port may be a splitter that connects various features of the catheter together. In some embodiments, the Y-port connects the luer hub and a strain relief tubing with a catheter bump tubing. The strain relief tubing may extend off-axis from the Y-port and connect with a connector. The connector may include a connector spacer. The catheter 105 may have robust mechanical properties. In some embodiments, the catheter 105 can bend 180° over a 0.5 cm radius mandrel without kinking at the center portion of a Peebax catheter shaft.

In some embodiments the balloon capsule 100 and/or capsule 140 can incorporate an additional tracking or visualization component or components that enable physicians to determine the location and/or orientation and/or state of the device within the patient's body using electromagnetic, magnetic, voltaic, pH, and/or acoustic (e.g., ultrasonic) methods In some embodiments, the balloon capsule 100 and/or catheter 105 can include a plurality of optical fibers and/or other light receiving or detecting components positioned at various locations on the interior or exterior of the balloon capsule 100 and/or catheter 105. The light sensor 115 can be configured to detect light energy received at the distal end of each of the optical fibers and the other light receiving or detecting components. Accordingly, the light sensor 115 can detect light energy at a plurality of locations on the interior or exterior of the balloon capsule 100 and/or catheter 105, and an amount of light energy or change in amount of light energy received can be determined at each location on the balloon capsule 100 and/or catheter 105. A comparison of the amount of light energy received or a change in amount of light energy received at multiple locations on the balloon capsule 100 and/or catheter 105 can be used to determine a location and/or orientation and/or state of the balloon capsule 100 and/or catheter 105.

In alternative embodiments of an optical location system, one or more light-emitting markers are positioned within the interior of a catheter, such as catheter 105, connected to a balloon capsule, such as balloon capsule 100, and one or more optical fibers or other light detecting components are positioned within a separate swallowable catheter or device. In a similar manner to the optical location system described with respect to FIGS. 1-4, a determination can be made that the balloon capsule 100 is positioned within the stomach when a light energy threshold measurement is exceeded. For example, the separate swallowable catheter or device can be administered so that it is positioned within the stomach. After the separate swallowable catheter or device is positioned within the stomach, the balloon capsule can advanced into the stomach. As the balloon capsule is advanced, into the stomach, light radiating from the light-emitting marker within the balloon capsule or catheter in connection with the balloon capsule can be received by the optical fibers or other light detecting components within the separate swallowable catheter or device.

Figure 5:
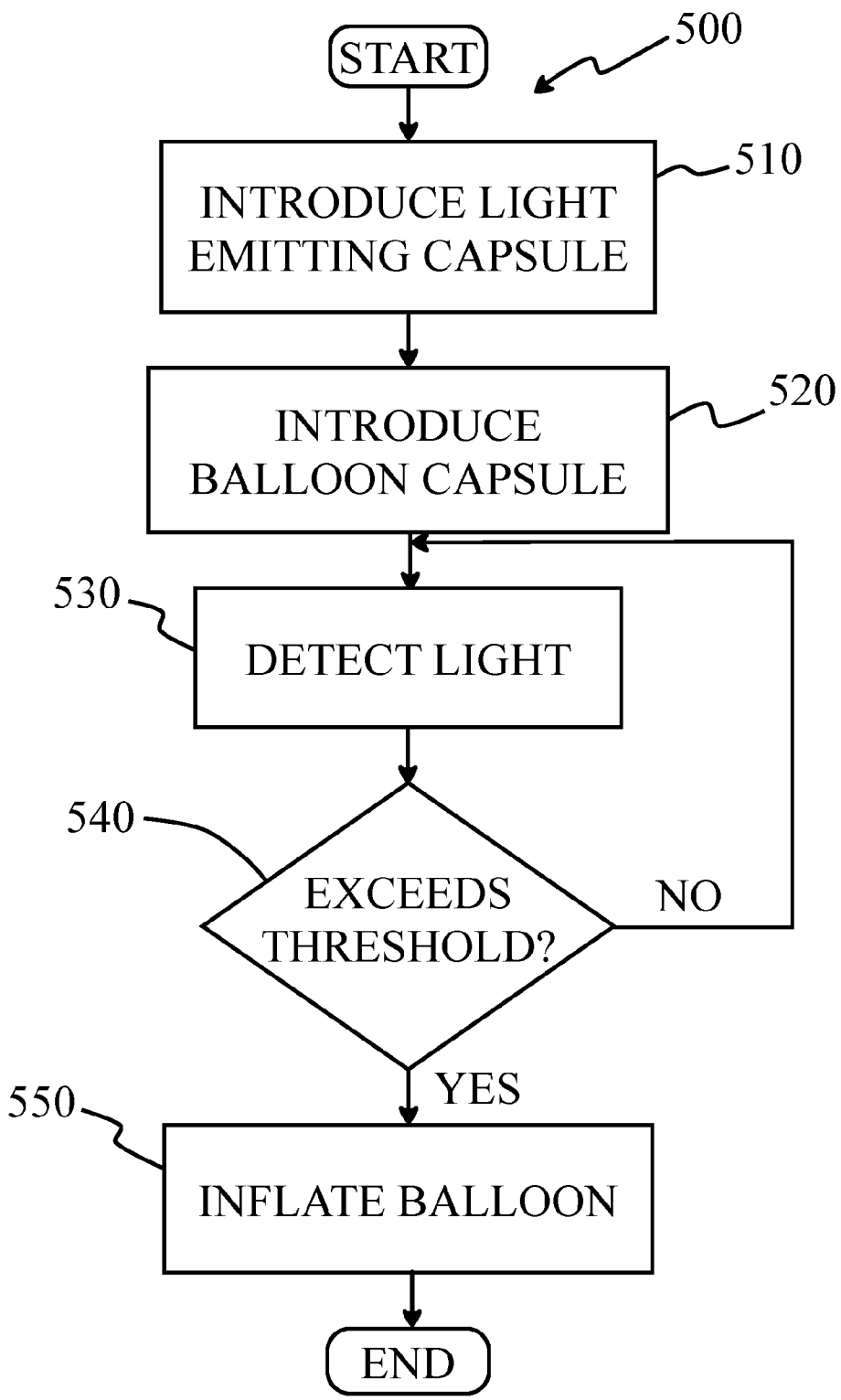
FIG. 5 illustrates a flowchart of an embodiment of a method for using an optical sensor with an intragastric device to determine the location of the intragastric device.

FIG. 5 depicts a flowchart showing a process 500 for using an optical sensor with an intragastric device to determine the location of the intragastric device in accordance with an illustrative embodiment of the present invention. The process begins with a step 510, wherein a light-emitting marker is introduced into the body, such as light-emitting marker 155 as depicted in FIG. 3. In some embodiments, the light-emitting marker may be introduced orally. In some embodiments, the light-emitting marker is positioned within a swallowable device or catheter that is administered orally. In some embodiments, an insertion device may be used to introduce the light-emitting marker or swallowable device or catheter.

After the light-emitting marker is introduced into the body, the process 500 moves to a step 520, wherein a balloon capsule coupled to a light sensor is introduced into the body, such as balloon capsule 100 and light sensor 115 as depicted in FIGS. 1, 2, and 4. In some embodiments, the balloon capsule is coupled to the light detector through one or more optical fibers positioned within a catheter connected to the balloon capsule, such as catheter 105. In some embodiments, one or more optical fibers or light detector components are positioned on the interior or exterior of the balloon capsule and/or a catheter connected to the balloon capsule.

After the balloon capsule is introduced into the body, the process 500 moves to a step 530, wherein light is detected by the light sensor. In some embodiments a quantity of light received at the light sensor is detected. In some embodiments, a change in the quantity of light received at the light sensor is detected. The light may be received through one or more optical fibers such as the optical fiber described above with reference to FIGS. 1, 2, and 4. In light sensor is configured to detect light emitted by the light-emitting marker. In some embodiments, the process 500 includes an additional step of activating the light-emitting marker. In some embodiments, the light-emitting marker is activated prior to introduction into the body. In other embodiments, the light-emitting marker can be activated in response to one or more conditions in the body, such as in response to contact with stomach fluid. The light-emitting marker may also be activated in response to receipt of a wireless signal.

After light is detected, the process 500 moves to a decision step 540, wherein a decision is made whether the light detected by the light sensor exceeds a predefined threshold value. The predefined threshold value may be indicative of an amount of light that would be received by the optical sensor if the balloon capsule and the light-emitting marker are both positioned within a stomach of a patient. If the light detected by the light sensor does not exceed a predefined threshold value, the process 500 returns to step 530. If the light detected by the light sensor exceeds the predefined threshold value, the process 500 moves to step 550, wherein the gastric balloon is inflated. The gastric balloon can be inflated using any of the techniques described throughout. The process 500 then concludes at an end step. In some embodiments, the light sensor may be decoupled from the balloon capsule following inflation of the gastric balloon. In some embodiments, the catheter connected to the balloon capsule can be detached from the balloon capsule following inflation of the gastric balloon. In some embodiments, the light-emitting marker may be passed through the body.

Compared to methods of medical imaging, an optical location system provides several advantages. The components of the optical location system may be more portable than some medical imaging equipment and can be brought to a patient's bedside. The optical location system is substantially lower in cost, and it also does not use harmful ionizing radiation.

Film Permeability

A variety of different composite films were tested for permeability of gases as measured by $CO_2$ diffusion at 37° C., and for suitability for use as materials for wall or other components of the intragastric devices of various embodiments. As shown in the data of Table 3, the permeability of varying composite wall constructions were evaluated and determined by their resistance to $CO_2$ diffusion rates, where the smaller the permeability test result, the higher barrier to gas diffusion the film provides. As noted, the permeability of the film and degree of barrier the film provides to gas diffusion was derived using $CO_2$ at 37° C., one of the most permeable gasses. This can be used as a surrogate to other gas diffusion rates where generally $CO_2$ is 3 to 5 times faster in diffusion across a membrane than oxygen, and nitrogen is 0.2 to 0.4 times faster than the oxygen transmission rate when these are evaluated at 25° C. As Table 3 indicates, permeability of the film is also affected by orientation of the film (which layer is exposed to the $CO_2$ gas first), and Relative Humidity. The walls were tested under conditions of low relative humidity (0%, representative of conditions inside the balloon upon fill) and high relative humidity (100%, representative of in vivo conditions). In certain embodiments, a composite wall having a permeability of <10 cc/m²/day is generally preferred; however, depending upon the desired effect of inflation and re-inflation by in vivo gasses such as $CO_2$, a higher permeability of >10 cc/m²/day in in vivo conditions can be desirable. For example, each of the films in the table can be suitable for use in various selected embodiments, such that the resulting balloon wall has a permeability to $CO_2$ of even greater than >10 cc/m²/day, e.g., >50 cc/m²/day, >100 cc/m²/day, >200 cc/m²/day, >300 cc/m²/day, >400 cc/m²/day, >500 cc/m²/day, >750 cc/m²/day, >1000 cc/m²/day, >1500 cc/m²/day, >2000 cc/m²/day, >2500 cc/m²/day, >3000 cc/m²/day, >3500 cc/m²/day, or even >4000 cc/m²/day. In selected embodiments, it is generally preferred to have a permeability of from about 1, 2, 3, 4, 5, 6, 7, 8, 9, or 10 cc/m²/day to about 15, 20, 25, 30, 35, 40, 45, 50, 60, 70, 80, 90, 100, 110, 120, 130, 140 or 150 cc/m²/day. In Table 3 and elsewhere herein, various films are listed. When the film comprises two or more layers, a "/" is used to indicate a layer of one material adjacent to another layer, optionally with intervening layers or materials. For example, "AB/C" would refer to a film comprising a layer of A adjacent to a layer of B, and the layer of B adjacent to a layer of C on an opposite side of layer B from the side adjacent to layer A, with or without intervening layers or materials (e.g., tie layers, adhesives, surface preparations, surface treatments, or the like). Referring to the first entry of Table 3, "PE/EVOH/PE" refers to a film comprising a first layer of polyethylene adjacent to a layer of ethylene vinyl alcohol, and the layer of ethylene vinyl alcohol adjacent to a second layer of polyethylene on an opposite side of the ethylene vinyl alcohol to that adjacent to the first layer of polyethylene.

TABLE 3

| Film | Film Thickness (in) | Innermost Layer ($CO_2$ Exposed Layer) | RH % | Permeability Test Results (cc/m2/day) (1 ATM/37° C.) |
| --- | --- | --- | --- | --- |
| PE/EVOH/PE | 0.002 ± 0.001 | PE | 0 | 10.8 |
| 70% Nylon 6,66, 30% MXD6/ EVOH/PVDC/ 70% Nylon 6,66, 30% MXD6/ LLDPE + LDPE | 0.003 | Nylon 6,66 | 0 | 2.4 |
| 70% Nylon 6,66, 30% MXD6/ EVOH/PVDC/ 70% Nylon 6,66, 30% MXD6/ LLDPE + LDPE | 0.003 | Nylon 6,66 | 95 ± 5 | 51.0 |
| 70% Nylon 6,66, 30% MXD6/ EVOH/PVDC/ 70% Nylon 6,66, 30% MXD6/ LLDPE + LDPE | 0.003 | LDPE | 95 ± 5 | 3.3 |
| 70% Nylon 6,66, 30% MXD6/PVDC/ 70% Nylon 6,66, 30% MXD6/ LLDPE + LDPE | 0.002 | LDPE | 0 | 43.0 |
| 70% Nylon 6,66, 30% MXD6/PVDC/ 70% Nylon 6,66, 30% MXD6/ LLDPE + LDPE | 0.003 | LDPE | 0 | 50.0 |
| 70% Nylon 6,66, 30% MXD6/PVDC/ 70% Nylon 6,66, 30% MXD6/ LLDPE + LDPE | 0.002 | LDPE | 95 ± 5 | 41.0 |
| 70% Nylon 6,66, 30% MXD6/PVDC/70% Nylon 6,66, 30% MXD6/LLDPE + LDPE | 0.003 | LDPE | 95 ± 5 | 49.0 |
| Bi-axially Oriented PP/EVOH/PE | 0.00125 | LDPE | 0 | 15.4 |
| Bi-axially Oriented PP/EVOH/PE | 0.00175 | PE | 0 | 8.2 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| Bi-axially Oriented PP/EVOH/PE | 0.00125 | PE | 95 ± 5 | 282.6 |
| Bi-axially Oriented PP/EVOH/PE | 0.00125 | PE | 95 ± 5 | 1088.0 |
| Bi-axially Oriented PP/EVOH/PE | 0.00175 | PE | 95 ± 5 | 235.4 |
| Cast PP | 0.002 ± 0.001 | NA | 0 | 772.0 |
| Cast PP/PE/EVOH/PE | 0.0025 | PE | 0 | 7.2 |
| Cast PP/PE/EVOH/PE | 0.0025 | PE | 0 | 10.1 |
| Cast PP/PE/EVOH/PE | 0.0025 | PE | 95 ± 5 | 169.3 |
| Cast PP/PE/EVOH/PE | 0.0025 | PE | 95 ± 5 | 18.5 |
| Coextruded PE/EVOH/PE | 0.00125 | PE | 0 | 8.1 |
| Coextruded PE/EVOH/PE | 0.0015 | PE | 0 | 4.9 |
| Coextruded PET/SiOx/PE | 0.002 ± 0.001 | PE | 0 | 12.4 |
| CoExtrude-LLDPE/HDPE/EVOH/HDPE | 0.0025 | HDPE | 0 | 1.7 |
| HDPE/HDPE/PVdC/EVOH/HDPE/LLDPE + LDPE | 0.003 | HDPE | 0 | 5.0 |
| HDPE/HDPE/PVdC/EVOH/HDPE/LLDPE + LDPE | 0.003 | HDPE | 95 ± 5 | 6.8 |
| HDPE/HDPE/PVdC/EVOH/HDPE/LLDPE + LDPE | 0.003 | LDPE | 0 | 4.4 |
| HDPE/HDPE/PVdC/EVOH/HDPE/LLDPE + LDPE | 0.003 | LDPE | 95 ± 5 | 52.0 |
| HDPE/HDPE/PVdC/HDPE/HDPE/LLDPE + LDPE | 0.003 | LDPE | 0 | 74.0 |
| HDPE/HDPE/PVdC/HDPE/HDPE/LLDPE + LDPE | 0.003 | LDPE | 0 | 47.0 |
| HDPE/HDPE/PVdC/HDPE/HDPE/LLDPE + LDPE | 0.003 | LDPE | 95 ± 5 | 68.0 |
| HDPE/HDPE/PVdC/HDPE/HDPE/LLDPE + LDPE | 0.003 | LDPE | 95 ± 5 | 44.0 |
| Kurarister ™ C, 3 mil | 0.003 | UNK | 0 | 3.2 |
| Nylon12/PvDC/Nylon 12/LLDPE + LDPE | 0.003 | LLDPE + LDPE | 0 | 52.0 |
| Nylon12/PvDC/Nylon 12/LLDPE + LDPE | 0.003 | LLDPE + LDPE | 95 ± 5 | 56.0 |
| MPI Supernyl LLDPE 40 μm | 0.0022 | LLDPE | 0 | 3.3 |
| MPI Supernyl LLDPE 40 μm | 0.0022 | LLDPE | 95 ± 5 | 5.8 |
| MPI Supernyl LLDPE 50 μm | 0.0026 | LLDPE | 0 | 4.2 |
| MPI Supernyl LLDPE 50 μm | 0.0026 | LLDPE | 95 ± 5 | 7.5 |
| Nylon12/PvDC/Nylon 12/LLDPE + LDPE | 0.003 | LLDPE + LDPE | 0 | 59.3 |
| Nylon12/PVDC/Nylon12/LLDPE + LDPE | 0.003 | LLDPE + LDPE | 95 ± 5 | 29.5 |
| Nylon12/PVDC/Nylon12/LLDPE + LDPE-Thermoformed | 0.003 | LLDPE + LDPE | 0 | 73.2 |
| Nylon12/PVDC/Nylon12/LLDPE + LDPE | 0.0024 | LLDPE + LDPE | 0 | 77.0 |
| Nylon12/PVDC/Nylon12/ | 0.0024 | LLDPE + LDPE | 95 ± 5 | 68.0 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| Nylon12/PVdC/ Nylon12/LDPE-Cast | 0.003 | LDPE | 0 | 58.0 |
| Nylon12/Nylon Tie/ EVA/PVdC/Adhesive/ Nylon12/Nylon Tie/ LDPE-Cast | 0.003 | LDPE | 95 ± 5 | 54.0 |
| Nylon12/PVdC/ Nylon12/LDPE | 0.0035 | LDPE | 0 | 14.9 |
| Nylon12/ PVdC/Nylon12/ LDPE | 0.004 | LDPE | 0 | 34.0 |
| Nylon12/ PVdC/Nylon12/ LDPE | 0.0035 | LDPE | 95 ± 5 | 24.9 |
| Nylon12/ PVdC/Nylon12/ LDPE | 0.0035 | LDPE | 95 ± 5 | 41.3 |
| Nylon12/ PVdC/Nylon12/ LDPE | 0.004 | LDPE | 95 ± 5 | 31.7 |
| Nylon 6,66/ PVDC/Nylon6,66/ LLDPE + LDPE | 0.0024 | LDPE | 0 | 54.0 |
| Nylon 6,66/ PVDC/Nylon6,66/ LLDPE + LDPE | 0.0024 | LDPE | 95 ± 5 | 56.0 |
| Nylon 6,66/ EVOH/PVDC/ Nylon 6,66/LDPE | 0.0032 | LDPE | 0 | 5.5 |
| Nylon 6,66/ EVOH/PVDC/ Nylon 6,66/LDPE | 0.0032 | LDPE | 95 ± 5 | 6.4 |
| Nylon 6,66/ EVOH/PVDC/ Nylon 6,66/LDPE | 0.0032 | Nylon 6, 66 | 95 ± 5 | 49.9 |
| Nylon 6,66/ PVDC/Nylon6,66/ LLDPE + LDPE | 0.0027 | LDPE | 0 | 57.0 |
| Nylon 6,66/ PVDC/Nylon6,66/ LLDPE + LDPE | 0.003 | LDPE | 0 | 41.0 |
| Nylon 6,66/ PVDC/Nylon6,66/ LLDPE + LDPE | 0.0027 | LDPE | 95 ± 5 | 55.0 |
| Nylon 6,66/ PVDC/Nylon6,66/ LLDPE + LDPE | 0.003 | LDPE | 95 ± 5 | 46.0 |
| Multi-layer Nylon 12/ LLDPE + LDPE | 0.0035 | LDPE | 0 | 3203.5 |
| Multi-layer Nylon 12/ LLDPE + LDPE | 0.004 | LDPE | 0 | 2725.5 |
| Multi-layer Nylon 12/ LLDPE + LDPE | 0.0045 | LDPE | 0 | 2553.6 |
| Multi-layer Nylon 12/ LLDPE + LDPE | 0.0035 | LDPE | 95 ± 5 | 2539.3 |
| Multi-layer Nylon 12/ LLDPE + LDPE | 0.004 | LDPE | 95 ± 5 | 2527.8 |
| Multi-layer Nylon 12/ LLDPE + LDPE + Parylene | 0.0045 | LDPE | 0 | 1522.6 |
| Multi-layer Nylon 12/ LLDPE + LDPE + Parylene | 0.0045 | LDPE | 95 ± 5 | 1275.5 |
| NYLON-SIOX/HDPE/LLDPE | 0.003 | LLDPE | 95 ± 5 | 83.0 |
| NYLON-SIOX/HDPE/LLDPE | 0.003 | LLDPE | 0 | 70.0 |
| Nylon-SIOX/LLDPE | 0.0015 | LLDPE | 0 | 134.0 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| Nylon-SIOX/LLDPE | 0.0015 | LLDPE | 95 ± 5 | 82.0 |
| OPP Co-extrude with mPE/EVOH/mPE | 0.002 | mPE | 0 | 5.9 |
| OPP Laminated to mPE/EVOH/mPE | 0.0025 | mPE | 0 | 4.7 |
| OPP Laminated to mPE/EVOH/mPE | 0.003 | mPE | 0 | 3.4 |
| OPP Laminated to mPE/EVOH/mPE | 0.0025 | mPE | 95 ± 5 | 294.3 |
| OPP SIOX/LLDPE | 0.002 | LLDPE | 0 | 540.5 |
| OPP SIOX/LLDPE | 0.002 | LLDPE | 0 | 1081.0 |
| OPP SIOX/LLDPE | 0.002 | LLDPE | 95 ± 5 | 565.0 |
| OPP SIOX/LLDPE | 0.002 | LLDPE | 95 ± 5 | 594.5 |
| OPP/mPE/EVOH/mPE | 0.0021 | mPE | 0 | 5.0 |
| OPP/mPE/EVOH/mPE | 0.0021 | mPE | 95 ± 5 | 437.1 |
| OPP/PE/EVOH/PE | 0.0025 | OPP | 0 | 8.5 |
| OPP/PE/EVOH/PE | 0.0025 | OPP | 95 ± 5 | 11.6 |
| OPP/PE/EVOH/PE | 0.00175 | PE | 0 | 8.1 |
| OPP/PE/EVOH/PE | 0.0025 | PE | 0 | 8.9 |
| OPP/PE/EVOH/PE | 0.0025 | PE | 0 | 18.6 |
| OPP/PE/EVOH/PE | 0.0025 | PE | 95 ± 5 | 259.0 |
| OPP/PE/EVOH/PE | 0.0025 | PE | 95 ± 5 | 556.1 |
| OPP/PVDC/mPE | 0.0017 | mPE | 0 | 74.2 |
| OPP/PVDC/mPE | 0.0017 | mPE | 95 ± 5 | 84.6 |
| OPP-SIOX/LLDPE | 0.002 ± 0.001 | LLDPE | 95 ± 5 | 1159.7 |
| Oriented PA | 0.002 ± 0.001 | NA | 0 | 750.9 |
| Oriented PP | 0.002 ± 0.001 | NA | 0 | 726.0 |
| PA/EVOH/PA/LLDPE | 0.0022 | LLDPE | 0 | 5.0 |
| PA/EVOH/PA/LLDPE | 0.0022 | LLDPE | 0 | 3.1 |
| PA/EVOH/PA/LLDPE | 0.0022 | LLDPE | 95 ± 5 | 10.8 |
| PE/EVOH/PE | 0.002 ± 0.001 | PE | 0 | 9.2 |
| PET | 0.001 | PE | 0 | 524.7 |
| SiOx-PET/EVOH/PE | 0.002 | PE | 0 | 1.4 |
| SiOx-PET/MPE/EVOH/mPE | 0.0016 | mPE | 0 | 1.0 |
| Si-Ox-PET/PE/EVOH/PE | 0.00125 | PE | 0 | 1.7 |
| Si-Ox-PET/PE/EVOH/PE | 0.0015 | PE | 0 | 1.6 |
| Si-Ox-PET/PE/EVOH/PE | 0.0015 | PE | 0 | 5.4 |
| Si-Ox-PET/PE/EVOH/PE | 0.002 | PE | 0 | 1.5 |
| Si-Ox-PET/PE/EVOH/PE | 0.002 | PE | 0 | 1.8 |
| Si-Ox-PET/PE/EVOH/PE | 0.002 | PE | 95 ± 5 | 22.6 |

Animal Studies

Two different composite walls were tested: a material (Nylon12/PvDC/Nylon 12/LLDPE+LDPE) with high barrier material characteristics and a material with low barrier characteristics (multi-layer Nylon12/LLDPE+LDPE). A series of experiments were performed using a mixture of 75% $N_2$ and 25% $CO_2$ as the balloon initial fill. As shown in the data of Table 4, each of the balloons maintained pressure over the duration tested, but gained substantially in volume. Considering the composite walls studied are not a metal canister (volume and pressure change due to material stretch) there was a significant change in the number of overall gas molecules inside the balloon from the initial gas fill. Since the internal balloon environment started with $CO_2$ and nitrogen, most likely additional $CO_2$ entered due to the environment the balloon was subjected to ($N_2$ and $CO_2$ headspace) but also most likely other gases available in the air as well as water vapor also diffused within the balloon wall.

TABLE 4

| Pig # | Balloon #, Wall Composition | Starting implant pressure (PSI) | Estd. Volume at implant | Explant Volume (cc) | Explant Pressure (PSI) | % $CO_2$ in balloon (meas. w/ $CO_2$ meter) | Measured % $CO_2$ in stomach gas (%) | Final Vol. | % gas gain (calc.) |
|---|---|---|---|---|---|---|---|---|---|
| 1 | 1, Barrier Material (Nylon/Saran) | 1.0 | 277 | 360 | 1.1 | 22% | 10% | 385 | 23.5 |
| 1 | 2, Barrier Material (Nylon/Saran) | 1.09 | 282 | 340 | 0.7 | 19.63% | 10% | 358 | 15 |
| 2 | 3, Non-Barrier Material (Nylon) | 1.15 | 283 | 330 | 1.2 | 26.57% | 8% | 320 | 14.5 |
| 2 | 4, Non-Barrier Material (Nylon) | 1.07 | 281 | 323 | 0.96 | 31% | 8% | 316 | 12.4 |

Volume gains were higher for the barrier material composite walls than for the non-barrier walls. An analysis of gas in the balloons after explants (Tables 5a and 5b) showed gains in oxygen, hydrogen, and argon in addition to the nitrogen and carbon dioxide that was already present in the balloon at initial inflation. The balloons, both with a good barrier composite wall (table 5a) and a poor barrier composite wall (table 5b) both gained in overall volume while maintaining pressure after 30 days in vivo. Explant results of the balloon with a composite wall containing a good barrier material (#2, table 5a) showed a slightly higher increase in carbon dioxide than the wall without a barrier material (#3, table 5b). It is unlikely that nitrogen diffused in or out of the balloon due to its inertness as well as the external gastric environment most likely matched the internal concentration of nitrogen such that there was no (or an insignificant) diffusion gradient for the nitrogen gas.

TABLE 5a

| Gas | % v/v, by MS | Detection Limit |
|---|---|---|
| Nitrogen | 64.04 | 0.01 |
| Oxygen | 7.63 | 0.01 |
| Argon | 0.60 | 0.01 |
| Carbon Dioxide | 19.63 | 0.01 |
| Hydrogen | 8.10 | 0.01 |
| Helium | not detected | 0.01 |
| Methane | not detected | 0.01 |

TABLE 5b

| Gas | % v/v, by MS | Detection Limit |
|---|---|---|
| Nitrogen | 62.33 | 0.01 |
| Oxygen | 9.27 | 0.01 |
| Argon | 0.7 | 0.01 |
| Carbon Dioxide | 26.57 | 0.01 |
| Hydrogen | 1.13 | 0.01 |
| Helium | not detected | 0.01 |
| Methane | not detected | 0.01 |

The data show that when it is desirable to minimize volume gain over the useful life of the device, a non-barrier composite wall material may be more desirable than a barrier wall. This observation is contrary to conventional wisdom that seeks to maintain the initial fill of gas in the balloon by maximizing barrier properties of the intragastric balloon wall.

Simulated Gastric Environment

Balloons constructed with non-barrier film composite walls were tested (multi-layer Nylon 12/LLDPE+LDPE) in a simulated gastric environment (tank containing a 1.2 pH HCl solution with NaCl and pepsin at 40° C. with a variable $N_2/CO_2$ headspace; samples were taken at peak $CO_2$ at 50% and trough $CO_2$ at 0% in the tank). The balloons were initially filled with either pure $N_2$ or a mixture of $N_2$ (75%) and $CO_2$ (25%), and pressure, volume, and gas gain were monitored over time. The balloon filled with pure nitrogen exhibited significantly higher gain of $CO_2$ when compared to the balloon filled with the $N_2/CO_2$ mixture. When a volume gain (as manifested in a gain of $CO_2$ gas) is desired, pure nitrogen as the initial fill gas in connection with a non-barrier film is desirable. Data for the experiments is provided in Table 6.

TABLE 6

| Expt. | Material | Sample | Balloon Internal Gas | Pressure (Day 0) | Volume (Day 0) | Volume (Day 1) | Volume (Day 2) | Pressure (Day 2) |
|---|---|---|---|---|---|---|---|---|
| End of Cycle → | | | | | | | 50% $CO_2$ | 50% $CO_2$ |
| # | OGB # | # | N2 or N2/CO2 | T = 0 (psi) | T = 0 (cc) | T = 1 (cc) | T = 2 (cc) | T = 2 (psi) |
| 1 | Non-Barrier Film | 1 | N2 | 1.12 | 304 | 312 | 314 | 1.84 |
| | | 3 | | 1.12 | 300 | 310 | 313 | 1.81 |
| | | 4 | | 1.09 | 294 | 309 | 311 | 1.79 |
| | | 5 | | 1.10 | 300 | 312 | 314 | 1.82 |
| | | 6 | | 1.10 | 309 | 317 | 320 | 1.68 |

TABLE 6-continued

| | | | | | | | | |
|---|---|---|---|---|---|---|---|---|
| | | avg. | | 1.11 | 301 | 312 | 314 | 1.79 |
| 2 | | 1B | N2/CO2 | 1.10 | 318 | 328 | 326 | 1.15 |
| | | 2B | (75%/25%) | 1.00 | 295 | 301 | 299 | 1.04 |
| | | 4B | | 1.10 | 292 | 300 | 295 | 1.18 |
| | | 5B | | 1.08 | 294 | 306 | 303 | 1.22 |
| | | 6B | | 1.07 | 293 | 300 | 293 | 1.18 |
| | | avg. | | 1.07 | 298 | 307 | 303 | 1.15 |

| Expt. # | Material | Sample # | Balloon Internal Gas | (Day 2) 9:00 AM | Volume (Day 5) 9:00am | Volume (Day 5) 7.00 PM | Pressure (Day 5) 7:00 PM | (Day 5) 7.00 PM |
|---|---|---|---|---|---|---|---|---|
| | | | End of Cycle → | % Gas Gain | 50% CO$_2$ | 0% CO$_2$ | 0% CO$_2$ | % Gas Gain |
| | OGB # | | N2 or N2/CO2 | T = 2 (%) | T = 5 (cc) | T = 5 (cc) | T = 5 (psi) | T = 5 (%) |
| 1 | Non-Barrier Film | 1 | N2 | 7.4% | 323 | 319 | 2.50 | 12.3% |
| | | 3 | | 8.2% | 319 | 314 | 2.53 | 12.3% |
| | | 4 | | 9.5% | 321 | 313 | 2.56 | 14.1% |
| | | 5 | | 8.6% | 324 | 318 | 2.70 | 14.3% |
| | | 6 | | 6.9% | 329 | 328 | 2.58 | 13.9% |
| | | avg. | | 8.1% | 323 | 318 | 2.57 | 13.4% |
| 2 | | 1B | N2/CO2 (75%/25%) | 2.1% | 329 | 324 | 1.37 | 2.6% |
| | | 2B | | 1.2% | 302 | 297 | 1.28 | 1.8% |
| | | 4B | | 1.1% | 299 | 293 | 1.25 | 1.0% |
| | | 5B | | 2.9% | 305 | 302 | 1.16 | 2.4% |
| | | 6B | | 0.5% | 298 | 295 | 1.26 | 1.4% |
| | | avg. | | 1.6% | 307 | 302 | 1.26 | 1.8% |

| Expt. # | Matetial | Sample # | Balloon Internal Gas | Volume (Day 6) 8:00 AM | Pressure (Day 6) 8:00 AM | (Day 6) 8:00 AM | Volume (Day 6) 7:00 PM | Pressure (Day 6) 7:00 PM |
|---|---|---|---|---|---|---|---|---|
| | | | End of Cycle → | 50% CO$_2$ | 50% CO$_2$ | % Gas Gain | 0% CO$_2$ | 0% CO$_2$ |
| | | | | T = 6 (cc) | T = 6 (psi) | T = 6 (%) | T = 6 (cc) | T = 6 (psi) |
| | | | | | | | balloon cut during test | |
| 1 | Non-Barrier Film | 1 | N$_2$ | 323 | 3.03 | 16.0% | | |
| | | 3 | | 320 | 3.01 | 16.3% | 318 | 2.84 |
| | | 4 | | 322 | 3.04 | 18.7% | 321 | 2.87 |
| | | 5 | | 322 | 3.19 | 17.7% | 322 | 2.98 |
| | | 6 | | 330 | 3.12 | 17.0% | 329 | 2.89 |
| | | avg. | | 323 | 3.08 | 17.1% | 323 | 2.90 |
| 2 | | 1B | N$_2$/CO$_2$ (75%/25%) | 329 | 1.82 | 5.7% | 329 | 1.48 |
| | | 2B | | 300 | 1.61 | 4.0% | 301 | 1.38 |
| | | 4B | | 299 | 1.64 | 4.2% | 298 | 1.46 |
| | | 5B | | 304 | 1.55 | 4.6% | 306 | 1.33 |
| | | 6B | | 299 | 1.62 | 4.0% | 298 | 1.41 |
| | | avg. | | 306 | 1.65 | 4.5% | 306 | 1.41 |

| Expt. # | Material | Sample # | Balloon Internal Gas | (Day 6) 7:00 PM | Volume (Day 7) 8:00 AM | Pressure (Day 7) 8:00 AM | CO$_2$ % (Day 7) 8:00AM | Volume (Day 7) 7:00 PM |
|---|---|---|---|---|---|---|---|---|
| | | | End of Cycle → | % Gas Gain | 50% CO$_2$ | 50% CO$_2$ | % Gas Gain* | 0% CO$_2$ |
| | | | | T = 6 (%) | T = 7 (cc) | T = 7 (psi) | T = 7 (%) | T = 7 (cc) |
| | | | | balloon cut during test | | | | |
| 1 | Non-Barrier Film | 1 | N$_2$ | | | | | |
| | | 3 | | 14.9% | 322 | 3.02 | 16.8% | 319 |
| | | 4 | | 17.7% | 322 | 3.05 | 18.8% | 320 |
| | | 5 | | 16.7% | 325 | 3.15 | 18.3% | 323 |
| | | 6 | | 15.6% | 331 | 3.08 | 17.0% | 329 |
| | | avg. | | 16.2% | 325 | 3.08 | 17.7% | 323 |
| 2 | | 1B | N$_2$/CO$_2$ (75%/25%) | 4.2% | 327 | 1.63 | 4.4% | 326 |
| | | 2B | | 3.2% | 300 | 1.57 | 3.8% | 299 |
| | | 4B | | 3.1% | 299 | 1.61 | 4.0% | 296 |
| | | 5B | | 4.1% | 303 | 1.45 | 3.9% | 303 |
| | | 6B | | 2.8% | 300 | 1.60 | 4.1% | 297 |
| | | avg. | | 3.5% | 306 | 1.57 | 4.1% | 304 |

TABLE 6-continued

| Expt. # | Material | Sample # | Balloon Internal Gas | Pressure (Day 7) 7:00 PM | CO$_2$ % (Day 7) 7:00 PM | Volume (Day 8) 8:00 AM | Pressure (Day 8) 8:00 AM | CO$_2$ % (Day 8) 8:00 AM |
|---|---|---|---|---|---|---|---|---|
| | | | End of Cycle → | | | | 50% CO$_2$ | % Gas Gain |
| | | | | T = 7 | T = 7 (%) | T = 8 (cc) | T = 8 (psi) | T = 8 (%) |
| | | | | | balloon cut during test | | | |
| 1 | Non-Barrier Film | 1 | N$_2$ | | | | | |
| | | 3 | | 2.90 | 15.5% | 322 | 3.01 | 16.8% |
| | | 4 | | 2.92 | 17.7% | 323 | 2.99 | 18.8% |
| | | 5 | | 2.91 | 16.7% | 325 | 3.07 | 17.9% |
| | | 6 | | 2.88 | 15.6% | 332 | 3.03 | 17.1% |
| | | avg. | | 2.90 | 16.3% | 326 | 3.03 | 17.6% |
| 2 | | 1B | N$_2$/CO$_2$ | 1.42 | 3.3% | 329 | 1.43 | 4.0% |
| | | 2B | (75%/25%) | 1.37 | 2.7% | 301 | 1.42 | 3.4% |
| | | 4B | | 1.37 | 2.3% | 299 | 1.29 | 2.6% |
| | | 5B | | 1.23 | 2.9% | 306 | 1.32 | 4.0% |
| | | 6B | | 1.42 | 2.6% | 299 | 1.43 | 3.1% |
| | | avg. | | 1.36 | 2.8% | 307 | 1.38 | 3.4% |

| Expt. # | Matetial | Sample # | Balloon Internal Gas | Volume (Day 8) 7:00 PM | Pressure (Day 8) 7:00 PM | CO$_2$ % (Day 8) 7:00 PM | Volume (Day 9) 8:00 AM | Pressure (Day 9) 8:00 AM |
|---|---|---|---|---|---|---|---|---|
| | | | End of Cycle → | 0% CO$_2$ | 0% CO$_2$ | % Gas Gain | 50% CO$_2$ | 50% CO$_2$ |
| | | | | T = 8 (cc) | T = 8 (psi) | T = 8 (%) | T = 9 (cc) | T = 9 (psi) |
| | | | | | balloon cut during test | | | |
| 1 | Non-Barrier Film | 1 | N$_2$ | | | | | |
| | | 3 | | 318 | 2.88 | 15.1% | 323 | 2.96 |
| | | 4 | | 322 | 2.87 | 17.9% | 323 | 3.00 |
| | | 5 | | 325 | 2.96 | 17.4% | 323 | 3.01 |
| | | 6 | | 330 | 2.88 | 15.8% | 332 | 2.91 |
| | | avg. | | 324 | 2.90 | 16.6% | 325 | 2.97 |
| 2 | | 1B | N$_2$/CO$_2$ | 325 | 1.30 | 2.5% | 327 | 1.28 |
| | | 2B | (75%/25%) | 314 | 1.28 | 5.8% | 301 | 1.35 |
| | | 4B | | 300 | 1.32 | 3.0% | 298 | 1.45 |
| | | 5B | | 304 | 1.23 | 3.2% | 307 | 1.35 |
| | | 6B | | 299 | 1.34 | 2.7% | 299 | 1.39 |
| | | avg. | | 308 | 1.29 | 3.4% | 306 | 1.36 |

| Expt. # | Material | Sample # | Balloon Internal Gas | CO$_2$ % (Day 9) 8:00 AM | Volume (Day 12) 8:00AM | Pressure (Day 12) 8:00 AM | CO$_2$ % (Day 12) 8:00 AM | Volume (Day 13) 8:00 AM |
|---|---|---|---|---|---|---|---|---|
| | | | End of Cycle → | | | | % Gas Gain* | 50% CO2 |
| | | | | T = 9 (%) | T = 8 (cc) | T = 8 (psi) | T = 8 (%) | T = 9 (cc) |
| | | | | | balloon cut during test | | | |
| 1 | Non-Barrier Film | 1 | N$_2$ | | | | | |
| | | 3 | | 16.8% | 323 | 3.00 | 17.0% | 325 |
| | | 4 | | 18.8% | 322 | 3.25 | 19.7% | 326 |
| | | 5 | | 17.1% | 325 | 3.27 | 18.8% | 327 |
| | | 6 | | 16.5% | 330 | 3.25 | 17.6% | 333 |
| | | avg. | | 17.3% | 325 | 3.19 | 18.3% | 328 |
| 2 | | 1B | N$_2$/CO$_2$ | 2.9% | 326 | 1.62 | 4.2% | 330 |
| | | 2B | (75%/25%) | 3.1% | 302 | 1.62 | 4.5% | 304 |
| | | 4B | | 3.1% | 298 | 1.42 | 3.0% | 300 |
| | | 5B | | 4.4% | 305 | 1.66 | 5.3% | 309 |
| | | 6B | | 3.0% | 298 | 1.58 | 3.6% | 298 |
| | | avg. | | 3.3% | 306 | 1.58 | 4.1% | 308 |

TABLE 6-continued

| Expt. # | Material | Sample # | Balloon Internal Gas | Pressure (Day 13) 8:00 AM | $CO_2$ % (Day 13) 8:00 AM | Volume (Day 14) 8:00 AM | Pressure (Day 14) 8:00 AM | $CO_2$ % (Day 14) 8:00 AM |
|---|---|---|---|---|---|---|---|---|
| | | End of Cycle → | | 50% CO2 | % Gas Gain* | 50% CO2 | 50% CO2 | % Gas Gain* |
| | | | | T = 9 (psi) | T = 9 (%) | T = 10 (cc) | T = 10 (psi) | T = 10 (%) |
| 1 | Non-Barrier Film | 1 | $N_2$ | | | | | |
| | | 3 | | 3.37 | 19.2% | 323 | 3.25 | 18.1% |
| | | 4 | | 3.36 | 21.2% | 327 | 3.21 | 20.7% |
| | | 5 | | 3.38 | 19.8% | 326 | 3.36 | 19.5% |
| | | 6 | | 3.30 | 18.5% | 334 | 3.30 | 18.8% |
| | | avg. | | 3.35 | 19.7% | 328 | 3.28 | 19.3% |
| 2 | | 1B | $N_2/CO_2$ (75%/25%) | 1.68 | 5.3% | 329 | 1.68 | 5.1% |
| | | 2B | | 1.69 | 5.3% | 302 | 1.48 | 3.9% |
| | | 4B | | 1.56 | 4.1% | 299 | 1.43 | 3.3% |
| | | 5B | | 1.69 | 6.3% | 307 | 1.57 | 5.3% |
| | | 6B | | 1.70 | 4.1% | 300 | 1.66 | 4.4% |
| | | avg. | | 1.66 | 5.0% | 307 | 1.56 | 4.4% |

Balloons constructed with various composite walls, a barrier material Nylon12/PvDC/Nylon12/LLDPE+LDPE) and a non-barrier material (multi-layer Nylon12/LLDPE+LDPE) were tested in a simulated gastric environment (tank containing a 1.2 pH HCl solution with NaCl and pepsin at 40° C. with a variable $N_2/CO_2$ headspace (75%/25% to 100%/0%)). The balloons were initially filled with a mixture of $N_2$ (75%) and $CO_2$ (25%). Pressure for the balloons fabricated from $CO_2$ barrier materials maintained pressure and volume over the time period tested, whereas the balloons fabricated from $CO_2$ non-barrier materials exhibited substantial pressure gain over the same time period, with a smaller volume gain. Results are presented in Table 7.

TABLE 7

| Exp. | Material | Sample | Balloon Internal Gas | Volume (Day 0) (cc) | Pressure (Day 0) (psi) | Volume (Day 1) (cc) | Pressure (Day 1) (psi) |
|---|---|---|---|---|---|---|---|
| 1 | Barrier | 1 | $N_2/CO_2$ (75%/25%) | | | 280 | 1.05 |
| | | 2 | | | | 279 | 1.03 |
| | | avg. | | | | 280 | 1.04 |
| 2 | Barrier | 1 | $N_2/CO_2$ (75%/25%) | | | 279 | 1.06 |
| | | 2 | | | | 278 | 1.07 |
| | | avg. | | | | 279 | 1.07 |
| 3 | Barrier | 1 | $N_2/CO_2$ (75%/25%) | | | 280 | 1.05 |
| | | 2 | | | | 278 | 1.02 |
| | | avg. | | | | 279 | 1.04 |
| 4 | Barrier | 1 | $N_2/CO_2$ (75%/25%) | 296 | 1.14 | | |
| | | 2 | | 295 | 1.05 | | |
| | | avg. | | 296 | 1.10 | | |
| 5 | Non-Barrier | 1 | $N_2/CO_2$ (75%/25%) | 304 | 1.12 | | |
| | | 2 | | 292 | 1.11 | | |
| | | avg. | | 298 | 1.12 | | |
| 6 | Non-Barrier | 1 | $N_2/CO_2$ (75%/25%) | 298 | 1.15 | | |
| | | 2 | | 294 | 1.14 | | |
| | | avg. | | 296 | 1.15 | | |
| 7 | Non-Barrier | 1 | $N_2/CO_2$ (75%/25%) | 297 | 1.14 | | |
| | | 2 | | 302 | 1.15 | | |
| | | avg. | | 300 | 1.15 | | |
| 8 | Barrier | 1 | $N_2/CO_2$ (75%/25%) | 298 | 1.11 | | |
| | | 2 | | 302 | 1.12 | | |
| | | avg. | | 300 | 1.12 | | |
| 9 | Barrier | 1 | $N_2/CO_2$ (75%/25%) | 294 | 1.18 | | |
| | | 2 | | 291 | 1.13 | | |
| | | avg. | | 293 | 1.16 | | |

| Exp. | Material | Sample | Balloon Internal Gas | Volume (Day 2) (cc) | Pressure (Day 2) (psi) | Volume (Day 3) (cc) | Pressure (Day 3) (psi) |
|---|---|---|---|---|---|---|---|
| 1 | Barrier | 1 | $N_2/CO_2$ (75%/25%) | | | 286 | 1.05 |
| | | 2 | | | | 284 | 1.01 |
| | | avg. | | | | 285 | 1.03 |
| 2 | Barrier | 1 | $N_2/CO_2$ (75%/25%) | | | 283 | 0.97 |
| | | 2 | | | | 282 | 1.04 |
| | | avg. | | | | 283 | 1.01 |

TABLE 7-continued

| Exp. | Material | Sample | Balloon Internal Gas | | | | |
|------|----------|--------|----------------------|---|---|---|---|
| 3 | Barrier | 1 | $N_2/CO_2$ (75%/25%) | | 287 | 1.05 | |
| | | 2 | | | 280 | 0.97 | |
| | | avg. | | | 284 | 1.01 | |
| 4 | Barrier | 1 | $N_2/CO_2$ (75%/25%) | | 303 | 1.28 | |
| | | 2 | | | 303 | 1.18 | |
| | | avg. | | | 303 | 1.23 | |
| 5 | Non-Barrier | 1 | $N_2/CO_2$ (75%/25%) | | 313 | 2.26 | |
| | | 2 | | | 312 | 2.37 | |
| | | avg. | | | 313 | 2.32 | |
| 6 | Non-Barrier | 1 | $N_2/CO_2$ (75%/25%) | | 308 | 2.34 | |
| | | 2 | | | 301 | 2.15 | |
| | | avg. | | | 305 | 2.25 | |
| 7 | Non-Barrier | 1 | $N_2/CO_2$ (75%/25%) | | 307 | 2.17 | |
| | | 2 | | | 312 | 2.22 | |
| | | avg. | | | 310 | 2.20 | |
| 8 | Barrier | 1 | $N_2/CO_2$ (75%/25%) | | 303 | 1.28 | |
| | | 2 | | | 303 | 1.28 | |
| | | avg. | | | 303 | 1.28 | |
| 9 | Barrier | 1 | $N_2/CO_2$ (75%/25%) | | 301 | 1.24 | |
| | | 2 | | | 298 | 1.24 | |
| | | avg. | | | 300 | 1.24 | |

| Exp. | Material | Sample | Balloon Internal Gas | Volume (Day 4) (cc) | Pressure (Day 4) (psi) | Volume (Day 5) (cc) | Pressure (Day 5) (psi) |
|------|----------|--------|----------------------|---------------------|------------------------|---------------------|------------------------|
| 1 | Barrier | 1 | $N_2/CO_2$ (75%/25%) | 289 | 1.08 | 292 | 1.07 |
| | | 2 | | 287 | 1.03 | 292 | 1.04 |
| | | avg. | | 288 | 1.06 | 292 | 1.06 |
| 2 | Barrier | 1 | $N_2/CO_2$ (75%/25%) | 284 | 1.14 | 287 | 1.01 |
| | | 2 | | 286 | 1.13 | 287 | 1.02 |
| | | avg. | | 285 | 1.14 | 287 | 1.02 |
| 3 | Barrier | 1 | $N_2/CO_2$ (75%/25%) | 285 | 1.09 | 287 | 1.05 |
| | | 2 | | 285 | 1.05 | 286 | 1.00 |
| | | avg. | | 285 | 1.07 | 287 | 1.03 |
| 4 | Barrier | 1 | $N_2/CO_2$ (75%/25%) | 308 | 1.35 | 309 | 1.36 |
| | | 2 | | 306 | 1.39 | 306 | 1.29 |
| | | avg. | | 307 | 1.37 | 308 | 1.33 |
| 5 | Non-Barrier | 1 | $N_2/CO_2$ (75%/25%) | 320 | 2.44 | 322 | 2.51 |
| | | 2 | | 315 | 2.59 | 315 | 2.58 |
| | | avg. | | 318 | 2.52 | 319 | 2.55 |
| 6 | Non-Barrier | 1 | $N_2/CO_2$ (75%/25%) | 311 | 2.48 | 312 | 2.59 |
| | | 2 | | 306 | 2.39 | 308 | 2.51 |
| | | avg. | | 309 | 2.44 | 310 | 2.55 |
| 7 | Non-Barrier | 1 | $N_2/CO_2$ (75%/25%) | 310 | 2.43 | 308 | 2.45 |
| | | 2 | | 315 | 2.43 | 316 | 2.54 |
| | | avg. | | 313 | 2.43 | 312 | 2.50 |
| 8 | Barrier | 1 | $N_2/CO_2$ (75%/25%) | 305 | 1.39 | 305 | 1.36 |
| | | 2 | | 303 | 1.34 | 306 | 1.31 |
| | | avg. | | 304 | 1.37 | 306 | 1.34 |
| 9 | Barrier | 1 | $N_2/CO_2$ (75%/25%) | 303 | 1.30 | 304 | 1.29 |
| | | 2 | | 298 | 1.35 | 299 | 1.33 |
| | | avg. | | 301 | 1.33 | 302 | 1.31 |

Balloons constructed with composite walls with high $CO_2$ barrier properties (Experiments 1, 2, and 3) (Nylon12/PvDC/Nylon 12/LLDPE+LDPE) and walls having a higher permeability to $CO_2$ (Experiments 4, 5, and 6) consisting of multi-layer Nylon12/LLDPE+LDPE were exposed to a stimulated gastric environment. The simulated gastric environment comprised a tank containing a 1.2 pH HCl solution with NaCl and pepsin at 40° C. The headspace in the tank was cycled from a gas mixture comprising 75% $N_2$/25% $CO_2$ headspace to one comprising 100% $N_2$/0% $CO_2$. The balloons were initially filled with various mixtures of $N_2$ and $CO_2$, and volume was monitored. Data regarding volume changes are provided in Table 8. The balloons constructed using walls having a higher permeability to $CO_2$ gained substantially in volume compared to those with high $CO_2$ barrier properties. For the balloons constructed using walls having a higher permeability to $CO_2$, those with higher ratios of $N_2$ to $CO_2$ as initial fill gas gained less volume than those with lower ratios of $N_2$ to $CO_2$. The data demonstrate that permeation of $CO_2$ into balloons fabricated with walls having a higher permeability to $CO_2$ occurs quickly in the gastric environment, and that this process can be employed to assist with inflation in the early stages of implant.

TABLE 8

| Experiment | Material | Sample | Balloon Internal Gas | Volume (Day 1) 5:00 PM (cc) | Pressure (Day 1) 5:00 PM (psi) | Volume (Day 2) 8:00 AM (cc) | Pressure (Day 2) 8:00 AM (psi) |
|------------|----------|--------|----------------------|------------------------------|---------------------------------|------------------------------|---------------------------------|
| 1 | Barrier | 1 | N2/CO2 | 298 | 1.07 | 301 | 1.08 |
| | | 2 | (92%/8%) | 293 | 1.02 | 293 | 1.06 |

TABLE 8-continued

| Experiment | Material | Sample | Balloon Internal Gas | Volume (Day 1) 8 AM (cc) | Pressure (Day 1) 8 AM (psi) | Volume (Day 1) 8:30 PM (cc) | Pressure (Day 1) 8:30 PM (psi) |
|---|---|---|---|---|---|---|---|
| | | 3 | | 285 | 1.00 | 287 | 1.05 |
| | | avg. | | 296 | 1.05 | 297 | 1.07 |
| 2 | Barrier | 1 | N2/CO2 | 286 | 1.09 | 287 | 1.09 |
| | | 2 | (90%/10%) | 291 | 1.09 | 294 | 1.14 |
| | | 3 | | 293 | 1.08 | 298 | 1.13 |
| | | avg. | | 290 | 1.09 | 304 | 1.20 |
| 3 | Barrier | 1 | N2/CO2 | 290 | 1.10 | 295 | 1.15 |
| | | 2 | (85%/15%) | 290 | 1.02 | 290 | 1.03 |
| | | 3 | | 299 | 1.16 | 304 | 1.20 |
| | | avg. | | 293 | 1.09 | 293 | 1.09 |
| 4 | Non-Barrier | 1 | N2/CO2 | 290 | 1.04 | 298 | 1.54 |
| | | 2 | (92%/8%) | 292 | 1.07 | 300 | 1.60 |
| | | 3 | | 291 | 1.09 | 301 | 1.68 |
| | | avg. | | 291 | 1.07 | 299 | 1.57 |
| 5 | Non-Barrier | 1 | N2/CO2 | 283 | 1.07 | 293 | 1.64 |
| | | 2 | (90%/10%) | 287 | 1.05 | 295 | 1.60 |
| | | 3 | | 290 | 1.00 | 300 | 1.48 |
| | | avg. | | 287 | 1.04 | 294 | 1.62 |
| 6 | Non-Barrier | 1 | N2/CO2 | 287 | 1.06 | 297 | 1.76 |
| | | 2 | (85%/15%) | 298 | 1.07 | 307 | 1.66 |
| | | 3 | | 290 | 1.13 | 304 | 1.78 |
| | | avg. | | 292 | 1.09 | 302 | 1.71 |

| Experiment | Material | Sample | Balloon Internal Gas | Volume (Day 2) 8:30 PM (cc) | Pressure (Day 2) 8:30 PM (psi) | Volume (Day 3) 8 AM (cc) | Pressure (Day 3) 8 AM (psi) |
|---|---|---|---|---|---|---|---|
| 1 | Barrier | 1 | N2/CO2 | 301 | 1.11 | 301 | 1.13 |
| | | 2 | (92%/8%) | 295 | 1.06 | 302 | 1.10 |
| | | 3 | | 284 | 1.03 | 289 | 1.07 |
| | | avg. | | 298 | 1.09 | 302 | 1.12 |
| 2 | Barrier | 1 | N2/CO2 | 287 | 1.13 | 287 | 1.12 |
| | | 2 | (90%/10%) | 294 | 1.13 | 296 | 1.17 |
| | | 3 | | 297 | 1.15 | 300 | 1.19 |
| | | avg. | | 293 | 1.14 | 294 | 1.16 |
| 3 | Barrier | 1 | N2/CO2 | 294 | 1.17 | 297 | 1.21 |
| | | 2 | (85%/15%) | 290 | 1.08 | 294 | 1.10 |
| | | 3 | | 302 | 1.27 | 308 | 1.27 |
| | | avg. | | 295 | 1.17 | 300 | 1.19 |
| 4 | Non-Barrier | 1 | N2/CO2 | 296 | 1.48 | 297 | 1.72 |
| | | 2 | (92%/8%) | 298 | 1.55 | 302 | 1.81 |
| | | 3 | | 296 | 1.65 | 301 | 1.80 |
| | | avg. | | 297 | 1.56 | 300 | 1.78 |
| 5 | Non-Barrier | 1 | N2/CO2 | 291 | 1.56 | 294 | 1.80 |
| | | 2 | (90%/10%) | 295 | 1.50 | 295 | 1.67 |
| | | 3 | | 298 | 1.44 | 301 | 1.65 |
| | | avg. | | 293 | 1.53 | 297 | 1.71 |
| 6 | Non-Barrier | 1 | N2/CO2 (85%/15%) | 295 | 1.76 | 300 | 1.99 |

Human Gastric Environment

Balloons constructed with non-barrier film composite walls were tested in vivo in 10 patients in a clinical study for 30 days. The balloon wall comprised multi-layer Nylon 12/LLDPE+LDPE. One balloon per patient was administered. Balloons were filled with a mixed gas to approximately 245 cc with an average starting balloon pressure of 1.01 psi above atmosphere. The initial fill gas was 95% Nitrogen and 5% $CO_2$. At the end of 30 days, balloons remained full and firm, although ending pressure and volumes could not be discerned visually/endoscopically. Of the 10 balloons retrieved, 10 balloons had internal gas samples obtained, and 8 provided meaningful data. Table 9 provides the data retrieved from the balloons. The end gas samples are reflective of the gastric environment and are averaged as follows: 82.4% $N_2$, 10.6% $O_2$, 5.9% $CO_2$, and 0.84% Ar. Thus, the internal balloon environment reflects that of the average gastric environment gas concentrations. Data for the experiments is provided in Table 9.

TABLE 9

| Patient # | Starting Balloon Gas Concentration | | Ending Balloon Gas Concentration (% v/v, by MS) | | | |
|---|---|---|---|---|---|---|
| Patient # | [N2] | [CO$_2$] | [N2] | [O$_2$] | [CO$_2$] | [Ar] |
| 1 | 95.00 | 5.00 | 81.19 | 10.20 | 7.60 | 0.86 |
| 2 | 95.00 | 5.00 | 81.24 | 12.90 | 4.85 | 0.86 |
| 3 | 95.00 | 5.00 | 82.41 | 10.80 | 5.65 | 0.85 |
| 4 | 95.00 | 5.00 | 82.07 | 11.20 | 5.70 | 0.82 |
| 5 | 95.00 | 5.00 | 82.87 | 10.05 | 6.00 | 0.82 |
| 6 | 95.00 | 5.00 | 82.54 | 11.50 | 4.80 | 0.88 |
| 7 | 95.00 | 5.00 | Erroneous Sample | | | |
| 8 | 95.00 | 5.00 | 81.76 | 10.20 | 7.00 | 0.82 |
| 9 | 95.00 | 5.00 | Erroneous Sample | | | |
| 10 | 95.00 | 5.00 | 84.95 | 8.20 | 5.80 | 0.81 |
| Avg. | | | 82.38 | 10.63 | 5.93 | 0.84 |
| Std Dev | | | 1.20 | 1.36 | 0.97 | 0.03 |
| Max | | | 84.95 | 12.90 | 7.60 | 0.88 |
| Min | | | 81.19 | 8.20 | 4.80 | 0.81 |

In certain embodiments wherein it is desirable to maintain the starting pressure and volume of the device, this can be accomplished by matching the internal balloon environment at implant (i.e., the fill gases) closely to the gastric environment. In such embodiments, the balloon can be inflated with an initial gas fill gas comprising approximately 80-85% nitrogen, 8-12% oxygen, and 4-8% carbon dioxide. The concentration of argon and other in vivo gases can be considered inconsequential to the total volume/pressure, and may be omitted for convenience or included as desirable. To encourage inflation of the balloon in vivo, the starting concentrations of oxygen and/or carbon dioxide can be reduced.

Experiments were conducted to determine pressure in various balloons over time for different initial fill gases. In reference to FIG. 43, the initial fill gases included the following (vol. %): 100% $SF_6$; 100% $N_2$; 50% $SF_6$ in combination with 50% $N_2$; 25% $SF_6$ in combination with 75% $N_2$; and 18-20% $SF_6$ in combination with 78-80% $N_2$. One type of balloon tested included a composite polymeric wall including a layer of 3.5 mil polyethylene and a layer of nylon. Another type of balloon tested included an ethylene vinyl alcohol layer in the composite polymeric wall. As shown by the data presented in FIG. 43, the balloons including 100% $N_2$ as the fill gas exhibited slight increases in pressure over approximately the first 2-4 weeks of the test, followed by a loss of pressure over time. The balloon including an ethylene vinyl alcohol layer was able to maintain pressure at a level equal to or greater than to the initial fill pressure for approximately four months, while the balloon including a polyethylene/nylon wall was able to maintain such a pressure for approximately 1 month. Balloons including 100% $SF_6$ exhibited substantial increase in pressure over the first approx. 2 to 3 months, at which time the pressure tended to level off for the duration of the test. By adding $N_2$ to the $SF_6$, the pressure at which leveling occurred was lowered. A mixture of approx. 18-20% $SF_6$ with the remainder $N_2$ exhibited a modest rise in pressure over approx. one month followed by substantially level maintenance of pressure over an approx. 4 month period of time.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches. Where a range of values is provided, it is understood that the upper and lower limit, and each intervening value between the upper and lower limit of the range is encompassed within the embodiments.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An optical system for locating a volume-occupying intragastric device inside the body, the system comprising:
    an optical sensor configured to sense electromagnetic radiation;
    a volume-occupying intragastric device, the volume-occupying intragastric device comprising an intragastric balloon having a polymeric wall, a lumen, and a valve system configured for introducing an initial fill fluid into the lumen of the intragastric balloon when the intragastric balloon is in an in vivo gastric environment, the valve system comprising a swallowable catheter configured to releasably couple with the volume-occupying intragastric device; and a swallowable light-emitting marker configured to produce electromagnetic radiation, in an in vivo gastric environment, indicative of a location of the volume-occupying intragastric device or a component associated therewith.

2. The system of claim 1, wherein the light-emitting marker is configured to couple with the swallowable catheter.

3. The system of claim 1, further comprising a swallowable capsule configured to contain the intragastric balloon in an uninflated and compacted state, wherein the light-emitting marker is configured to couple with the volume-occupying intragastric device.

4. The system of claim 1, wherein the light-emitting marker is configured to couple with the volume-occupying intragastric device.

5. The system of claim 1, further comprising a sensor interface unit configured to electrically communicate with the optical sensor.

6. The system of claim 5, further comprising a system control unit configured to electrically communicate with the sensor interface unit and with the optical sensor.

7. The system of claim 6, further comprising a computer configured to electrically communicate with the system control unit and to display an identifier indicating the location of the light-emitting marker inside the body.

8. The system of claim 1, further comprising an initial fill fluid, wherein the polymeric wall is configured to have, under conditions of the in vivo gastric environment, a permeability to $CO_2$ of more than 10 cc/m²/day, such that a rate and an amount of diffusion of $CO_2$ from the in vivo gastric environment into the lumen of the intragastric balloon through the polymeric wall is controlled, at least in part, by a concentration of an inert gas in the initial fill fluid.

9. The system of claim 8, wherein the polymeric wall comprises a layer selected from the group consisting of:
a $CO_2$ barrier material comprising an ethylene vinyl alcohol layer,
a two layer $CO_2$ barrier material comprising a nylon layer and a polyethylene layer,
a three layer $CO_2$ barrier material comprising a nylon layer, a polyvinylidene chloride layer, and a polyethylene layer, and
a three layer $CO_2$ barrier material comprising a nylon layer, an ethylene vinyl alcohol layer, and a polyethylene layer.

10. The system of claim 8, wherein the initial fill fluid comprises $SF_6$ in one or more of liquid form, vapor form, or gaseous form.

11. The system of claim 8, wherein the initial fill fluid comprises gaseous $N_2$ and gaseous $SF_6$.

12. A method for optically locating a volume-occupying intragastric device inside a body of a patient, the method comprising:

introducing into the body of the patient, via swallowing, a volume-occupying intragastric device, the volume-occupying intragastric device releasably coupled with a catheter;

introducing into the body of the patient, via swallowing, a light-emitting marker configured to be sensed by an optical sensor;

sensing the light emitted by the light-emitting marker with the optical sensor; and confirming a location of the volume-occupying intragastric device inside the patient based on sensing the light emitted by the light-emitting marker.

13. The method of claim 12, wherein the volume-occupying intragastric device comprises an intragastric balloon in an uninflated state, and wherein the location of the intragastric balloon is inside the patient's stomach.

14. The method of claim 13, wherein the volume-occupying intragastric device comprises an intragastric balloon having a polymeric wall and lumen, the method further comprising:

introducing an initial fill fluid into the lumen of the intragastric balloon through the catheter so as to inflate the intragastric balloon, wherein the polymeric wall is configured to have, under conditions of an in vivo gastric environment, a permeability to $CO_2$ of more than 10 cc/m²/day; and exposing the inflated intragastric balloon to the in vivo intragastric environment for a useful life of at least 30 days, wherein a rate and an amount of diffusion of $CO_2$ from the in vivo gastric environment into the lumen of the intragastric balloon through the polymeric wall is controlled, at least in part, by a concentration of an inert gas in an initial fill fluid.

15. The method of claim 14, wherein the polymeric wall comprises a layer selected from the group consisting of:
a $CO_2$ barrier material comprising an ethylene vinyl alcohol layer,
a two layer $CO_2$ barrier material comprising a nylon layer and a polyethylene layer,
a three layer $CO_2$ barrier material comprising a nylon layer, a polyvinylidene chloride layer, and a polyethylene layer, and
a three layer $CO_2$ barrier material comprising a nylon layer, an ethylene vinyl alcohol layer, and a polyethylene layer.

16. The method of claim 14, wherein the initial fill fluid comprises $SF_6$ in one or more of liquid form, vapor form, or gaseous form.

17. The method of claim 14, wherein the initial fill fluid comprises gaseous $N_2$ and gaseous $SF_6$.

18. The method of claim 12, further comprising displaying on a computer an identifier indicating the location of the light-emitting marker.

19. The method of claim 12, wherein the intragastric balloon is in an uninflated and compacted state inside a swallowable capsule, wherein the light-emitting marker is coupled with the capsule.

20. The method of claim 12, wherein the optical sensor is coupled with volume-occupying intragastric device.

* * * * *